(12) United States Patent
Apicella et al.

(10) Patent No.: US 7,413,729 B2
(45) Date of Patent: Aug. 19, 2008

(54) SIALIC ACID PERMEASE SYSTEM

(75) Inventors: Michael A. Apicella, Solon, IA (US); Anthony Zaleski, Solon, IA (US); Bradford W. Gibson, Berkely, CA (US); Simon Allen, San Francisco, CA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 11/331,735

(22) Filed: Jan. 13, 2006

(65) Prior Publication Data

US 2006/0257961 A1    Nov. 16, 2006

Related U.S. Application Data

(60) Provisional application No. 60/643,500, filed on Jan. 13, 2005.

(51) Int. Cl.
*A61K 49/00* (2006.01)
(52) U.S. Cl. ..................................... 424/9.2
(58) Field of Classification Search ............ None
See application file for complete search history.

(56) References Cited

U.S. PATENT DOCUMENTS

| 3,561,444 A | 2/1971 | Boucher |
| 3,703,173 A | 11/1972 | Dixon |
| 4,624,251 A | 11/1986 | Miller |
| 4,635,627 A | 1/1987 | Gam |
| 4,962,091 A | 10/1990 | Eppstein et al. |

FOREIGN PATENT DOCUMENTS

WO    WO 94/07529    4/1994

OTHER PUBLICATIONS

Allen et al., (2005) Infect. Immun. 73, 5291-5300.
Andreoni et al., (1993) J Infect Dis 168, 227-231.
Bakaletz et al., (1999) Infect Immun 67, 2746-62.
Bouchet et al., (2003) PNAS 100, 8898-8903.
Campagnari et al., (1987) Infect Immun 55, 882-7.
Davidson et al., (2004) Annu Rev Biochem 73, 241-268.
Dunne, (2002) Clin Microbiol Rev 15, 155-66.
Edwards et al., (2000) Infect Immun 68, 5354-63.
Ehrlich et al., (2002) Jama 287, 1710-5.
Fleischmann et al., (1995) Science 269, 496-498, 507-512.
Fleischmann et al., (1995) EBI Database accession No. P44543.
Forward et al., (1997) J Bacteriol 179, 5482-5493.
Gaucher et al., (2000) Biochemistry 39, 12406-12414.
Gibson et al., (1997) J. Am. Soc. Mass Spectrom. 8, 645-658.
Goon et al., (2003) Proc Natl Acad Sci U S A 100(6): 3089-94.
Greiner et al., (2004) Infect Immun 72, 4249-4260.
Hagiwara et al., (1994) Carbohydr Res 263, 167-72.
Hood et al., (1996) Mol Microbiol 22, 951-65.
Hood et al., (1999) Mol Microbiol 33, 679-692.
Hood et al., (2001) Mol Microbiol 39, 341-350.
Jones et al., (2002) J Biol Chem 277, 14598-14611.
Kelly et al. (2001) FEMS Microbiology Reviews 25:405-424.
Ketterer et al., (1999) Infect Immun 67, 4161-70.
Kolker et al., (2004) Nucleic Acids Res 32, 2353-2361.
Lesse et al., (1990) J Immunol Methods 126, 109-117.
Lins et al., (2002) Angew Chem Int Ed Engl 41(18): 3405-7.
Mandrell et al., (1992) Infect Immun 60, 1322-1328.
Masoud et al., (1997) Biochemistry 36, 2091-2103.
Murphy et al., (2002) BMC Microbiol 2, 7.
Murti et al., (1986) Virology 149, 36-43.
O'Toole et al., (2000) Annu Rev Microbiol 54, 49-79.
Phillips et al., (1992) Biochemistry 31, 4515-4526.
Post (2001) Laryngoscope 111, 2083-94.
Rabus et al., (1999) Microbiology 145 (Pt 12), 3431-3445.
Rao et al., (1999) FEMS Microbiol Rev 23, 99-129.
Rayner et al., (1998) Jama 279, 296-9.
Schneider et al, (1991) J Exp Med 174, 1601-1605.
Schweda et al., (1993) Carbohydr Res 246, 319-330.
Sirakova et al., (1994) Infect Immun 62, 2002-20.
Severi et al., (2005) Mol. Microbiol. 58, 1173-1185.
Solana et al. (2001) FEBS Letters 509, 41-46.
Sutherland, (2001) Trends Microbiol 9, 222-7.
Swords et al., (2000) Mol Microbiol 37, 13-27.
Swords et al., (2003) J Endotoxin Res 9, 131-44.
Swords et al., (2004) Infect Immun 72, 106-13.
Teele et al., (1983) JAMA 249, 1026-1029.
Towbin et al., (1979) Proc Natl Acad Sci U S A 76, 4350-4354.
Tsai et al., (1982) Anal Biochem 119, 115-119.
Vimr et al., (1985) J Bacteriol 164, 845-853.
Vimr et al., (2002) Trends Microbiol 10, 254-7.
Vimr et al., (2000) Mol Microbiol 36, 1113-1123.
Vimr et al., (2004) Microbiol Mol Biol Rev 68, 132-153.
von Itzstein et al., (1993) Nature 363, 418-23.
Wozniak et al., (2003) PNAS 100, 7907-12.
Yamasaki et al., (1991) Mol Immunol 28, 1233-1242.
ISR from PCT/US2006/001108, Jul. 2006.

*Primary Examiner*—Jon P Weber
*Assistant Examiner*—Paul Martin
(74) *Attorney, Agent, or Firm*—Viksnins Harris & Padys PLLP

(57) ABSTRACT

This invention relates to purified sialic acid permease systems, and inhibitory agents of sialic acid permease systems.

15 Claims, 25 Drawing Sheets
(4 of 25 Drawing Sheet(s) Filed in Color)

Figure 3
(A)
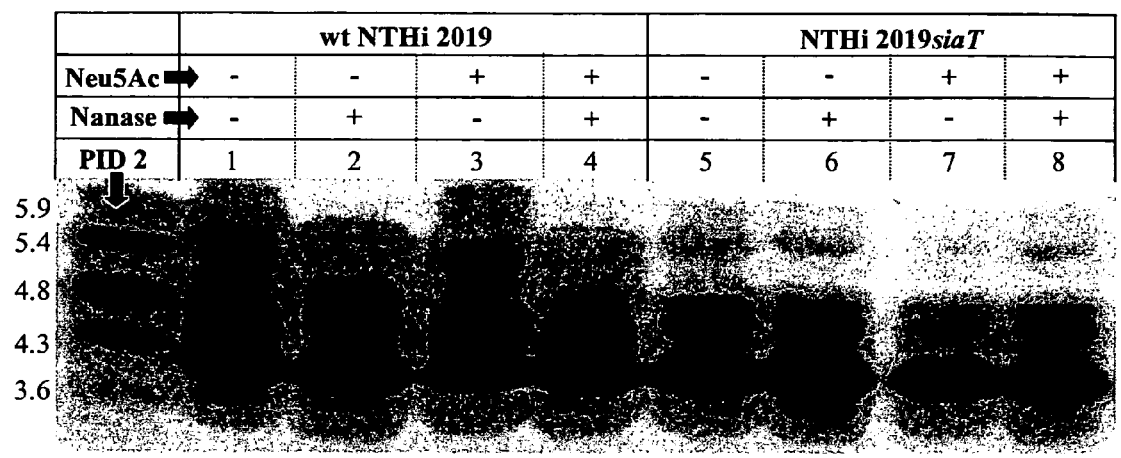
(B)
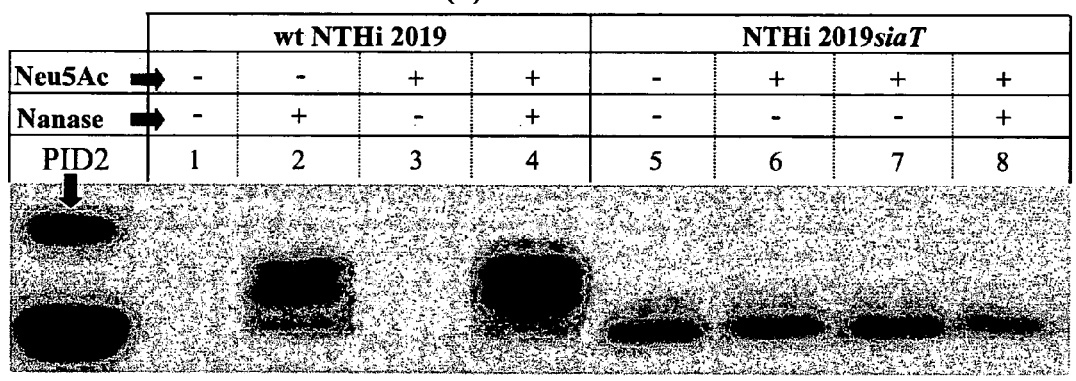

Figure 5
Normal Human Serum
A) BHI − Neu5Ac
B) BHI + Neu5Ac
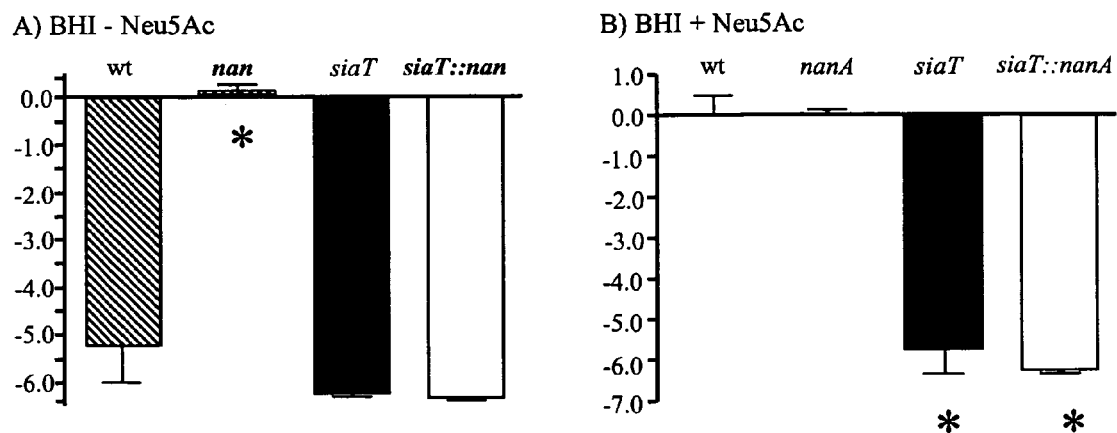
Heat-inactivated Serum
C) BHI − Neu5Ac
D) BHI + Neu5Ac
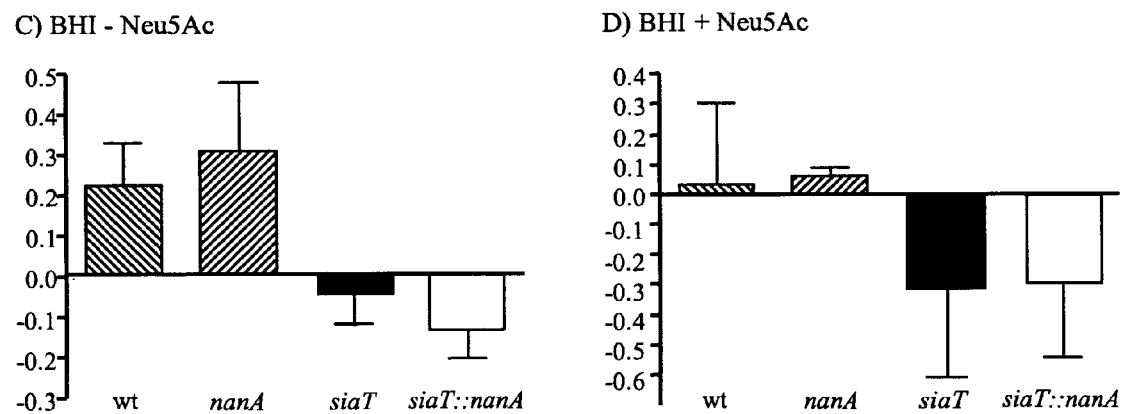

Figure 11: Permease Designated by TIGR as HI0147 – Amino Acid Sequence (SEQ ID NO:1)

```
              10         20         30         40         50
    60
       MCRNGPTFPY SSSNGVSMKY INKLEEWLGG ALFIAIFGIL IAQILSRQVF
HSPLIWSEEL 70         80         90        100        110
   120
       AKLLFVYVGM LGISVAVRKQ EHVFIDFLTN LMPEKIRKFT NTFVQLLVFI
CIFLFIHFGI 130        140        150        160        170
   180
       RTFNGASFPI DALGGISEKW IFAALPVVAI LMMFRFIQAQ TLNFKTGKSY
LPATFFIISA 190        200        210        220        230
   240
       VILFAILFFA PDWFKVLRIS NYIKLGSSSV YVALLVWLII MFIGVPVGWS
LFIATLLYFS 250        260        270        280        290
   300
       MTRWNVVNAA TEKLVYSLDS FPLLAVPFYI LTGILMNTGG ITERIFNFAK
ALLGHYTGGM 310        320        330        340        350
   360
       GHVNIGASLL FSGMSGSALA DAGGLGQLEI KAMRDAGYDD DICGGITAAS
CIIGPLVPPS 370        380        390        400        410
   420
       IAMIIYGVIA NESIAKLFIA GFIPGVLITL ALMAMNYRIA KKRGYPRTPK
ATREQLCSSF 430        440        450        460        470
   480
       KQSFWAILTP LLIIGGIFSG LFSPTESAIV AAAYSVIIGK FVYKELTLKS
LFNSCIEAMA 490        500        510        520        530
   540
       ITGVVALMIM TVTFFGDMIA REQVAMRVAD VFVAVADSPL TVLIMINALL
LFLGMFIDAL 550        560        570        580        590
   600
       ALQFLVLPML IPIAMQFNID LIFFGVMTTL NMMVGILTPP MGMALFVVAR
VGNMSVSTVT 610        620        630
       KGVLPFLIPV FVTLVLITIF PQIITFVPNL LIP
```

Length: 633 AA
Molecular weight: 69379 Da

Figure 12: Permease Designated by TIGR as HI0147 – Nucleic Acid Sequence (SEQ ID NO:2)

```
GTGTGCCGTAATGGCCCTACATTCCCTTATTCTTCATCAAACGGAGTGAGTATGAAATAT
ATTAATAAGCTTGAGGAATGGCTGGGTGGCGCATTATTTATCGCCATTTTCGGTATTCTT
ATCGCTCAAATTCTTTCACGCCAAGTTTTTCATTCTCCGTTAATTTGGAGTGAAGAACTC
GCCAAGCTCTTATTTGTTTACGTGGGTATGTTGGGTATCAGCGTTGCTGTGAGAAAACAA
GAACACGTATTTATTGATTTTTTAACTAATCTAATGCCCGAAAAAATCAGAAAATTCACA
AATACGTTTGTACAATTATTAGTCTTTATATGTATTTTCTTATTTATTCATTTCGGTATT
CGTACTTTTAACGGTGCATCATTCCCTATTGATGCCTTAGGAGGCATTTCTGAAAAATGG
ATTTTCGCAGCACTGCCTGTTGTCGCAATATTAATGATGTTTCGCTTTATCCAAGCGCAA
ACCCTAAACTTTAAGACTGGGAAAAGCTATTTACCTGCAACTTTCTTTATCATAAGTGCG
GTCATTTTATTTGCGATTTTATTTTTCGCGCCAGATTGGTTCAAAGTATTGCGTATTAGC
AATTATATAAAACTCGGTTCAAGTTCAGTCTATGTCGCCTTACTCGTTTGGCTAATCATT
ATGTTTATCGGTGTCCCTGTAGGTTGGTCCTTATTTATTGCTACTCTACTTTATTTTTCT
ATGACACGTTGGAACGTCGTAAATGCCGCAACTGAAAAATTAGTCTATAGCCTAGACAGC
TTCCCATTACTTGCCGTGCCATTTTATATTTTAACGGGCATTCTAATGAATACAGGTGGG
ATTACCGAACGTATTTTTAATTTTGCTAAAGCCTTACTCGGTCATTACACAGGAGGAATG
GGACACGTTAATATCGGCGCAAGTTTATTGTTCTCTGGTATGTCAGGTTCAGCACTTGCT
GATGCGGGGGGCTTAGGTCAATTGGAAATCAAAGCAATGCGTGATGCTGGTTATGACGAT
GATATTTGCGGAGGAATTACTGCTGCTTCTTGTATTATTGGGCCATTAGTTCCGCCAAGT
ATTGCAATGATTATTTACGGTGTAATTGCCAATGAATCTATCGCAAAACTCTTTATTGCA
GGTTTTATTCCAGGTGTATTAATTACTTTAGCTTTAATGGCAATGAATTATCGCATTGCA
AAAAAACGAGGTTATCCACGTACACCAAAAGCTACGAGAGAACAACTTTGCAGCAGCTTT
AAACAATCTTTTTGGGCAATCTTAACGCCGTTATTAATTATCGGTGGTATTTTTTCAGGC
TTATTCAGTCCAACAGAATCTGCCATTGTTGCAGCAGCATACTCTGTAATTATTGGTAAA
TTCGTGTATAAAGAATTAACCTTAAAAAGCTTATTTAATAGTTGCATAGAAGCAATGGCA
ATTACGGGCGTAGTCGCCCTTAATGATTATGACCGTGACTTTCTTTGGCGATATGATTGCG
CGTGAACAAGTCGCAATGCGTGTTGCTGATGTGTTTGTTGCCGTTGCCGATTCGCCTTTA
ACCGTATTGATAATGATTAACGCACTGTTACTTTTTCTTGGAATGTTCATTGATGCCCTA
GCATTACAATTTTTAGTATTACCAATGCTTATTCCTATCGCAATGCAGTTCAATATTGAC
TTAATCTTCTTTGGTGTAATGACCACATTAAATATGATGGTTGGTATTCTTACCCCACCA
ATGGGAATGGCTCTCTTTGTTGTTGCTCGTGTAGGAAATATGTCAGTTTCCACGGTAACC
AAAGGCGTATTACCGTTCTTGATTCCCGTTTTCGTCACATTAGTATTAATCACGATTTTC
CCACAAATCATCACATTTGTGCCAAATCTATTGATACCATAA
```

Figure 14
2019 sia T nucleotide sequence (SEQ ID NO:9)

```
ATGAAATATATTAATAAGCTTGAGGAATGGCTGGGTGGCGCATTATTTAT
CGCCATTTTCGGTATTCTTATCGCTCAAATTCTTTCACGCCAAGTTTTTCA
TTCTCCGTTAATTTGGAGTGAAGAACTCGCCAAGCTCTTATTTGTTTACGT
GGGTATGTTGGGTATCAGCGTTGCTGTGAGAAAACAAGAACACGTATTTA
TTGATTTTTTAACTAATCTAATGCCCGAAAAAATCAGAAAATTCACAAATA
CTCTTGTACAATTATTAGTCTTTATATGTATTTTCTTATTTATTCATTTCGGT
ATTCGTACTTTTAACGGCGCATCATTCCCTATTGATGCCTTAGGAGGCAT
TTCTGAGAAATGGATTTTCGCAGCACTGCCTGTTGTCGCAATATTAATGA
TGTTTCGCTTTATCCAAGCGCAAACCCTAAACTTTAAGACAGGGAAAAGC
TATTTACCTGCAACTTTCTTTATCATAAGTGCGGTCGTTTTATTTGCGATT
TTATTTTTCGCGCCAGATTGGTTCAAAGTATTGCGTATTAGCAATTATATA
AAACTCGGTTCAAGTTCAGTCTATGTCGCCTTACTTGTTTGGCTAATCATT
ATGTTTATCGGTGTCCCTGTAGGTTGGTCCTTATTTATTGCTACCTTACTT
TATTTTTCTATGACACGTTGGAATGTCGTAAATGCCGCAACTGAAAAATTA
GTCTATAGCCTAGACAGCTTTCCATTACTTGCCGTGCCGTTTTATATTTA
ACGGGTATTCTAATGAATACAGGTGGAATTACCGAACGCATTTTTAACTTT
GCTAAATCCTTACTCGGTCATTACACAGGAGGAATGGGACACGTTAATAT
CGGCGCAAGTTTATTGTTCTCTGGTATGTCAGGTTCAGCACTTGCTGATG
CGGGGGGGTTAGGTCAGCTTGAGATTAAAGCAATGCGTGATGCTGGTTA
TGACGATGATATTTGCGGAGGAATTACTGCTGCTTCTTGTATTATTGGGC
CATTAGTTCCACCGAGTATTGCAATGATTATTTACGGTGTCATCGCCAAT
GAATCTATCGCAAAACTCTTTATTGCAGGTTTTATTCCCGGTGTATTAATT
ACTTTAGCGTTAATGGCAATGAATTATCGCATTGCAAAAAAACGAGGTTA
TCCACGNACACCAAAAACCACGAGAGAACAACTTTGCAGCAGCTTTAAAC
AATCTTTTTGGGCAATCTTAACGCCATTATTAATTATCGGCGGTATTTTTT
CAGGCTTATTCAGTCCAACAGAATCTGCCATTGTTGCAGCAGCATACTCT
GTAATTATTGGTAAATTTGTGTATAAAGAATTAACCTTAAAAACCTTATTTA
ATAGTTGCATAGAAGCAATGGCAATTACAGGCGTAGTCGCCTTAATGATT
ATGACCGTGACTTTCTTTGGCGATATGATTGCCCGTGAACAAGTCGCAAT
GCGTGTTGCTAATGTGTTTGTTGCCGTTGCCGATTCGCCTTTAACCGTAT
TGGTAATGATTAACGCACTGTTACTTTTTCTTGGAATGTTCATTGATGCCC
TAGCATTACAATTTTTAGTATTACCAATGCTTATTCCTATCGCAATGCAATT
CAATATTGACTTAATCTTCTTTGGTGTAATGACCACATTAAATATGATGAT
TGGTATTCTTACCCCACCAATGGGAATGGCTCTCTTTGTTGTTGCTCGTG
TAGGTAATATGTCAGTTTCCACGGTAACCAAAGGCGTATTACCGTTCTTG
ATTCCCGTTTTCGTCACATTAGTATTAATCACGATTTTCCCACAAATCATC
ACATTTGTGCCAAATCTATTGATACCATAA
```

Figure 15
2019 sia T amino acid translation (SEQ ID NO:10)

MKYINKLEEWLGGALFIAIFGILIAQILSRQVFHSPLIWSEELAKLLFVYVGMLG
ISVAVRKQEHVFIDFLTNLMPEKIRKFTNTLVQLLVFICIFLFIHFGIRTFNGASF
PIDALGGISEKWIFAALPVVAILMMFRFIQAQTLNFKTGKSYLPATFFIISAVVL
FAILFFAPDWFKVLRISNYIKLGSSSVYVALLVWLIIMFIGVPVGWSLFIATLLY
FSMTRWNVVNAATEKLVYSLDSFPLLAVPFYILTGILMNTGGITERIFNFAKSL
LGHYTGGMGHVNIGASLLFSGMSGSALADAGGLGQLEIKAMRDAGYDDDIC
GGITAASCIIGPLVPPSIAMIIYGVIANESIAKLFIAGFIPGVLITLALMAMNYRIA
KKRGYPRTPKTTREQLCSSFKQSFWAILTPLLIIGGIFSGLFSPTESAIVAAAY
SVIIGKFVYKELTLKTLFNSCIEAMAITGVVALMIMTVTFFGDMIAREQVAMRV
ANVFVAVADSPLTVLVMINALLLFLGMFIDALALQFLVLPMLIPIAMQFNIDLIFF
GVMTTLNMMIGILTPPMGMALFVVARVGNMSVSTVTKGVLPFLIPVFVTLVLI
TIFPQIITFVPNLLIP*

Figure 16
2019 sia P nucleotide (SEQ ID NO:11)

ATGATGAAATTGACAAAACTTTTCCTTGCTACAGCCATTTCTTTAGGCGTA
TCTTCTGCTGTTCTTGCCGCTGACTATGACTTGAAATTCGGTATGAATGC
TGGAACTTCATCAAATGAATATAAAGCGGCAGAAATGTTTGCCAAAGAAG
TCAAAGAAAAATCACAGGGTAAAATTGAAATTTCACTTTATCCAAGTTCAC
AATTAGGTGATGACCGCGCAATGTTAAAACAATTAAAAGACGGTTCTCTC
GACTTTACCTTTGCAGAATCTGCTCGCTTCCAGCTGTTTTACCCTGAAGC
GGCAGTATTTGCCTTACCTTATGTTATTAGCAACTACAATGTTGCACAAAA
AGCCTTATTCGATACAGAATTCGGTAAAGATTTAATTAAAAAAATGGATAA
AGATCTTGGCGTGACTTTACTTTCCCAAGCTTATAACGGAACTCGCCAAA
CGACTTCAAATCGTGCAATCAACAGTATTGCAGATATGAAAGGCTTAAAA
CTTCGTGTGCCAAATGCAGCAACAAACTTAGCCTATGCTAAATATGTTGG
TGCATCACCAACACCAATGGCATTTTCTGAAGTTTATCTTGCGTTACAAAC
CAATGCCGTCGATGGTCAAGAAACCCGTTAGCAGCGGTGCAAGCACAA
AAATTCTATGAAGTGCAAAAGTTCTTAGCAATGACTAATCATATTTTGAAT
GACCAACTTTATTTAGTAAGCAACGAGACTTATAAAGAACTCCCTGAAGA
TCTTCAAAAAGTCGTAAAAGATGCTGCCGAAATGCAGCAAAATATCACA
CTAAATTATTCGTAGATGGAGAGAAAGATTTAGTCACATTCTTTGAAAAAC
AAGGCGTGAAAATTACACATCCTGATCTTGTTCCATTTAAAGAATCAATGA
AGCCGTATTATGCTGAGTTTGTAAAACAAACTGGTCAAAAAGGTGAATCA
GCTTTAAAACAAATTGAAGCAATCAATCCATAA

Figure 17
2019 siaP amino acid translation (SEQ ID NO:12)

MMKLTKLFLATAISLGVSSAVLAADYDLKFGMNAGTSSNEYKAAEMFAKEVK
EKSQGKIEISLYPSSQLGDDRAMLKQLKDGSLDFTFAESARFQLFYPEAAVF
ALPYVISNYNVAQKALFDTEFGKDLIKKMDKDLGVTLLSQAYNGTRQTTSNR
AINSIADMKGLKLRVPNAATNLAYAKYVGASPTPMAFSEVYLALQTNAVDGQ
ENPLAAVQAQKFYEVQKFLAMTNHILNDQLYLVSNETYKELPEDLQKVVKDA
AENAAKYHTKLFVDGEKDLVTFFEKQGVKITHPDLVPFKESMKPYYAEFVKQ
TGQKGESALKQIEAINP*

Figure 21: siaT homologies table

| Accession # | Species | E-value |
|---|---|---|
| ref\|NP_438316.1\| | Haemophilus influenzae Rd KW20 | 0.0 |
| ref\|ZP_00155990.1\| | Haemophilus influenzae R2866 | 0.0 |
| ref\|ZP_00154357.1\| | Haemophilus influenzae R2846 | 0.0 |
| ref\|YP_247867.1\| | Haemophilus influenzae 86-028NP | 0.0 |
| ref\|NP_246647.1\| | Pasturella multicida | 0.0 |
| ref\|NP_604367.1\| | Fusobacterium nucleatum 25586 | 0.0 |
| ref\|ZP_00143453.1\| | Fusobacterium nucleatum 49256 | 0.0 |
| ref\|NP_937256.1\| | Vibrio vulnificus YJ016 | 2e-124 |
| ref\|NP_762673.1\| | Vibrio vulnificus CMCP6 | 2e-124 |
| ref\|YP_130467.1\| | Photobacterium profundum | 2e-123 |
| ref\|NP_231412.1\| | Vibrio cholerae O1 | 6e-122 |
| ref\|NP_436827.1\| | Sinorhizobium meliloti | 1e-111 |
| ref\|ZP_00558435.1\| | Desulfitobacterium hafniense | 3e-86 |
| ref\|ZP_00472771.1\| | Desulfitobacterium hafniense DCB-2 | 7e-84 |
| ref\|ZP_00471246.1\| | Oceanobacillus iheyensis | 4e-81 |
| ref\|YP_066789.1\| | Bacillus halodurans | 1e-79 |
| ref\|YP_360137.1\| | Silicibacter pomeroyi | 2e-79 |
| ref\|ZP_00558990.1\| | Bacillus clausii | 2e-76 |
| ref\|NP_694177.1\| | Geobacillus kaustophilus | 7e-76 |
| ref\|NP_243537.1\| | Desulfovibrio desulfuricans | 1e-74 |

Figure 22: siaP Homologies Table

| Accesion # | Strain | E-value |
|---|---|---|
| |NP_438315.1| | Haemophilus influenzae Rd KW20 | 0.0 |
| |ZP_00154356.1| | Haemophilus influenzae R2846 | 0.0 |
| |ZP_00155989.1| | Haemophilus influenzae R2866 | 0.0 |
| |NP_246648.1| | Pasteurella multocida | 2e-134 |
| |NP_604366.1| | Fusobacterium nucleatum 25586 | 8e-119 |
| |NP_937258.1| | Vibrio vulnificus | 2e-83 |
| |YP_130469.1| | Photobacterium profundum | 7e-83 |
| |ZP_00143452.1| | Fusobacterium nucleatum 49256 | 3e-82 |
| |NP_231414.1| | Vibrio cholerae 1691 | 3e-80 |
| |NP_762675.1| | Vibrio vulnificus CMCP6 | 3e-80 |
| |NP_436825.1| | Sinorhizobium meliloti 1021 | 2e-56 |
| |ZP_00472769.1| | Chromohalobacter salexigens | 2e-47 |
| |NP_880562.1| | Bordetella pertussis Tohama I | 3e-43 |
| |NP_889190.1| | Bordetella bronchiseptica | 7e-43 |
| |NP_773474.1| | Bradyrhizobium japonicum | 2e-42 |
| |YP_177571.1| | Bacillus clausii | 4e-42 |
| |YP_360135.1| | Carboxydothermus hydrogenoformans... | 5e-42 |
| |YP_087241.1| | Mannheimia succiniciproducens | 6e-42 |

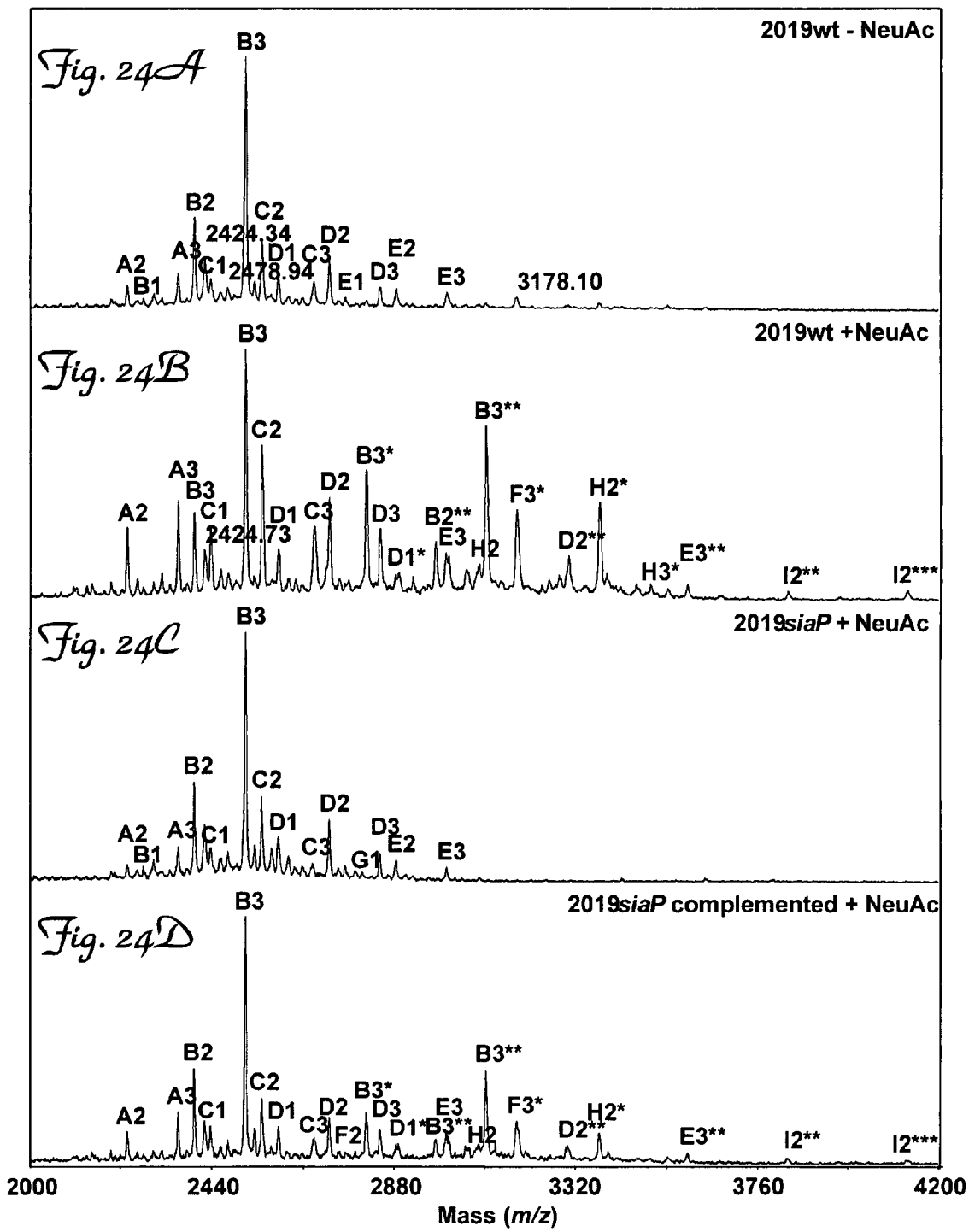

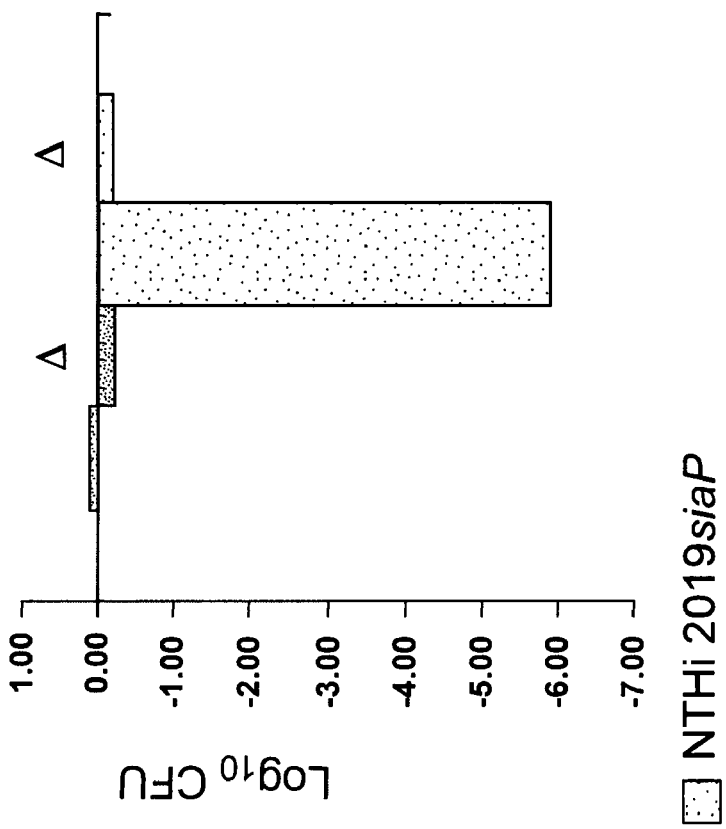
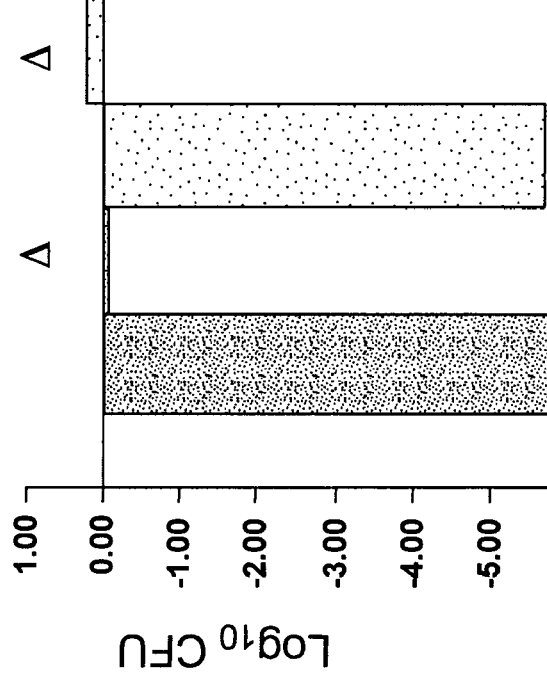
Fig. 25A  No Sialic Acid
Fig. 25B  + Sialic Acid
Resistance of NTHi 2019 and 2019siaP to 10% Pooled Normal Human Serum
NTHi 2019
NTHi 2019siaP A = Strain 2019
B = Strain 2019siaT
C = Strain 2019siaP
D = Strain 2019siaPsiaT

SEQUENCE LISTING

```
<160> NUMBER OF SEQ ID NOS: 12

<210> SEQ ID NO 1
<211> LENGTH: 633
<212> TYPE: PRT
```

<213> ORGANISM: Haemophilus influenzae

<400> SEQUENCE: 1

```
Met Cys Arg Asn Gly Pro Thr Phe Pro Tyr Ser Ser Ser Asn Gly Val
  1               5                  10                  15

Ser Met Lys Tyr Ile Asn Lys Leu Glu Glu Trp Leu Gly Gly Ala Leu
             20                  25                  30

Phe Ile Ala Ile Phe Gly Ile Leu Ile Ala Gln Ile Leu Ser Arg Gln
         35                  40                  45

Val Phe His Ser Pro Leu Ile Trp Ser Glu Glu Leu Ala Lys Leu Leu
     50                  55                  60

Phe Val Tyr Val Gly Met Leu Gly Ile Ser Val Ala Val Arg Lys Gln
 65                  70                  75                  80

Glu His Val Phe Ile Asp Phe Leu Thr Asn Leu Met Pro Glu Lys Ile
                 85                  90                  95

Arg Lys Phe Thr Asn Thr Phe Val Gln Leu Leu Val Phe Ile Cys Ile
            100                 105                 110

Phe Leu Phe Ile His Phe Gly Ile Arg Thr Phe Asn Gly Ala Ser Phe
        115                 120                 125

Pro Ile Asp Ala Leu Gly Gly Ile Ser Glu Lys Trp Ile Phe Ala Ala
    130                 135                 140

Leu Pro Val Val Ala Ile Leu Met Met Phe Arg Phe Ile Gln Ala Gln
145                 150                 155                 160

Thr Leu Asn Phe Lys Thr Gly Lys Ser Tyr Leu Pro Ala Thr Phe Phe
                165                 170                 175

Ile Ile Ser Ala Val Ile Leu Phe Ala Ile Leu Phe Phe Ala Pro Asp
            180                 185                 190

Trp Phe Lys Val Leu Arg Ile Ser Asn Tyr Ile Lys Leu Gly Ser Ser
        195                 200                 205

Ser Val Tyr Val Ala Leu Leu Val Trp Leu Ile Ile Met Phe Ile Gly
    210                 215                 220

Val Pro Val Gly Trp Ser Leu Phe Ile Ala Thr Leu Leu Tyr Phe Ser
225                 230                 235                 240

Met Thr Arg Trp Asn Val Val Asn Ala Ala Thr Glu Lys Leu Val Tyr
                245                 250                 255

Ser Leu Asp Ser Phe Pro Leu Leu Ala Val Pro Phe Tyr Ile Leu Thr
            260                 265                 270

Gly Ile Leu Met Asn Thr Gly Gly Ile Thr Glu Arg Ile Phe Asn Phe
        275                 280                 285

Ala Lys Ala Leu Leu Gly His Tyr Thr Gly Gly Met Gly His Val Asn
    290                 295                 300

Ile Gly Ala Ser Leu Leu Phe Ser Gly Met Ser Gly Ser Ala Leu Ala
305                 310                 315                 320

Asp Ala Gly Gly Leu Gly Gln Leu Glu Ile Lys Ala Met Arg Asp Ala
                325                 330                 335

Gly Tyr Asp Asp Asp Ile Cys Gly Gly Ile Thr Ala Ala Ser Cys Ile
            340                 345                 350

Ile Gly Pro Leu Val Pro Pro Ser Ile Ala Met Ile Ile Tyr Gly Val
        355                 360                 365

Ile Ala Asn Glu Ser Ile Ala Lys Leu Phe Ile Ala Gly Phe Ile Pro
    370                 375                 380

Gly Val Leu Ile Thr Leu Ala Leu Met Ala Met Asn Tyr Arg Ile Ala
385                 390                 395                 400
```

```
Lys Lys Arg Gly Tyr Pro Arg Thr Pro Lys Ala Thr Arg Glu Gln Leu
                405                 410                 415
Cys Ser Ser Phe Lys Gln Ser Phe Trp Ala Ile Leu Thr Pro Leu Leu
            420                 425                 430
Ile Ile Gly Gly Ile Phe Ser Gly Leu Phe Ser Pro Thr Glu Ser Ala
        435                 440                 445
Ile Val Ala Ala Tyr Ser Val Ile Gly Lys Phe Val Tyr Lys
    450                 455                 460
Glu Leu Thr Leu Lys Ser Leu Phe Asn Ser Cys Ile Glu Ala Met Ala
465                 470                 475                 480
Ile Thr Gly Val Val Ala Leu Met Ile Met Thr Val Thr Phe Phe Gly
                485                 490                 495
Asp Met Ile Ala Arg Glu Gln Val Ala Met Arg Val Ala Asp Val Phe
            500                 505                 510
Val Ala Val Ala Asp Ser Pro Leu Thr Val Leu Ile Met Ile Asn Ala
        515                 520                 525
Leu Leu Leu Phe Leu Gly Met Phe Ile Asp Ala Leu Ala Leu Gln Phe
    530                 535                 540
Leu Val Leu Pro Met Leu Ile Pro Ile Ala Met Gln Phe Asn Ile Asp
545                 550                 555                 560
Leu Ile Phe Phe Gly Val Met Thr Thr Leu Asn Met Met Val Gly Ile
                565                 570                 575
Leu Thr Pro Pro Met Gly Met Ala Leu Phe Val Val Ala Arg Val Gly
            580                 585                 590
Asn Met Ser Val Ser Thr Val Thr Lys Gly Val Leu Pro Phe Leu Ile
        595                 600                 605
Pro Val Phe Val Thr Leu Val Leu Ile Thr Ile Phe Pro Gln Ile Ile
    610                 615                 620
Thr Phe Val Pro Asn Leu Leu Ile Pro
625                 630

<210> SEQ ID NO 2
<211> LENGTH: 1902
<212> TYPE: DNA
<213> ORGANISM: Haemophilus influenzae

<400> SEQUENCE: 2
gtgtgccgta atggccctac attcccttat tcttcatcaa acggagtgag tatgaaatat    60
attaataagc ttgaggaatg gctgggtggc gcattattta tcgccatttt cggtattctt   120
atcgctcaaa ttctttcacg ccaagttttt cattctccgt aatttggag tgaagaactc    180
gccaagctct tatttgttta cgtgggtatg ttgggtatca gcgttgctgt gagaaaacaa   240
gaacacgtat ttattgattt tttaactaat ctaatgcccg aaaaaatcag aaaattcaca   300
aatacgtttg tacaattatt agtctttata tgtattttct tatttattca tttcggtatt   360
cgtacttta acggtgcatc attccctatt gatgccttag gaggcatttc tgaaaaatgg    420
atttttcgcag cactgcctgt tgtcgcaata ttaatgatgt ttcgctttat ccaagcgcaa   480
acccctaaact ttaagactgg gaaaagctat ttacctgcaa ctttctttat cataagtgcg   540
gtcattttat ttgcgatttt attttcgcg ccagattggt tcaaagtatt gcgtattagc    600
aattatataa aactcggttc aagttcagtc tatgtcgcct tactcgtttg gctaatcatt   660
atgtttatcg gtgtccctgt aggttggtcc ttatttattg ctactctact ttattttct   720
atgacacgtt ggaacgtcgt aaatgccgca actgaaaaat tagtctatag cctagacagc   780
```

-continued

```
ttcccattac ttgccgtgcc attttatatt ttaacgggca ttctaatgaa tacaggtggg      840
attaccgaac gtatttttaa ttttgctaaa gccttactcg gtcattacac aggaggaatg      900
ggacacgtta atatcggcgc aagtttattg ttctctggta tgtcaggttc agcacttgct      960
gatgcggggg gcttaggtca attggaaatc aaagcaatgc gtgatgctgg ttatgacgat     1020
gatatttgcg gaggaattac tgctgcttct tgtattattg gccattagt tccgccaagt     1080 attgcaatga ttatttacgg tgtaattgcc aatgaatcta tcgcaaaact ctttattgca     1140
ggttttattc caggtgtatt aattacttta gctttaatgg caatgaatta tcgcattgca     1200
aaaaaacgag gttatccacg tacaccaaaa gctacgagaa acaactttg cagcagcttt      1260 aaacaatctt tttgggcaat cttaacgccg ttattaatta tcggtggtat tttttcaggc     1320
ttattcagtc caacagaatc tgccattgtt gcagcagcat actctgtaat tattggtaaa     1380
ttcgtgtata agaattaac cttaaaaagc ttatttaata gttgcataga agcaatggca      1440
attacgggcg tagtcgcctt aatgattatg accgtgactt tctttggcga tatgattgcg     1500
cgtgaacaag tcgcaatgcg tgttgctgat gtgtttgttg ccgttgccga ttcgccttta     1560
accgtattga taatgattaa cgcactgtta cttttttcttg gaatgttcat tgatgcccta    1620
gcattacaat ttttagtatt accaatgctt attcctatcg caatgcagtt caatattgac     1680
ttaatcttct tggtgtaat gaccacatta aatatgatgg ttggtattct taccccacca     1740
atgggaatgg ctctctttgt tgttgctcgt gtaggaaata tgtcagtttc cacggtaacc    1800
aaaggcgtat taccgttctt gattcccgtt ttcgtcacat tagtattaat cacgattttc    1860
ccacaaatca tcacatttgt gccaaatcta ttgataccat aa                       1902
```

<210> SEQ ID NO 3  
<211> LENGTH: 34  
<212> TYPE: DNA  
<213> ORGANISM: Artificial Sequence  
<220> FEATURE:  
<223> OTHER INFORMATION: Description of Artificial Sequence: Synthetic primer

<400> SEQUENCE: 3
tcccccgggg tcatggaaag atacggatgc aaag        34

<210> SEQ ID NO 4  
<211> LENGTH: 33  
<212> TYPE: DNA  
<213> ORGANISM: Artificial Sequence  
<220> FEATURE:  
<223> OTHER INFORMATION: Description of Artificial Sequence: Synthetic primer

<400> SEQUENCE: 4
tcccccgggg tcaaaaggcg acaaagaggg tgg         33

<210> SEQ ID NO 5  
<211> LENGTH: 20  
<212> TYPE: DNA  
<213> ORGANISM: Artificial Sequence  
<220> FEATURE:  
<223> OTHER INFORMATION: Description of Artificial Sequence: Synthetic primer

<400> SEQUENCE: 5
tttcctacac gagcaacaac         20

<210> SEQ ID NO 6

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
ctacattccc ttattcttca tcaaac            26

<210> SEQ ID NO 7
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
ggaggaaaaa ataaagaggg ttataatgaa cgag            34

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
cacaaaaaat aggtacacga aaacaagtt aaggg            35

<210> SEQ ID NO 9
<211> LENGTH: 1851
<212> TYPE: DNA
<213> ORGANISM: Haemophilus influenzae
<220> FEATURE:
<221> NAME/KEY: modified_base
<222> LOCATION: (1170)
<223> OTHER INFORMATION: a, c, t, g, unknown or other

<400> SEQUENCE: 9

```
atgaaatata ttaataagct tgaggaatgg ctgggtggcg cattatttat cgccattttc      60
ggtattctta tcgctcaaat tctttcacgc caagttttc attctccgtt aatttggagt     120
gaagaactcg ccaagctctt atttgtttac gtgggtatgt tgggtatcag cgttgctgtg     180
agaaaacaag aacacgtatt tattgatttt ttaactaatc taatgcccga aaaaatcaga     240
aaattcacaa atactcttgt acaattatta gtctttatat gtattttctt atttattcat     300
ttcggtattc gtacttttaa cggcgcatca ttccctattg atgccttagg aggcatttct     360
gagaaatgga ttttcgcagc actgcctgtt gtcgcaatat aatgatgtt cgctttatc      420
caagcgcaaa ccctaaactt taagacaggg aaaagctatt tacctgcaac tttctttatc     480
ataagtgcgg tcgtttattt tgcgatttta tttttcgcgc cagattggtt caaagtattg     540
cgtattagca attatataaa actcggttca agttcagtct atgtcgcctt acttgtttgg     600
ctaatcatta tgtttatcgg tgtccctgta ggttggtcct tattatgc taccttactt      660
tatttttcta tgacacgttg gaatgtcgta aatgccgcaa ctgaaaaatt agtctataagc    720
ctagacagct ttccattact tgccgtgccg tttatattt taacgggtat tctaatgaat     780
acaggtggaa ttaccgaacg cattttaac tttgctaaat ccttactcgg tcattacaca     840
ggaggaatgg gacacgttaa tatcggcgca agtttattgt tctctggtat gtcaggttca     900
```

-continued

```
gcacttgctg atgcgggggg gttaggtcag cttgagatta aagcaatgcg tgatgctggt      960
tatgacgatg atatttgcgg aggaattact gctgcttctt gtattattgg gccattagtt     1020
ccaccgagta ttgcaatgat tatttacggt gtcatcgcca atgaatctat cgcaaaactc     1080
tttattgcag gttttattcc cggtgtatta attactttag cgttaatggc aatgaattat     1140
cgcattgcaa aaaacgagg ttatccacgn acaccaaaaa ccacgagaga acaactttgc      1200
agcagcttta acaatctttt tgggcaatc ttaacgccat tattaattat cggcggtatt     1260
ttttcaggct tattcagtcc aacagaatct gccattgttg cagcagcata ctctgtaatt     1320
attggtaaat ttgtgtataa agaattaacc ttaaaaacct tatttaatag ttgcatagaa     1380
gcaatggcaa ttacaggcgt agtcgcctta atgattatga ccgtgacttt ctttggcgat     1440
atgattgccc gtgaacaagt cgcaatgcgt gttgctaatg tgtttgttgc cgttgccgat     1500
tcgcctttaa ccgtattggt aatgattaac gcactgttac ttttctttgg aatgttcatt     1560
gatgccctag cattacaatt tttagtatta ccaatgctta ttcctatcgc aatgcaattc     1620
aatattgact taatcttctt tggtgtaatg accacattaa atatgatgat tggtattctt     1680 acccccaccaa tgggaatggc tctctttgtt gttgctcgtg taggtaatat gtcagttttcc    1740 acggtaacca aaggcgtatt accgttcttg attcccgttt tcgtcacatt agtattaatc     1800
acgattttcc cacaaatcat cacatttgtg ccaaatctat tgataccata a              1851
```

<210> SEQ ID NO 10
<211> LENGTH: 616
<212> TYPE: PRT
<213> ORGANISM: Haemophilus influenzae

<400> SEQUENCE: 10

```
Met Lys Tyr Ile Asn Lys Leu Glu Glu Trp Leu Gly Gly Ala Leu Phe
  1               5                  10                  15

Ile Ala Ile Phe Gly Ile Leu Ile Ala Gln Ile Leu Ser Arg Gln Val
             20                  25                  30

Phe His Ser Pro Leu Ile Trp Ser Glu Glu Leu Ala Lys Leu Leu Phe
         35                  40                  45

Val Tyr Val Gly Met Leu Gly Ile Ser Val Ala Val Arg Lys Gln Glu
     50                  55                  60

His Val Phe Ile Asp Phe Leu Thr Asn Leu Met Pro Glu Lys Ile Arg
 65                  70                  75                  80

Lys Phe Thr Asn Thr Leu Val Gln Leu Val Phe Ile Cys Ile Phe
                 85                  90                  95

Leu Phe Ile His Phe Gly Ile Arg Thr Phe Asn Gly Ala Ser Phe Pro
            100                 105                 110

Ile Asp Ala Leu Gly Gly Ile Ser Glu Lys Trp Ile Phe Ala Ala Leu
        115                 120                 125

Pro Val Val Ala Ile Leu Met Met Phe Arg Phe Ile Gln Ala Gln Thr
    130                 135                 140

Leu Asn Phe Lys Thr Gly Lys Ser Tyr Leu Pro Ala Thr Phe Phe Ile
145                 150                 155                 160

Ile Ser Ala Val Val Leu Phe Ala Ile Leu Phe Phe Ala Pro Asp Trp
                165                 170                 175

Phe Lys Val Leu Arg Ile Ser Asn Tyr Ile Lys Leu Gly Ser Ser Ser
            180                 185                 190

Val Tyr Val Ala Leu Leu Val Trp Leu Ile Ile Met Phe Ile Gly Val
        195                 200                 205
```

```
Pro Val Gly Trp Ser Leu Phe Ile Ala Thr Leu Leu Tyr Phe Ser Met
210                 215                 220

Thr Arg Trp Asn Val Val Asn Ala Ala Thr Glu Lys Leu Val Tyr Ser
225                 230                 235                 240

Leu Asp Ser Phe Pro Leu Leu Ala Val Pro Phe Tyr Ile Leu Thr Gly
                245                 250                 255

Ile Leu Met Asn Thr Gly Gly Ile Thr Glu Arg Ile Phe Asn Phe Ala
            260                 265                 270

Lys Ser Leu Leu Gly His Tyr Thr Gly Met Gly His Val Asn Ile
        275                 280                 285

Gly Ala Ser Leu Leu Phe Ser Gly Met Ser Gly Ser Ala Leu Ala Asp
290                 295                 300

Ala Gly Leu Gly Gln Leu Glu Ile Lys Ala Met Arg Asp Ala Gly
305                 310                 315                 320

Tyr Asp Asp Ile Cys Gly Ile Thr Ala Ala Ser Cys Ile Ile
                325                 330                 335

Gly Pro Leu Val Pro Ser Ile Ala Met Ile Ile Tyr Gly Val Ile
            340                 345                 350

Ala Asn Glu Ser Ile Ala Lys Leu Phe Ile Ala Gly Phe Ile Pro Gly
            355                 360                 365

Val Leu Ile Thr Leu Ala Leu Met Ala Met Asn Tyr Arg Ile Ala Lys
370                 375                 380

Lys Arg Gly Tyr Pro Arg Thr Pro Lys Thr Thr Arg Glu Gln Leu Cys
385                 390                 395                 400

Ser Ser Phe Lys Gln Ser Phe Trp Ala Ile Leu Thr Pro Leu Leu Ile
                405                 410                 415

Ile Gly Gly Ile Phe Ser Gly Leu Phe Ser Pro Thr Gly Ser Ala Ile
            420                 425                 430

Val Ala Ala Ala Tyr Ser Val Ile Ile Gly Lys Phe Val Tyr Lys Glu
            435                 440                 445

Leu Thr Leu Lys Thr Leu Phe Asn Ser Cys Ile Glu Ala Met Ala Ile
450                 455                 460

Thr Gly Val Val Ala Leu Met Ile Met Thr Val Thr Phe Phe Gly Asp
465                 470                 475                 480

Met Ile Ala Arg Glu Gln Val Ala Met Arg Val Ala Asn Val Phe Val
                485                 490                 495

Ala Val Ala Asp Ser Pro Leu Thr Val Leu Met Ile Asn Ala Leu
            500                 505                 510

Leu Leu Phe Leu Gly Met Phe Ile Asp Ala Leu Ala Leu Gln Phe Leu
        515                 520                 525

Val Leu Pro Met Leu Ile Pro Ile Ala Met Gln Phe Asn Ile Asp Leu
530                 535                 540

Ile Phe Phe Gly Val Met Thr Thr Leu Asn Met Met Ile Gly Ile Leu
545                 550                 555                 560

Thr Pro Pro Met Gly Met Ala Leu Phe Val Val Ala Arg Val Gly Asn
            565                 570                 575

Met Ser Val Ser Thr Val Thr Lys Gly Val Leu Pro Phe Leu Ile Pro
            580                 585                 590

Val Phe Val Thr Leu Val Leu Ile Thr Ile Phe Pro Gln Ile Ile Thr
            595                 600                 605

Phe Val Pro Asn Leu Leu Ile Pro
610                 615
```

<210> SEQ ID NO 11
<211> LENGTH: 990
<212> TYPE: DNA
<213> ORGANISM: Haemophilus influenzae

<400> SEQUENCE: 11

```
atgatgaaat tgacaaaact tttccttgct acagccattt ctttaggcgt atcttctgct      60
gttcttgccg ctgactatga cttgaaattc ggtatgaatg ctggaacttc atcaaatgaa     120
tataaagcgg cagaaatgtt tgccaaagaa gtcaaagaaa atcacaggg taaaattgaa      180
atttcacttt atccaagttc acaattaggt gatgaccgcg caatgttaaa acaattaaaa     240
gacggttctc tcgactttac ctttgcagaa tctgctcgct tccagctgtt ttaccctgaa     300
gcggcagtat ttgccttacc ttatgttatt agcaactaca atgttgcaca aaaagcctta     360
ttcgatacag aattcggtaa agatttaatt aaaaaaatgg ataaagatct tggcgtgact     420
ttactttccc aagcttataa cggaactcgc caaacgactt caaatcgtgc aatcaacagt     480
attgcagata tgaaaggctt aaaacttcgt gtgccaaatg cagcaacaaa cttagcctat     540
gctaaatatg ttggtgcatc accaacacca atggcatttt ctgaagttta tcttgcgtta     600
caaaccaatg ccgtcgatgg tcaagaaaac ccgttagcag cggtgcaagc acaaaaattc     660
tatgaagtgc aaaagttctt agcaatgact aatcatattt tgaatgacca actttattta     720
gtaagcaacg agacttataa agaactccct gaagatcttc aaaaagtcgt aaaagatgct     780
gccgaaaatg cagcaaaata tcacactaaa ttattcgtag atggagagaa agatttagtc     840
acattctttg aaaaacaagg cgtgaaaatt acacatcctg atcttgttcc atttaaagaa     900
tcaatgaagc cgtattatgc tgagtttgta aaacaaactg gtcaaaaagg tgaatcagct     960
ttaaaacaaa ttgaagcaat caatccataa                                      990
```

<210> SEQ ID NO 12
<211> LENGTH: 329
<212> TYPE: PRT
<213> ORGANISM: Haemophilus influenzae

<400> SEQUENCE: 12

```
Met Met Lys Leu Thr Lys Leu Phe Leu Ala Thr Ala Ile Ser Leu Gly
 1               5                  10                  15

Val Ser Ser Ala Val Leu Ala Ala Asp Tyr Asp Leu Lys Phe Gly Met
            20                  25                  30

Asn Ala Gly Thr Ser Ser Asn Glu Tyr Lys Ala Ala Glu Met Phe Ala
        35                  40                  45

Lys Glu Val Lys Glu Lys Ser Gln Gly Lys Ile Glu Ile Ser Leu Tyr
    50                  55                  60

Pro Ser Ser Gln Leu Gly Asp Asp Arg Ala Met Leu Lys Gln Leu Lys
65                  70                  75                  80

Asp Gly Ser Leu Asp Phe Thr Phe Ala Glu Ser Ala Arg Phe Gln Leu
                85                  90                  95

Phe Tyr Pro Glu Ala Ala Val Phe Ala Leu Pro Tyr Val Ile Ser Asn
            100                 105                 110

Tyr Asn Val Ala Gln Lys Ala Leu Phe Asp Thr Glu Phe Gly Lys Asp
        115                 120                 125

Leu Ile Lys Lys Met Asp Lys Asp Leu Gly Val Thr Leu Leu Ser Gln
    130                 135                 140

Ala Tyr Asn Gly Thr Arg Gln Thr Thr Ser Asn Arg Ala Ile Asn Ser
145                 150                 155                 160
```

```
-continued

Ile Ala Asp Met Lys Gly Leu Lys Leu Arg Val Pro Asn Ala Ala Thr
            165                 170             175

Asn Leu Ala Tyr Ala Lys Tyr Val Gly Ala Ser Pro Thr Pro Met Ala
            180             185             190

Phe Ser Glu Val Tyr Leu Ala Leu Gln Thr Asn Ala Val Asp Gly Gln
        195             200             205

Glu Asn Pro Leu Ala Ala Val Gln Ala Gln Lys Phe Tyr Glu Val Gln
        210             215             220

Lys Phe Leu Ala Met Thr Asn His Ile Leu Asn Asp Gln Leu Tyr Leu
225             230             235             240

Val Ser Asn Glu Thr Tyr Lys Glu Leu Pro Glu Asp Leu Gln Lys Val
            245             250             255

Val Lys Asp Ala Ala Glu Asn Ala Ala Lys Tyr His Thr Lys Leu Phe
            260             265             270

Val Asp Gly Glu Lys Asp Leu Val Thr Phe Phe Glu Lys Gln Gly Val
        275             280             285

Lys Ile Thr His Pro Asp Leu Val Pro Phe Lys Glu Ser Met Lys Pro
        290             295             300

Tyr Tyr Ala Glu Phe Val Lys Gln Thr Gly Gln Lys Gly Glu Ser Ala
305             310             315             320

Leu Lys Gln Ile Glu Ala Ile Asn Pro
            325
```

SIALIC ACID PERMEASE SYSTEM

CROSS REFERENCE TO RELATED APPLICATION

This application claims priority of invention under 35 U.S.C. § 119(e) from U.S. application Ser. No. 60/643,500 filed Jan. 13, 2005, the disclosure of which is incorporated by reference herein.

FEDERALLY SPONSORED RESEARCH OR DEVELOPMENT

The U.S. Government may have certain rights in this invention pursuant to Grant No. AI24616 and Grant No. AI30040 awarded by the National Institutes of Health.

TECHNICAL FIELD

This invention relates to purified sialic acid permease systems, and inhibitory agents of sialic acid permease systems.

BACKGROUND

*Haemophilus influenzae* is exclusively adapted to infect or colonize humans. Strains can be encapsulated or non-encapsulated (non-typeable). Non-typeable *Haemophilus influenzae* (NTHi) is a frequent colonizer of the nasopharynx and is an opportunistic pathogen. When the airway is compromised, NTHi can cause local infections such as otitis media in young children (24 million physician visits per year in the U.S. (Teele et al., (1983) JAMA 249, 1026-1029)) and chronic bronchitis and pneumonia in patients with chronic obstructive pulmonary disease. A major component of the outer membrane of *H. influenzae*, the lipooligosaccharides, plays an important role in microbial virulence and pathogenicity. N-Acetylneuraminic acid can be incorporated into the lipooligosaccharides as a terminal non-reducing sugar. Although much of the pathway of sialic acid incorporation into lipooligosaccharides is understood, the transporter responsible for N-acetylneuraminic acid uptake in *H. influenzae* has yet to be identified and characterized.

SUMMARY

Abbreviations used herein are the following: NTHi, non-typeable *Haemophilus influenzae*; LOS, lipooligosaccharide; O-LOS, O-deacylated lipooligosaccharide; Gal, galactose; Glc, glucose; Hep, heptose; Kdo, 3-deoxy-D-manno-octulosonic acid; Neu5Ac, N-acetylneuraminic acid (sialic acid); Hex, hexose; HexNAc, N-acetylhexosamine; TRAP transporter, tripartite ATP-independent periplasmic transporter; MALDI-TOF-MS, matrix assisted laser desorption time-of-flight mass spectrometry; PNHS, pooled normal human serum.

The present invention provides a method of treating a mammal infected with a bacterium containing a sialic acid permease system. The method involves administering a bacterial sialic acid permease system inhibitory agent to the mammal, wherein the inhibitor is administered in an amount that reduces the uptake of sialic acid by the bacterium. An exemplary mammal to be treated is a chinchilla or a human. In this method, the infecting bacterium is a pathogenic organism containing a TRAP with high homology to a sialic acid permease, and the bacterium has sialic acid as a part of the cell wall structure. Exemplary organisms include the following: *Haemophilus influenzae, Haemophilus somnus, H. gallarium, Vibrio vulnificus, Vibrio cholera, Shigella flexneri, Pseudomonas aeruginosa, Helicobacter pylori*, or *Pasturella multicidia, Salmonella enteritidis*. In certain situations, the mammal to be treated may be infected with a combination of bacterial strains.

The inhibitory agent may be a viral neuraminidase inhibitor, such as 3-fluoro-N-acetylneuraminic acid (3FNA), N-acetyl-2,3-didehydro-2-deoxyneuraminic acid (DDNA), the 4-guanidino-derivative of DDNA (Relenza®) or Tamiflu®. In particular, the inhibitor may be 3FNA. Alternatively, or additionally, the inhibitory agent may be an N-alkanoyl-derivative of sialic acid, such a 5-N-octanoyl derivative of sialic acid (SiaOct).

In the method of the present invention the uptake of sialic acid by the bacterium is reduced by at least 10%. It can be reduced by 20%, 30%, 40%, 50%, 60%, 70%, 80%, 90%, 95%, 96%, 97%, 98%, 99%, or even 100%.

In the method of the present invention, the mammal may be diagnosed with otitis media, otitis media with effusion, pneumonia, or chronic bronchitis.

In the method of the present invention, the sialic acid permease system may contain siaP or siaT.

The present invention also provides a purified polypeptide comprising a bacterial sialic acid permease enzyme, such as those listed in FIGS. 21 and 22, e.g., a *Haemophilus influenzae* sialic acid permease, a *Haemophilus somnus* sialic acid permease, a *H. gallarium* sialic acid permease, a *Vibrio vulnificus* sialic acid permease, a *Vibrio cholera* sialic acid permease, a *Shigella flexneri* sialic acid permease, a *Pseudomonas aeruginosa* sialic acid permease, a *Helicobacter pylori* sialic acid permease, a *Pasturella multicidia* sialic acid permease, a *Salmonella enteritidis* sialic acid permease. The sialic acid permease dicarboxylic acid permease made by, cloned from, or made synthetically to be the same as a dicarboxylic acid permease from one of the following organisms: *Polaromonas* sp. JS666, *Oceanobacillus iheyensis* HTE831, *Sinorhizobium meliloti* 1021, *Bacillus clausii* KSM-K16, *Desulfotalea psychrophila* LSv54, *Silicibacter* sp. TM1040, *Rhodobacter sphaeroides* 2.4.1, *Pseudomonas aeruginosa* UCBPP-PA14, *Escherichia coli* CFT073, *Pseudomonas aeruginosa* PAO1, *Salmonella typhimurium* LT2, *Bordetella parapertussis* 12822, *Desulfovibrio desulfuricans* G20, *Enterococcus faecium, Bordetella bronchiseptica* RB50, *Bacillus clausii* KSM-K16, *Microbulbifer degradans* 2-40, *Haemophilus influenzae* R2866, *Enterococcus faecalis* V583, *Silicibacter pomeroyi* DSS-3, *Agrobacterium tumefaciens* str. C58, *Desulfotalea psychrophila* LSv54; *Dechloromonas aromatica* RCB, *Helicobacter hepaticus* ATCC 51449, *Caulobacter crescentus* CB15, *Magnetococcus* sp. MC-1, *Mannheimia succiniciproducens* MBEL55E, *Haemophilus somnus* 129PT, *Pasteurella multocida* subsp. *multocida* str. Pm70, *Escherichia coli* K12, *Rhodospirillum rubrum, Bacillus licheniformis* ATCC 14580 (DSM 13), *Fusobacterium nucleatum* subsp. *nucleatum* ATCC 25586, *Azoarcus* sp. EbN1, *Salmonella enterica* subsp. *enterica* serovar Typhi Ty2, *Pseudomonas aeruginosa* UCBPP-PA14, *Azotobacter vinelandii, Shigella flexneri* 2a str. 301, *Salmonella enterica* subsp. *enterica* serovar Paratypi A str. ATCC 9150, *Pasteurella multocida* subsp. *multocida* str. Pm70, *Vibrio vulnificus* YJ016, *Photorhabdus luminescens* subsp. *laumondii* TT01, *Wolinella succinogenes* DSM 1740, *Haemophilus somnus* 2336, *Burkholderia fungorum* LB400, *Shigella flexneri* 2a str. 301, *Bradyrhizobium japonicum* USDA 110, *Desulfovibrio vulgaris* subsp. *vulgaris* str. Hildenborough, *Geobacillus kaustophilus* HTA426, *Bacillus halodurans* C-125, *Vibrio cholerae* O1 biovar eltor str. N16961, Haemophilus influenzae 86-028NP, Haemophilus somnus 129PT, and *Fusobacterium nucleatum* subsp. *vincentii* ATCC 49256.

The sialic acid permease polypeptide of the present invention may be siaP or siaT. In one embodiment, the polypeptide comprises an amino acid sequence encoded by SEQ ID NO:1, SEQ ID NO:10, or SEQ ID NO:12. In one embodiment, the permease is encoded by the nucleic acid of SEQ ID NO:2, SEQ ID NO:9, or SEQ ID NO:11.

The present invention further provides a method of determining sialic acid permease binding activity of an agent by contacting a sialic acid permease with the agent, and determining if the agent binds to the sialic acid permease. In the method of the present invention, the sialic acid permease may be a *Haemophilus influenzae* sialic acid permease, a *Haemophilus somnus* sialic acid permease, a *H. gallarium* sialic acid permease, a *Vibrio vulnificus* sialic acid permease, a *Vibrio cholera* sialic acid permease, a *Shigella flexneri* sialic acid permease, a *Pseudomonas aeruginosa* sialic acid permease, a *Helicobacter pylori* sialic acid permease, a *Pasturella multicidia* sialic acid permease, a *Salmonella enteritidis* sialic acid permease. The sialic acid permease dicarboxylic acid permease may be made by, cloned from, or made synthetically to be the same as a dicarboxylic acid permease from one of the following organisms: *Polaromonas* sp. JS666, *Oceanobacillus iheyensis* HTE831, *Sinorhizobium meliloti* 1021, *Bacillus clausii* KSM-K 16, *Desulfotalea psychrophila* LSv54, *Silicibacter* sp. TM1040, *Rhodobacter sphaeroides* 2.4.1, *Pseudomonas aeruginosa* UCBPP-PA14, *Escherichia coli* CFT073, *Pseudomonas aeruginosa* PAO1, *Salmonella typhimurium* LT2, *Bordetella parapertussis* 12822, *Desulfovibrio desulfuricans* G20, *Enterococcus faecium*, *Bordetella bronchiseptica* RB50, *Bacillus clausii* KSM-K16, *Microbulbifer degradans* 2-40, *Haemophilus influenzae* R2866, *Enterococcus faecalis* V583, *Silicibacter pomeroyi* DSS-3, *Agrobacterium tumefaciens* str. C58, *Desulfotalea psychrophila* LSv54, *Dechloromonas aromatica* RCB, *Helicobacter hepaticus* ATCC 51449, *Caulobacter crescentus* CB15, *Magnetococcus* sp. MC-1, *Mannheimia succiniciproducens* MBEL55E, *Haemophilus somnus* 129PT, *Pasteurella multocida* subsp. *multocida* str. Pm70, *Escherichia coli* K12, *Rhodospirillum rubrum*, *Bacillus licheniformis* ATCC 14580 (DSM 13), *Fusobacterium nucleatum* subsp. *nucleatum* ATCC 25586, *Azoarcus* sp. EbN1, *Salmonella enterica* subsp. *enterica* serovar *Typhi* Ty2, *Pseudomonas aeruginosa* UCBPP-PA14, *Azotobacter vinelandii*, *Shigella flexneri* 2a str. 301, *Salmonella enterica* subsp. *enterica* serovar *Paratypi A* str. ATCC 9150, *Pasteurella multocida* subsp. *multocida* str. Pm70, *Vibrio vulnificus* YJ016, *Photorhabdus luminescens* subsp. *laumondii* TTO1, *Wolinella succinogenes* DSM 1740, *Haemophilus somnus* 2336, *Burkholderia fungorum* LB400, *Shigella flexneri* 2a str. 301, *Bradyrhizobium japonicum* USDA 110, *Desulfovibrio vulgaris* subsp. *vulgaris* str. Hildenborough, *Geobacillus kaustophilus* HTA426, *Bacillus halodurans* C-125, *Vibrio cholerae* O1 biovar eltor str. N16961, *Haemophilus influenzae* 86-028NP, *Haemophilus somnus* 129PT, and *Fusobacterium nucleatum* subsp. *vincentii* ATCC 49256.

The sialic acid permease polypeptide of the present invention may be siaP or siaT. In one embodiment, the polypeptide comprises an amino acid sequence encoded by SEQ ID NO:1, SEQ ID NO:10, or SEQ ID NO:12. In one embodiment, the permease is encoded by the nucleic acid of SEQ ID NO:2, SEQ ID NO:9, or SEQ ID NO:11.

The present invention further provides a method of determining potential sialic acid permease system inhibitory activity of an agent in a bacterium containing a sialic acid permease system by contacting a bacterium with the agent, and determining if the agent interferes with sialic acid transport into the bacterium (or into a cellular membrane structure of the bacterium). Exemplary organisms include the following: *Haemophilus influenzae*, *Haemophilus somnus*, *H. gallarium*, *Vibrio vulnificus*, *Vibrio cholera*, *Shigella flexneri*, *Pseudomonas aeruginosa*, *Helicobacter pylori*, or *Pasturella multicidia*, *Salmonella enteritidis*. In the present method, the sialic acid transport maybe reduced by at least about 10%. It can be reduced by 20%, 30%, 40%, 50%, 60%, 70%, 80%, 90%, 95%, 96%, 97%, 98%, 99%, or even 100%.

The present invention provides a method of treating a patient against bacterial colonization or infection by administering to the patient an effective amount of a sialic acid permease system inhibitory agent in combination with a physiologically-acceptable, non-toxic vehicle.

The present invention provides a method of treating or preventing a *Haemophilus influenzae* infection, comprising administering to a patient a sialic acid permease system inhibitory agent.

The present invention provides a method for modulating sialic acid permease system activity comprising administering a sialic acid permease system inhibitory agent to a cell. The inhibitory agent may be a viral neuraminidase inhibitor, such as 3-fluoro-N-acetylneuraminic acid (3FNA), N-acetyl-2,3-didehydro-2-deoxyneuraminic acid (DDNA), the 4-guanidino-derivative of DDNA (Relenza®) or Tamiflu®. Alternatively, or additionally, the inhibitory agent may be an N-alkanoyl-derivative of sialic acid, such a 5-N-octanoyl derivative of sialic acid (SiaOct). The sialic acid permease polypeptide of the present invention may be siaP or siaT. In one embodiment, the polypeptide comprises an amino acid sequence encoded by SEQ ID NO:1, SEQ ID NO:10, or SEQ ID NO:12. In one embodiment, the permease is encoded by the nucleic acid of SEQ ID NO:2, SEQ ID NO:9, or SEQ ID NO:11.

As used herein "a" or "an" means one or more, unless specifically indicated to mean only one.

The details of one or more embodiments of the invention are set forth in the accompanying drawings and the description below. Other features, objects, and advantages of the invention will be apparent from the description and drawings, and from the claims.

DESCRIPTION OF DRAWINGS

This patent or application file contains at least one drawing executed in color. Copies of this patent or patent application publication with color drawing(s) will be provided by the Office upon request and payment of the necessary fee.

NTHi 2019 wild-type:☐

2019nanA:■

2019siaT:▨

2019nanA::siaT▧

Mid-log bacteria were pelleted and resuspended in RPMI containing a final concentration of 3.3 µM unlabelled sialic acid and 0.7 µM [$^3$H]-sialic acid. Samples were removed to a Nuclepore membrane at 10-15 seconds, then 0.5, 1, 3 and 5 minutes, aspirated, washed and the sample counted in scintillation fluid.

FIG. 3. A. SDS-PAGE of LOS isolated from NTHi 2019 wild-type and NTHi 2019siaT. Lanes 1-4, LOS isolated from wild-type NTHi 2019, lanes 5-8, LOS isolated from the mutant NTHi 2019siaT. Bacteria were grown on BHI in the absence (lanes 1, 2, 5 and 6) or presence (lanes 3, 4, 7 and 8) of Neu5Ac. LOS samples in lanes 2, 4, 6, and 8 were treated with neuraminidase prior to loading. LOS from *N. gonorrhoeae* strain PID2 was used as a molecular weight standard. The LOS was visualized using silver stain. B, Western blot of LOS probed with 3F11. Lanes 1, 3, 5 and 7 LOS isolated from wild-type NTHi 2019, lanes 2, 4, 6 and 8, LOS isolated from the mutant NTHi 2019siaT. Bacteria were grown on BHI in the absence (lanes 1-4) or presence (lanes 5-8) of Neu5Ac. LOS samples in lanes 3, 4, 7 and 8 were treated with neuraminidase prior to loading. LOS from *N. gonorrhoeae* strain PID2 was used as a molecular weight standard. LOS was probed with the monoclonal antibody 3F11, which recognizes a terminal N-acetyllactosamine structure. Antibody binding was detected using peroxidase-labeled goat anti-mouse IgM and chemiluminescent substrate.

Figure 4:
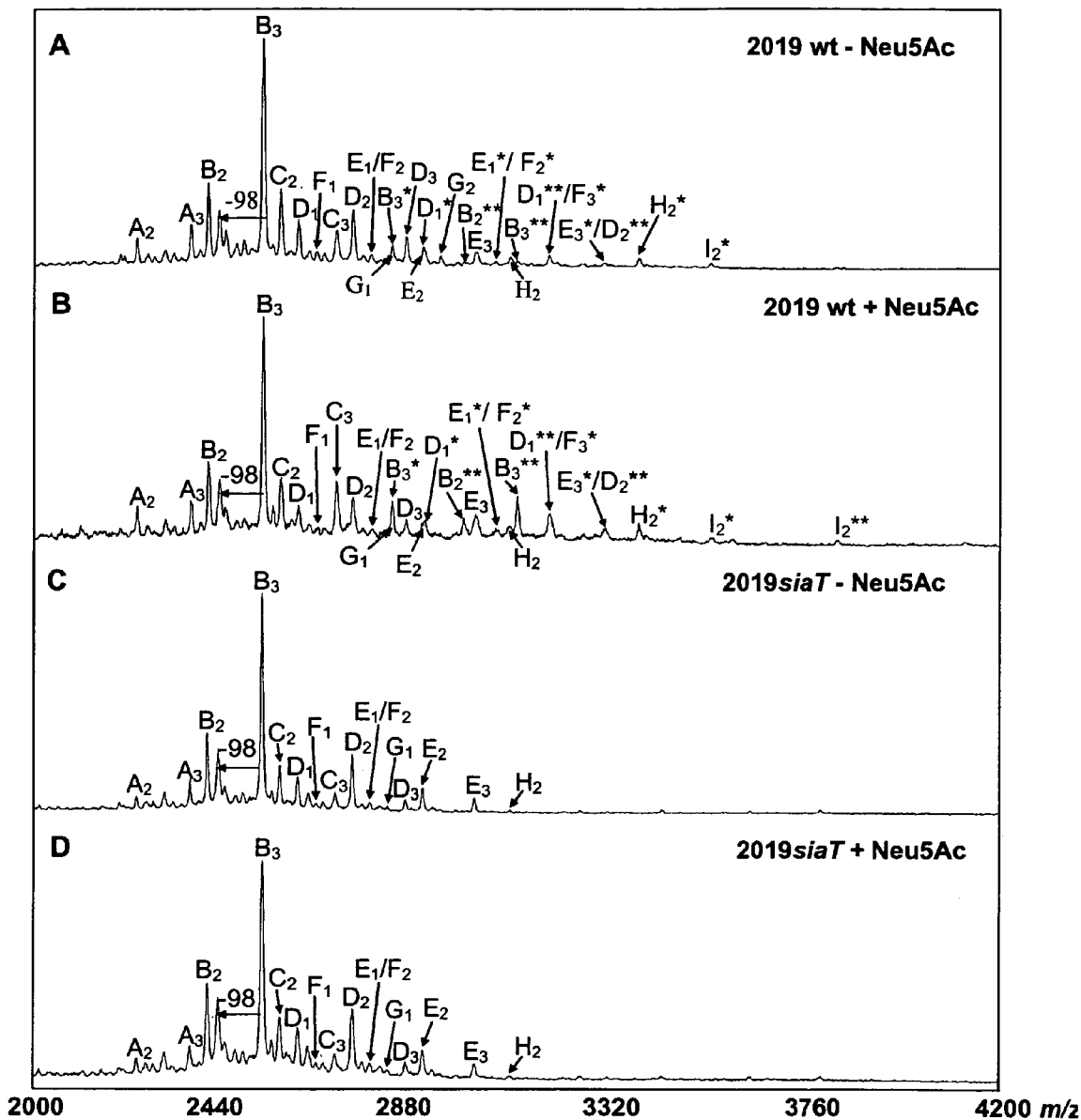

FIG. 4. Negative ion MALDI-TOF mass spectra of O-deacylated LOS from wild-type NTHi 2019 and the mutant NTHi 2019siaT. A, O-LOS from wild-type NTHi 2019 grown on solid media without supplemental Neu5Ac, B, O-LOS from wild-type NTHi 2019 grown on solid media supplemented with Neu5Ac, C, O-LOS from mutant NTHi 2019siaT grown without supplemental Neu5Ac, D, O-LOS from mutant NTHi 2019siaT grown with supplemental Neu5Ac. See Table 2 for molecular weights and proposed compositions. Asterisks indicate the addition and number of Neu5Ac, subscript type indicates the number of PEA moieties.

FIG. 5. Resistance to serum killing of wild-type NTHi and mutants NTHi 2019nanA, NTHi 2019siaT and NTHi 2019nanA::siaT. A and C, bacteria were grown on BHI without supplemental Neu5Ac, B and D, bacteria grown on BHI with supplemental Neu5Ac. A and B were exposed to normal human serum for 30 minutes at 37° C. from a 20-donor pool of serum from human volunteers with no previous history of neisserial infections. C and D were controls exposed to normal human serum that was heat-inactivated at 56° C. for 30 minutes. The ability of the bacteria to grow after treatment with serum was assessed by comparison to growth of untreated bacteria. Serum killing is expressed as $\log_{10}$ change in CFU between treated and untreated bacteria.

Figure 6:
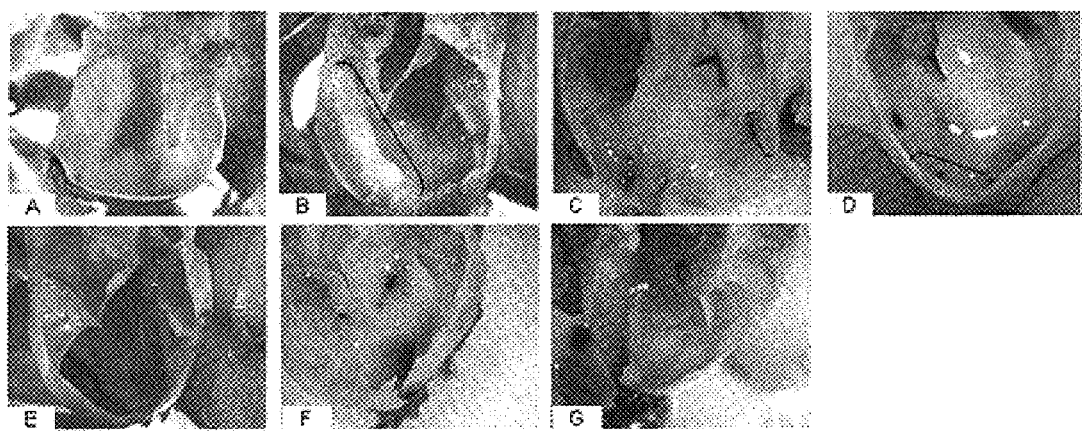

FIG. 6. Gross whole-mount images of bullae recovered 5 days post-challenge from chinchillas inoculated transbullarly with NTHi strain 2019 or a mutant derivative thereof. Brackets indicate any demonstrable biofilms (if present). Panel A is a bulla from a naive chinchilla for comparison. Panel B shows large biofilm formed by strain 2019. Strains 2019lsgB and 2019siaA (panels C and D, respectively) induce small biofilms identifiable by stereo microscopy. Strains 2019wecA, 2019siaB, and 2019pgm (panels E, F, and G, respectively) do not induce the formation of an identifiable biofilm via gross examination.

Figure 7:
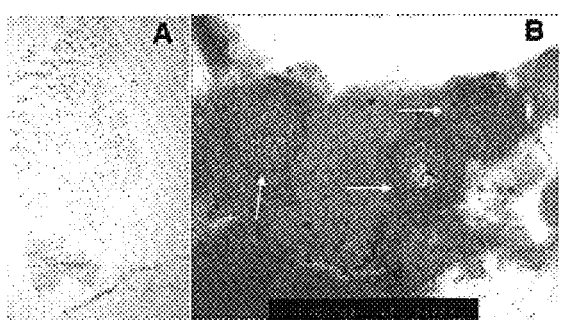

FIG. 7. A shows H&E stain of an OCT-embedded biofilm produced by strain 2019 in the chinchilla middle ear (5× magnification). Note numerous water channels present within the biofilm. B shows TEM analysis of OCT-embedded biofilm formed by NTHi strain 2019 in the middle ear of a chinchilla. Arrows indicate organisms surrounded by the biofilm matrix. The sections were incubated with *Sambucus nigra* lectin conjugated to 15 nm gold beads. The gold beads bound to the biofilm matrix and not to the bacteria.

Figure 8:
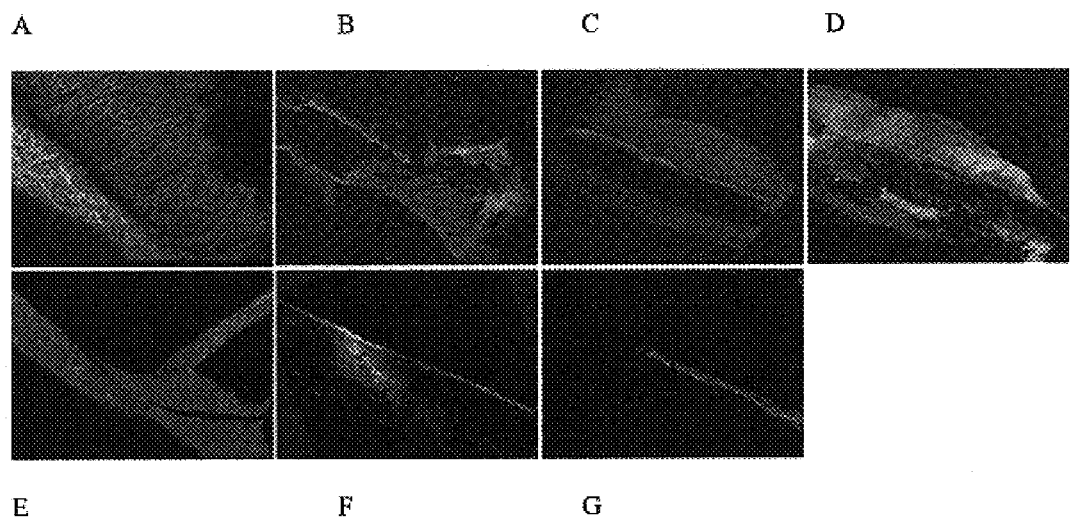

FIG. 8. Confocal microscopy images of whole mount sections of chinchilla inferior bulla (white arrows indicate bullar bone in each panel) stained with Live/Dead™ bacterial stain 5 days post NTHi challenge. The parent strain, 2019 (panel A), demonstrates a characteristic biofilm (white bracket) with long finger-like projections separated by water channels that extend well into the middle ear space. Strain 2019pgm (panel B) forms a very small biofilm with water channels present but appears less organized. Strains 2019lsgB (panel C) and 2019siaA (panel D) form very dense biofilms with no water channels observed and a larger population of dead cells (red stain) than observed with the parental isolate. Strains 2019wecA (panel E) and 2019siaB (panel F) do not form detectable biofilms in the chinchilla middle ear. A similarly stained naive bulla is presented in panel G.

Figure 9:
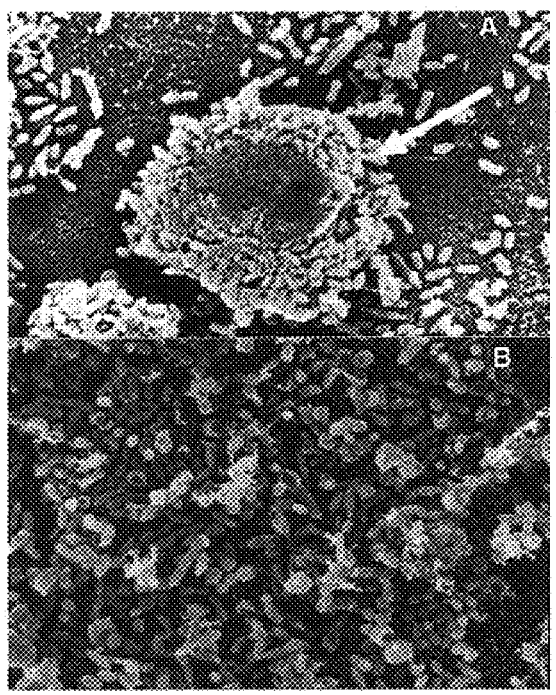

FIG. 9. SEM images of parent strain 2019 (panel A) and strain 2019wecA (panel B) grown for 3 days on primary human bronchus cells. The parent strain forms organized microcolonies of bacteria while the mutant strain grows primarily as a monolayer of individual bacteria.

Figure 10:
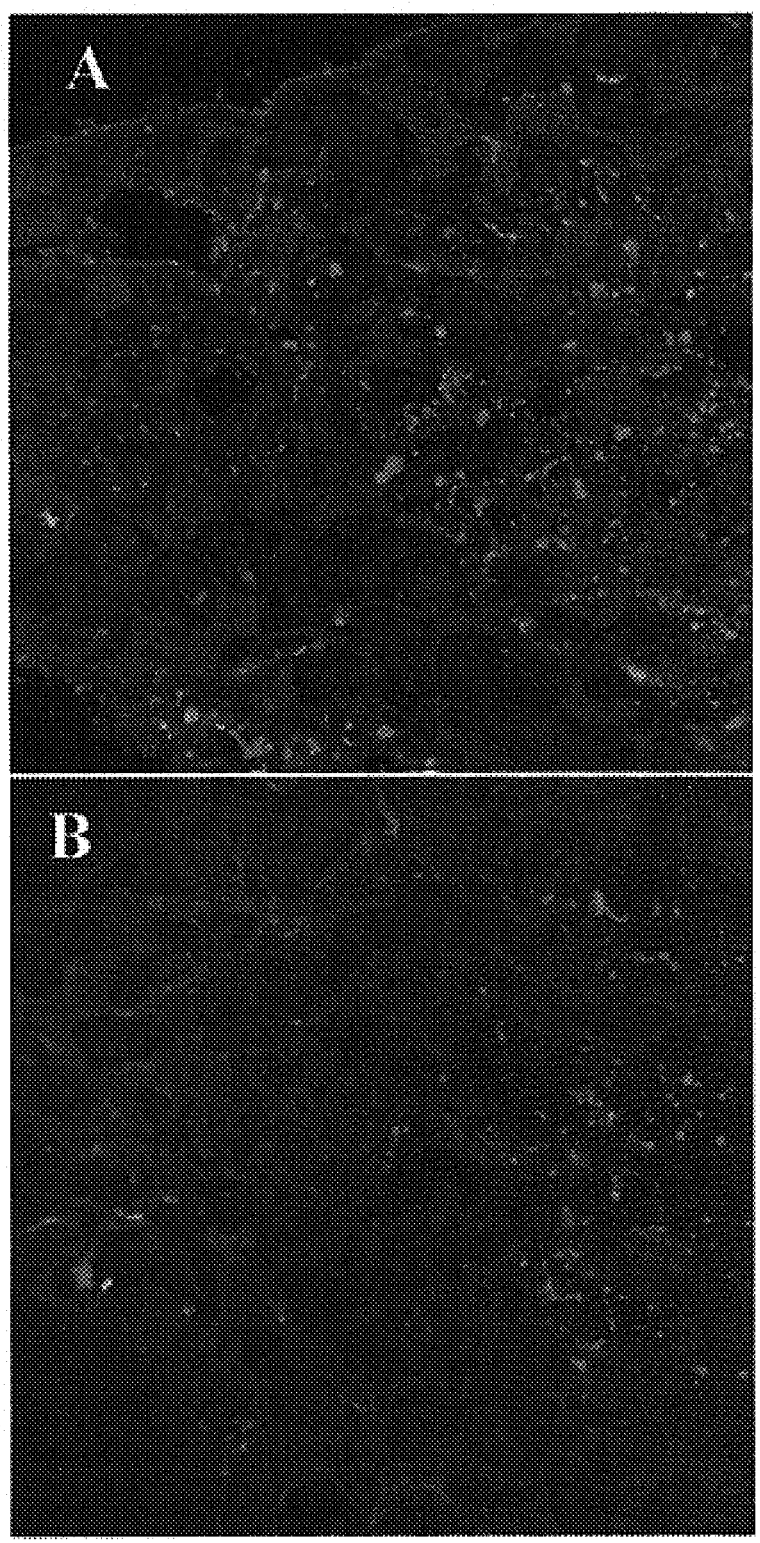

FIG. 10. Composite of confocal images obtained following incubation of an OCT-embedded biofilm produced by strain 2019 in the chinchilla middle ear with fluorochrome-conjugated lectins. Panel A—Binding of the lectin *Sambucus nigra* (SNA-TRITC) is shown in red. The specificity of this lectin is to sialic acid α-2-6 galactose and in these images is shown binding to the biofilm matrix. *Macchia amurensia* lectin (MAA-FITC in green), which has specificity for sialic acid α-2-3 galactose and lactose, binds to the LOS of the NTHi present within the biofilm. Panel B—Lectin labeling obtained after neuraminidase treatment of a serial section of the same OCT-embedded biofilm shown in panel A. Neuraminidase removes labeling by SNA-TRITC to the biofilm completely, confirming the presence of sialic acid in an α2-6 linkage (Brinkman-Van der Linden et al., (2002) Anal Biochem 303, 98-104). There is minimal change in the binding of MAA-FITC to the organisms after neuraminidase. In addition, these sections show the infiltration of the biofilm with inflammatory cells (nuclei are labeled blue with a DNA stain (To-Pro3)).

FIG. 11. Permease Designated by TIGR as HI0147—Amino Acid Sequence (SEQ ID NO:1). This sequence is longer than that in FIG. 15, as this molecule includes a signal sequence. The signal sequence is transcribed when the protein is made, and then cleaved when it is transported form the cytoplasm to the periplasm.

FIG. 12. Permease Designated by TIGR HI0147—Nucleic Acid Sequence (SEQ ID NO:2).

Figure 13:
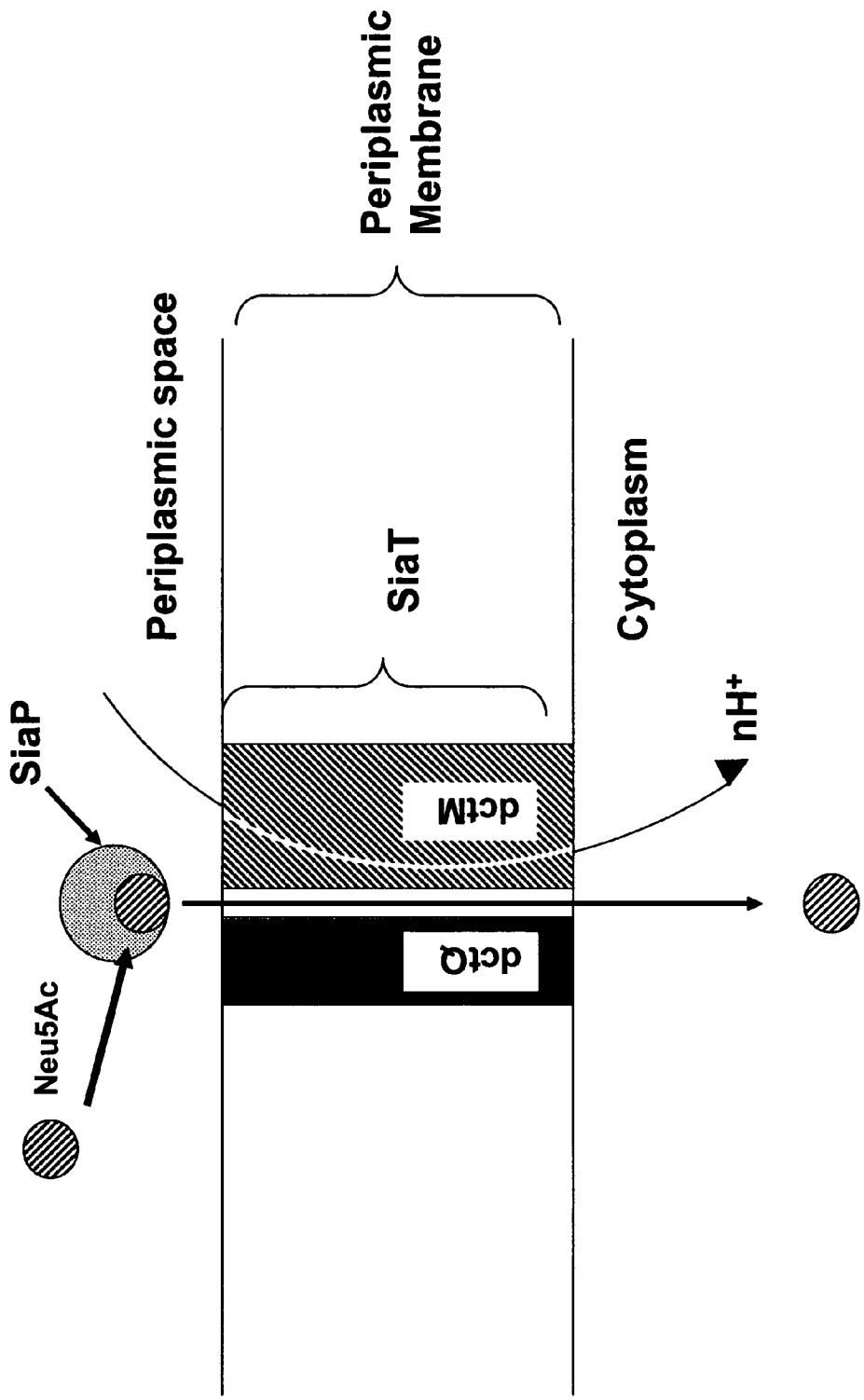

FIG. 13. Cartoon of TRAP transporter.

FIG. 14. 2019 siaT nucleic acid sequence (SEQ ID NO:9).

FIG. 15. 2019 siaT amino acid sequence (SEQ ID NO:10).

FIG. 16. 2019 siaP (Designated by TIGR HI0146) nucleic acid sequence (SEQ ID NO:11).

FIG. 17. 2019 siaP (Designated by TIGR HI0146) nucleic acid sequence (SEQ ID NO:12).

Figure 18:
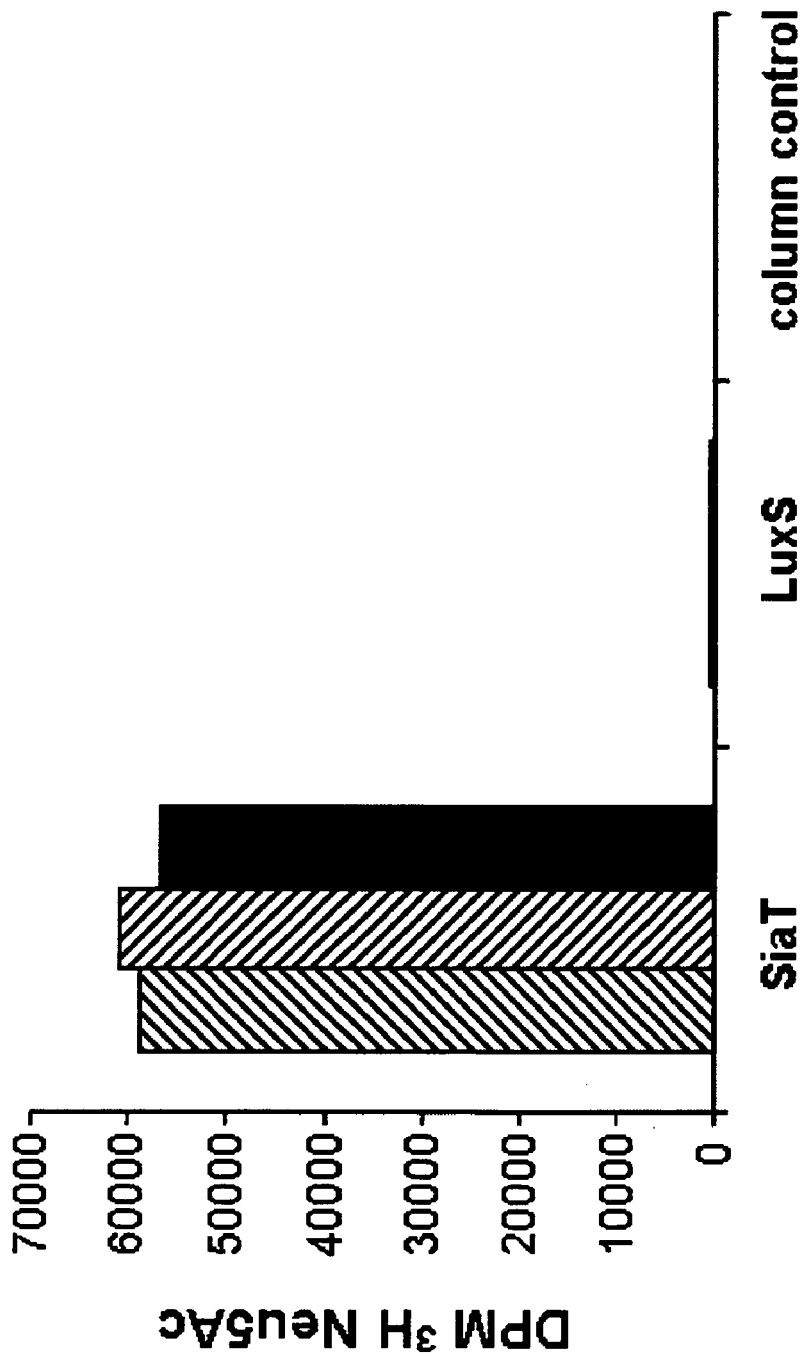

FIG. 18. Binding of $^3$H-Neu5Ac to His-tagged siaP bound to a nickel affinity resin.

Figure 19:
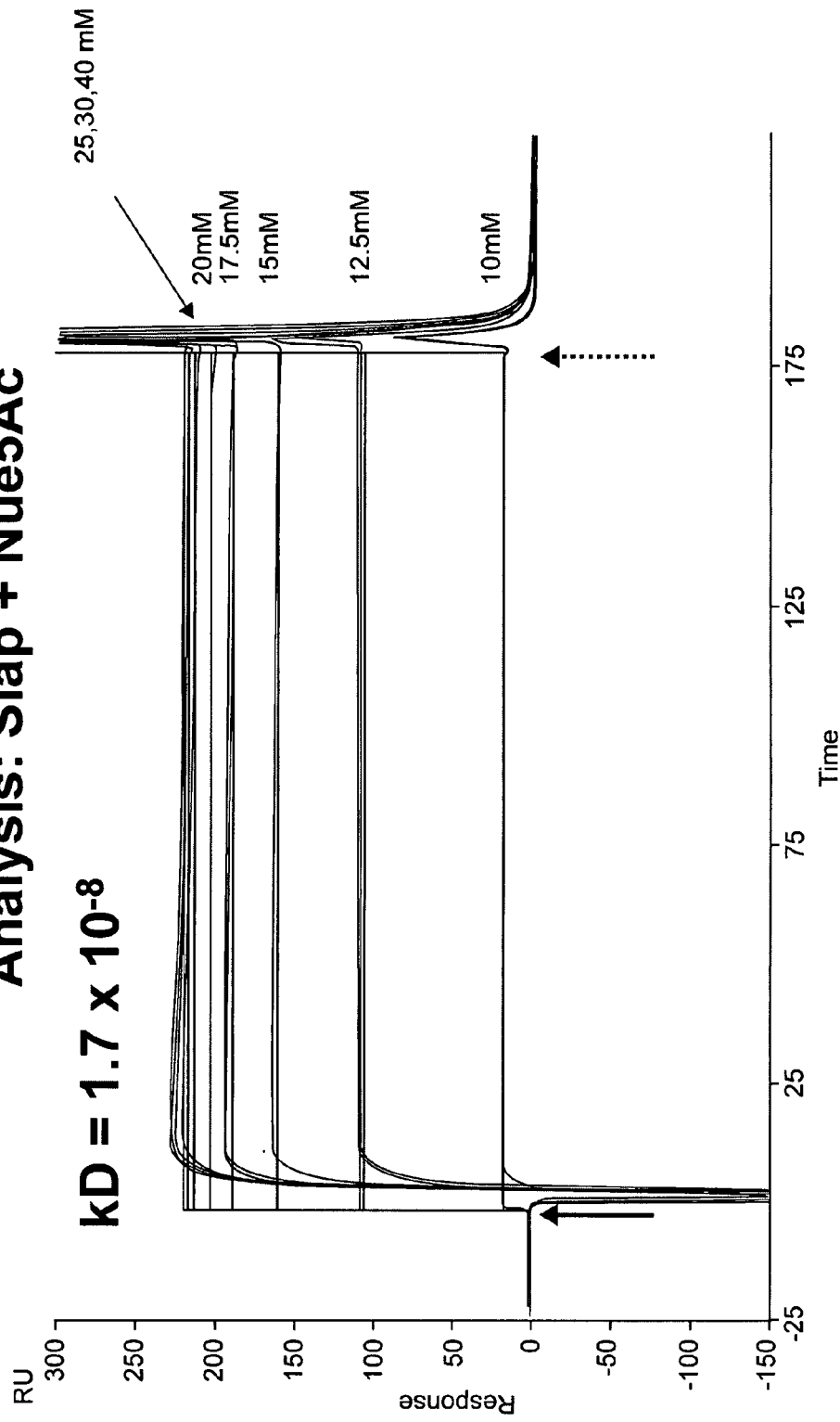

FIG. 19. SiaP binding affinity.

Figure 20:
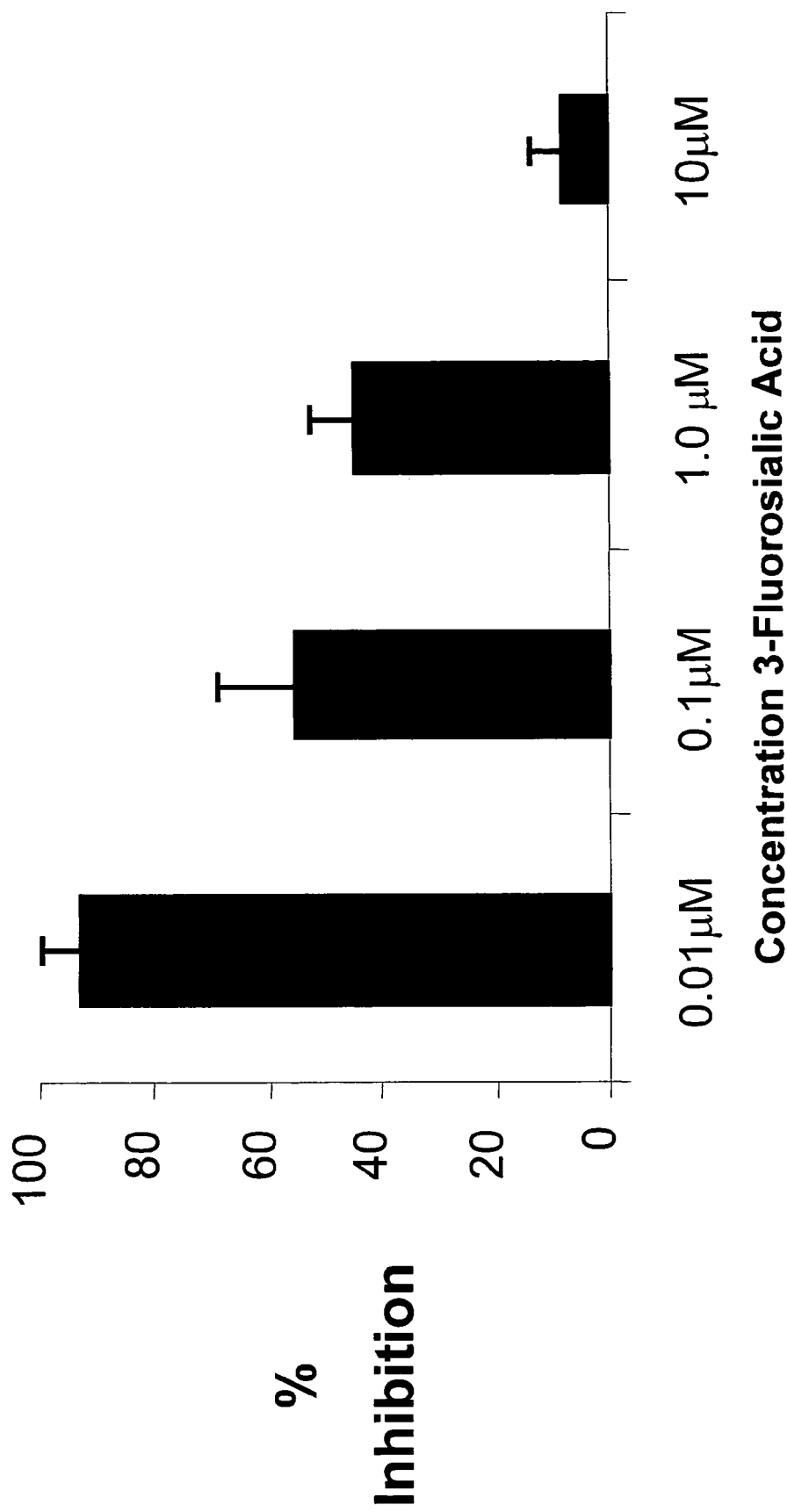

FIG. 20. Graph depicting inhibition of incorporation of sialic acid onto the surface of an organism. The error bars represent one standard deviation from the mean.

FIG. 21 provides a list of exemplary siaT proteins. It should be noted that proteins that the lower the E-value, the more similar the protein is to the test protein (*H. influenzae* siaT), and that have a E-value of "0" are identical to the test protein.

FIG. 22 provides a list of exemplary siaP proteins.

Figures 23A, 23B:
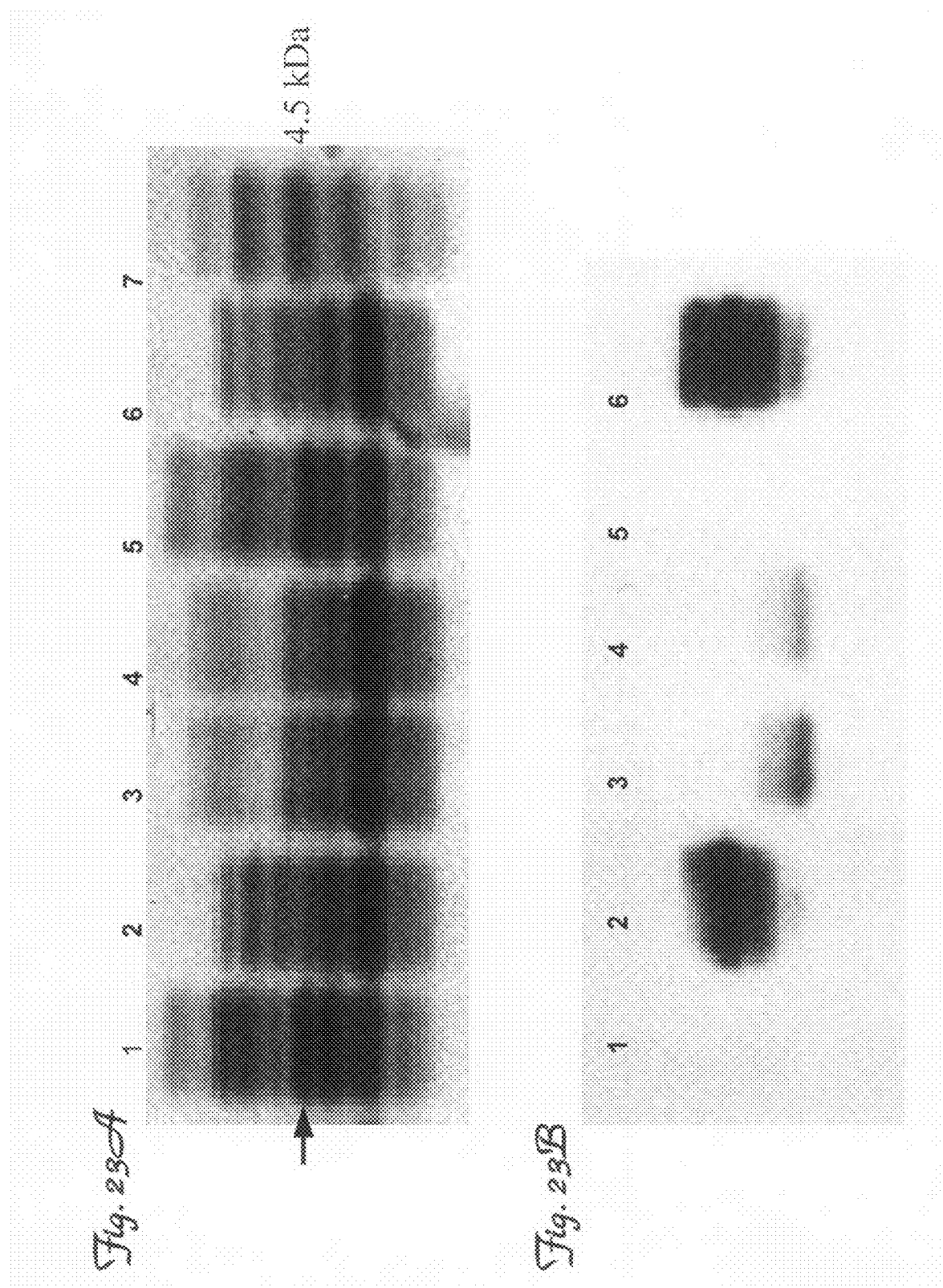

FIG. 23A provides a map of a portion of the *H. influenzae* Rd genome. FIG. 23B provides an analysis of the SiaP protein (Residues 1-70 of SEQ ID NO:12).

FIGS. 24A-D provide MALDI-TOF-MS of O-dacylated LOS.

FIGS. 25A-B provide graphs showing resistance of NTHi 2019 and 2019siaP to 10% Pooled Normal Human Serum.

Figures 26A, 26B, 26C, 26D:
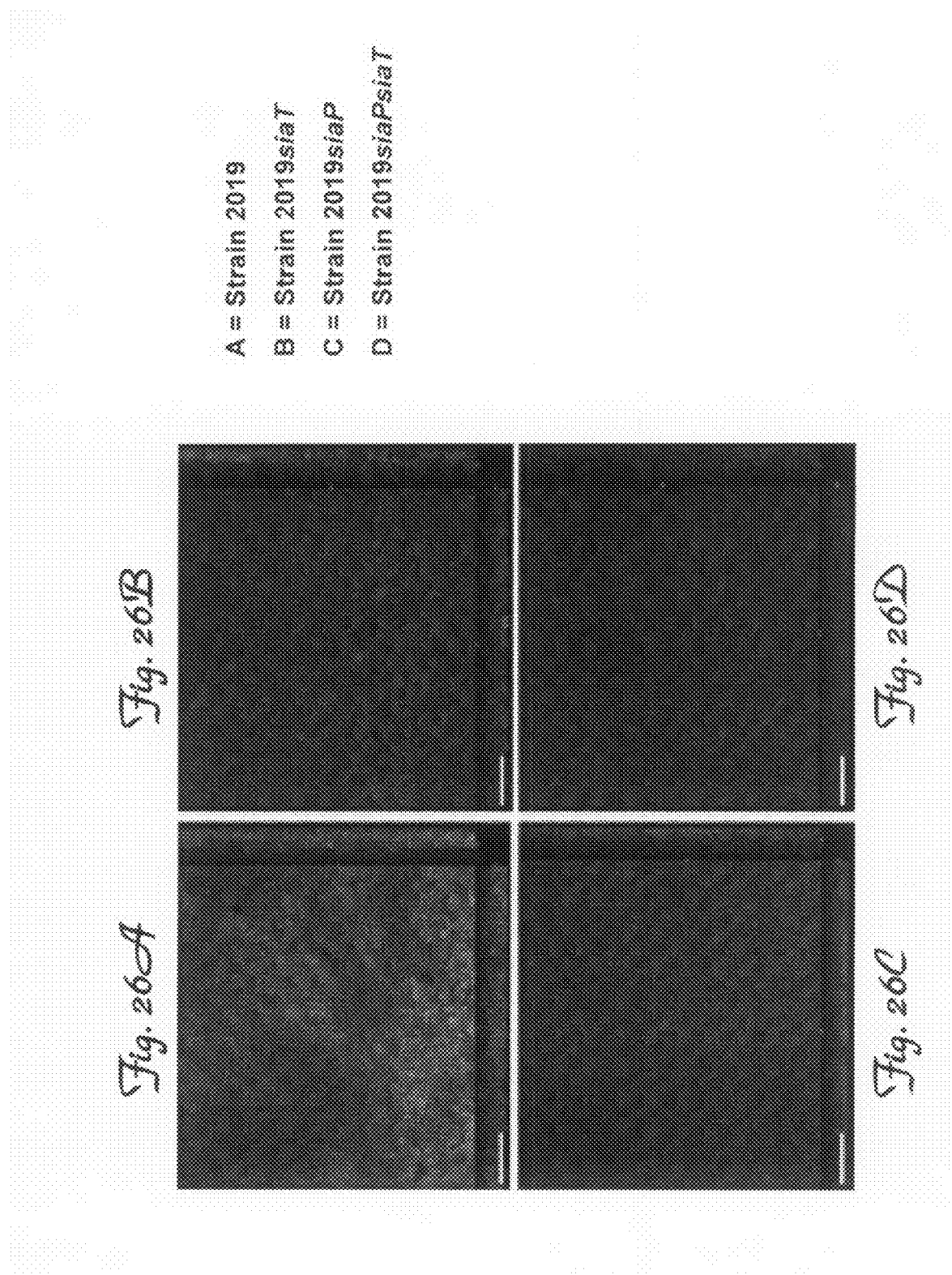

FIGS. 26A-D provide a continuous-flow assay of cells. FIG. 26A shows Strain 2019, FIG. 26B shows Strain 2019siaT, FIG. 26C shows Strain 2019sia, and FIG. 26D shows Strain 2019siaPsiaT.

Figure 27:
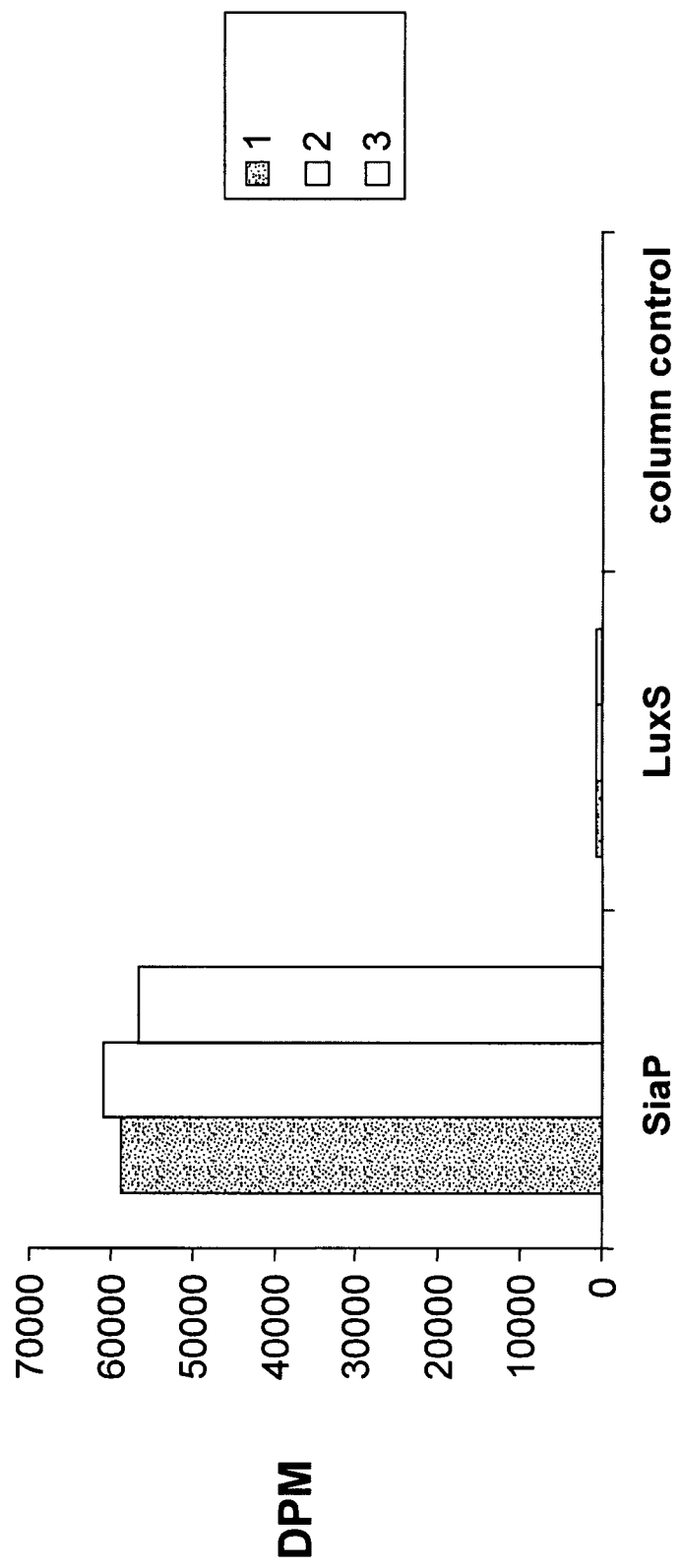

FIG. 27 provides the results of a Biacore® analysis.

Figure 28:
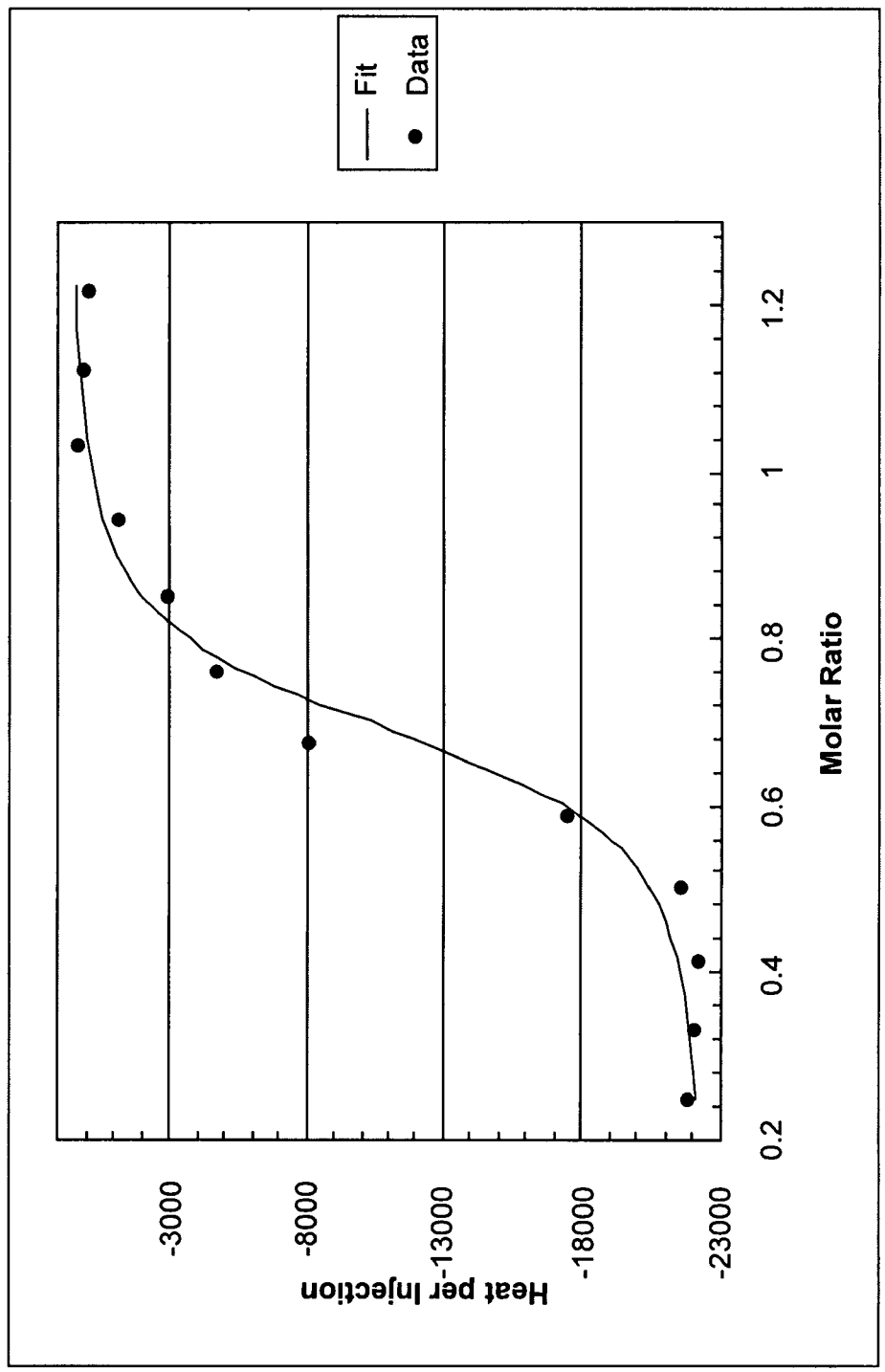

FIG. 28 shows changes in heat of binding (Y-axis) as sialic acid concentration (X-axis) increases relative to SiaP as the concentration of sialic acid increases.

DETAILED DESCRIPTION

Lipooligosaccharides (LOS) are a major component of the NTHi outer membrane and have been shown to play a role in microbial virulence and pathogenicity (Rao et al., (1999) FEMS Microbiol Rev 23, 99-129). LOS contains carbohydrate epitopes which mimic human glycosphingolipids, allowing the bacteria to avoid the host immune response (Mandrell et al., (1992) Infect Immun 60, 1322-1328). LOS present on the surface of NTHi is a heterogeneous mixture of glycoforms, the most abundant of which has been extensively studied and is known to consist of a lactose moiety (Galβ1-4Glc) attached to the first heptose (Hep$^I$) of a conserved core structure (Hep$^{III}$α1,2-Hep$^{II}$α1,3-Hep$^I$α1,5-Kdo(P)-lipid A) (Phillips et al., (1992) Biochemistry 31, 4515-4526; Schweda et al., (1993) Carbohydr Res 246, 319-330; Masoud et al., (1997) Biochemistry 36, 2091-2103). It is important to note that NTHi are also capable of incorporating the acidic sugar N-acetylneuraminic acid (Neu5Ac or sialic acid) as terminal non-reducing units into their LOS, giving the bacteria protection from complement-mediated killing by normal human serum (Hood et al., (1999) Mol Microbiol 33, 679-692; Hood et al., (2001) Mol Microbiol 39, 341-350). The acceptors for sialic acid are lactose, N-acetyllactosamine, and possibly N-acetylgalactosamine, although the precise structures of most of these sialylated LOS species have not been conclusively identified (Jones et al., (2002) J Biol Chem 277, 14598-14611).

The sialic acid is incorporated into the LOS before it reaches the cell surface by one of three sialyltransferases, SiaA, Lic3a or LsgB (Hood et al., (2001) Mol Microbiol 39, 341-350; Jones et al., (2002) J Biol Chem 277, 14598-14611). The donor for this transfer is CMP-sialic acid which is synthesized from sialic acid and CTP by the CMP-sialic acid synthetase (SiaB) (Hood et al., (1999) Mol Microbiol 33, 679-692). The fate of sialic acid in NTHi is not solely incorporation into the LOS. Sialic acid can also be utilized as a carbon and nitrogen source via its break down to N-acetylmannosamine and pyruvate by the neuraminyl lyase (NanA) (Vimr et al., (2000) Mol Microbiol 36, 1113-1123).

NTHi is incapable of synthesizing sialic acid and thus requires an exogenous source of sialic acid for incorporation to occur. In *Escherichia coli*, sialic acid is imported via symport with a proton through a specific transporter (NanT) of the major facilitator superfamily (Vimr et al., (1985) J Bacteriol 164, 845-853). A gene (HI1104) was identified in the *H. influenzae* genome that has high homology to the *E. coli* sialic acid transporter. This gene was deleted and shown to have no effect on sialic acid uptake in *H. influenzae*. Recent publications have suggested that sialic acid transport in *H. influenzae* is mediated via a novel class of transporter, a tripartite ATP-independent periplasmic (TRAP) transporter (Vimr et al., (2004) Microbiol Mol Biol Rev 68, 132-153, table of contents; Kolker et al., (2004) Nucleic Acids Res 32, 2353-2361). TRAP transporters are composed of three components: an extracellular solute receptor (ESR) and two distinct integral membrane components of unequal size which are sometimes fused (Kelly et al., (2004) Annu Rev Biochem 73, 241-268). These transporters differ from the better characterized ABC-protein transporter family (Davidson et al., (2004) Annu Rev Biochem 73, 241-268) as they do not possess an ATP-binding cassette protein and are not driven by ATP hydrolysis but rather by an electrochemical ion gradient (Kelly et al., (2004) Annu Rev Biochem 73, 241-268).

The gene HI0147 was previously identified by Rabus et al. (Rabus et al., (1999) Microbiology 145 (Pt 12), 3431-3445) as the fused transmembrane domains of a TRAP transporter and named Y147. More recently this same gene was suggested to be part of a sialic acid transporter (Vimr et al., (2004) Microbiol Mol Biol Rev 68, 132-153, table of contents; Kolker et al., (2004) Nucleic Acids Res 32, 2353-2361). The present inventors discovered that the HI0147 gene product is indeed a component of the sialic acid TRAP transporter in the NTHi strain 2019. Deletion of the gene encoding this protein has a marked effect on the incorporation of sialic acid into the LOS and, thus, the survival of the organism when exposed to human serum.

Although much of the pathway of sialic acid incorporation into lipooligosaccharides was understood, until now the transporter responsible for N-acetylneuraminic acid uptake in *H. influenzae* was yet to be characterized. In this invention, the inventors show that this transporter is a novel sugar transporter of the tripartite ATP-independent periplasmic transporter family. In the absence of this transporter, *H. influenzae* cannot incorporate N-acetylneuraminic acid into its lipooligosaccharides making the organism unable to survive when exposed to human serum.

Other *Haemophilus influenzae* strains (and other pathogens) use a similar TRAP transporter with high homology to sialic acid transport (siaT) and have sialic acid as a part of their cell wall structure. Examples include *Haemophilus influenzae*, *Haemophilus somnus*, *H gallarium*, *Vibrio vulnificus*, *Vibrio cholera*, *Shigella flexneri*, *Pseudomonas aeruginosa*, *Helicobacter pylori*, or *Pasturella multicidia*, *Salmonella enteritidis*. These pathogens can be inhibited in a similar fashion. Additional organisms that can be inhibited include the following: *Polaromonas* sp. JS666, *Oceanobacillus iheyensis* HTE831, *Sinorhizobium meliloti* 1021, *Bacillus clausii* KSM-K16, *Desulfotalea psychrophila* LSv54, *Silicibacter* sp. TM1040, *Rhodobacter sphaeroides* 2.4.1, *Pseudomonas aeruginosa* UCBPP-PA14, *Escherichia coli* CFT073, *Pseudomonas aeruginosa* PAO1, *Salmonella typhimurium* LT2, *Bordetella parapertussis* 12822, *Desulfovibrio desulfuricans* G20, *Enterococcus faecium*, *Bordetella bronchiseptica* RB50, *Bacillus clausii* KSM-K16, *Microbulbifer degradans* 2-40, *Haemophilus influenzae* R2866, *Enterococcus faecalis* V583, *Silicibacter pomeroyi* DSS-3, *Agrobacterium tumefaciens* str. C58, *Desulfotalea psychrophila* LSv54, *Dechloromonas aromatica* RCB, *Helicobacter hepaticus* ATCC 51449, *Caulobacter crescentus* CB15, *Magnetococcus* sp. MC-1, *Mannheimia succiniciproducens* MBEL55E, *Haemophilus somnus* 129PT, *Pasteurella multocida* subsp. *multocida* str. Pm70, *Escherichia coli* K12, *Rhodospirillum rubrum*, *Bacillus licheniformis* ATCC 14580 (DSM 13), *Fusobacterium nucleatum* subsp. *nucleatum* ATCC 25586,

*Azoarcus* sp. EbN1, *Salmonella enterica* subsp. *enterica serovar Typhi Ty2*, *Pseudomonas aeruginosa* UCBPP-PA14, *Azotobacter vinelandii*, *Shigella flexneri* 2a str. 301, *Salmonella enterica* subsp. *enterica serovar Paratypi A*str. ATCC 9150, *Pasteurella multocida* subsp. *multocida* str. Pm70, *Vibrio vulnificus* YJ016, *Photorhabdus luminescens* subsp. *laumondii* TTO1, *Wolinella succinogenes* DSM 1740, *Haemophilus somnus* 2336, *Burkholderia fungorum* LB400, *Shigella flexneri* 2a str. 301, *Bradyrhizobium japonicum* USDA 110, *Desulfovibrio vulgaris* subsp. *vulgaris* str. Hildenborough, *Geobacillus kaustophilus* HTA426, *Bacillus halodurans* C-125, *Vibrio cholerae* O1 biovar eltor str. N16961, *Haemophilus influenzae* 86-028NP, *Haemophilus somnus* 129PT, and *Fusobacterium nucleatum* subsp. *vincentii* ATCC 49256.

Biofilms are aggregates of one or more types of bacteria attached to a biological or inert surface and encased in a glycocalyx or matrix. The biofilm matrix has many roles. It is thought to provide protection from environmental threats including antibiotics, surfactants and host immune responses. The glycocalyx can also fuction as a scavenging system, to trap and filter nutrients and essential minerals from the environment (Dunne, (2002) Clin Microbiol Rev 15, 155-66; O'Toole et al., (2000) Annu Rev Microbiol 54, 49-79; Sutherland, (2001) Trends Microbiol 9, 222-7). This matrix is primarily comprised of bacterial exopolysaccharides, and in some cases DNA, and may contain host-derived proteins such as fibrinogen, fibronectin, and glycosaminoglycans. (Dunne, (2002) Clin Microbiol Rev 15, 155-66; O'Toole et al., (2000) Annu Rev Microbiol 54, 49-79; Sutherland, (2001) Trends Microbiol 9, 222-7; Wozniak et al., (2003) PNAS 100, 7907-12).

As discussed above, NTHi is an opportunistic pathogen that normally resides exclusively in the human nasopharynx as a commensal. NTHi can however cause acute otitis media (OM) and other respiratory tract illnesses, and are the predominant pathogen in chronic OM. NTHi forms biofilms in vitro (Murphy et al., (2002) BMC Microbiol 2, 7; Rayner et al., (1998) Jama 279, 296-9) and in vivo (Rayner et al., (1998) Jama 279, 296-9; Post (2001) Laryngoscope 111, 2083-94). Using a chinchilla model, Erhlich et al. (Ehrlich et al., (2002) Jama 287, 1710-5) showed that biofilms formed in animals inoculated with NTHi from 1 to 21 days after challenge. Fluorescent vital staining and confocal scanning laser microscopy (CSLM) demonstrated that bacteria within the biofilms were viable. Collectively, these findings provide evidence that mucosal biofilms form in an experimental model of OM and suggest that biofilm formation may be an important factor in the pathogenesis of chronic OM. Studies indicated that genes involved in complex carbohydrate biosynthesis are involved in biofilm formation in vitro (Greiner et al., (2004) Infect. Immun 72, 4249-60). To confirm that these same pathways are operative in biofilm formation in vivo, the ability of NTHi strain 2019 and five isogenic mutants to form biofilms was investigated in a chinchilla model. The role of SiaA, SiaB, Pgm, LsgB, and WecA in NTHi biofilm formation in vivo was determined.

Sialic Acid Permease System

Host-derived sialic acid is incorporated into *Haemophilus influenzae* lipopolysaccharide and is a major virulence factor in otitis media. Bouchet et al., (2003) PNAS 100, 8898-8903. The present inventors have discovered that an enzyme, a sialic acid permease (also called a transporter), is necessary for the survival of certain pathogenic organisms when colonizing a host. This sialic acid permease was not previously isolated or identified. They have further shown that one can treat mammal infected with a pathogenic bacterium by administering a bacterial sialic acid permease inhibitory agent, wherein the inhibitor is administered in an amount that reduces the uptake of sialic acid by the bacterium.

Sialic acid permeases of the invention can be isolated from various strains of bacteria for example, from *Haemophilus influenzae*, *Haemophilus somnus*, *H. gallarium*, *Vibrio vulnificus*, *Vibrio cholera*, *Shigella flexneri*, *Pseudomonas aeruginosa*, *Helicobacter pylori*, or *Pasturella multicidia*, *Salmonella enteritidis*. In addition to the methods described herein, those of skill in the art of molecular biology generally know methods for isolating sialic acid permeases of the invention, for example, see Sambrook and Russell (2001), incorporated herein by reference. One embodiment is a sialic acid permease, siaT, isolated from *H. influenzae* designated by TIGR as HI0147 (SEQ ID NO:1), shown in FIG. 11. Another embodiment is 2019 siaT (SEQ ID NO:10), shown in FIG. 15. An embodiment of a siaP sialic acid permease is shown in FIG. 17 (SEQ ID NO:12).

A "sialic acid permease" of the invention is a protein involved in the sugar transportation of the tripartite ATP-independent periplasmic transporter family, and/or is a binding protein involved in the sialic acid permease system. In the absence of a transporter, the bacteria cannot incorporate N-acetylneuraminic acid into their lipooligosaccharides making the organisms unable to survive when exposed to human serum. The nucleotides that encode one *H. influenzae* sialic acid permease, siaT, are shown in FIG. 12 (SEQ ID NO:2) and in FIG. 14 (SEQ ID NO:9). FIG. 21 provides a list of exemplary siaT proteins. The nucleotides that encode on *H. influenzae* sialic acid permease binding protein, siaP, are shown in FIG. 16 (SEQ ID NO: 10). Sialic acid permease can be isolated using techniques known to the art. FIG. 22 provides a list of exemplary siaP proteins.

As used herein, the term "nucleic acid" refers deoxyribonucleotides or ribonucleotides and polymers thereof in either single- or double-stranded form, composed of monomers (nucleotides) containing a sugar, phosphate and a base that is either a purine or pyrimidine. The terms "nucleic acid," "nucleic acid molecule," "nucleic acid fragment," "nucleic acid sequence or segment," or "polynucleotide" may also be used interchangeably with gene, cDNA, DNA and RNA encoded by a gene, e.g., genomic DNA, and even synthetic DNA sequences. The term also includes sequences that include any of the known base analogs of DNA and RNA.

The invention encompasses isolated or substantially purified nucleic acid or protein compositions (the terms "protein," "peptide" and "polypeptide" are used interchangeably herein). In the context of the present invention, an "isolated" or "purified" DNA molecule or an "isolated" or "purified" polypeptide is a DNA molecule or polypeptide that exists apart from its native environment and is therefore not a product of nature. An isolated DNA molecule or polypeptide may exist in a purified form or may exist in a non-native environment such as, for example, a transgenic host cell.

"Recombinant" polypeptides refer to polypeptides produced by recombinant DNA techniques, i.e., produced from cells transformed by an exogenous DNA construct encoding the desired polypeptide. "Synthetic" polypeptides are those prepared by chemical synthesis. "Recombinant DNA molecule" is a combination of DNA sequences that are joined together using recombinant DNA technology and procedures used to join together DNA sequences as described (for example, as in Sambrook and Russell, 2001).

The term "gene" is used broadly to refer to any segment of nucleic acid associated with a biological function. Thus, genes include coding sequences and/or the regulatory sequences required for their expression.

"Naturally occurring," "native" or "wild type" is used to describe an object that can be found in nature as distinct from being artificially produced. Furthermore, "wild-type" refers to the native gene without any known mutation. "Native" or "wild type" proteins, polypeptides or peptides are proteins, polypeptides or peptides isolated from the source in which the proteins naturally occur.

"Expression cassette" as used herein means a DNA sequence capable of directing expression of a particular nucleotide sequence in an appropriate host cell or production cell, comprising a promoter operably linked to the nucleotide sequence of interest which is operably linked to termination signals. It also typically includes sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. The expression of the nucleotide sequence in the expression cassette may be under the control of a constitutive promoter or of an inducible promoter that initiates transcription only when the host cell is exposed to some particular external stimulus. In the case of a multicellular organism, the promoter can also be specific to a particular tissue or organ or stage of development.

Such expression cassettes may include the transcriptional initiation region of the invention linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

The transcriptional cassette may include in the 5'-3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source.

The terms "heterologous DNA sequence," "exogenous DNA segment" or "heterologous nucleic acid," each refer to a sequence that originates from a source foreign to the particular host cell or, if from the same source, is modified from its original form. Thus, a heterologous gene in a host cell includes a gene that is endogenous to the particular host cell but has been modified. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

A "homologous" DNA sequence is a DNA sequence that is naturally associated with a host cell into which it is introduced.

A "vector" is a replicon, such as a plasmid, phage, virus, or cosmid, to which another DNA segment may be attached so as to bring about the replication of the attached segment. A "vector" is defined to include, inter alia, any plasmid, cosmid, phage or binary vector in double or single stranded linear or circular form which may or may not be self transmissible or mobilizable, and which can transform prokaryotic or eukaryotic host either by integration into the cellular genome or exist extrachromosomally (e.g., autonomous replicating plasmid with an origin of replication).

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

The term "regulatory sequence" is art-recognized and intended to include promoters, enhancers and other expression control elements (e.g., polyadenylation signals). Such regulatory sequences are known to those skilled in the art and are described in Goeddel, Gene Expression Technology: Methods in Enzymology, 185, Academic Press, San Diego, Calif. (1990). It should be understood that the design of the expression vector may depend on such factors as the choice of the host cell to be transfected and/or the amount of fusion protein to be expressed.

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions.

"Operably-linked" refers to the association of nucleic acid sequences on single nucleic acid fragment so that the function of one is affected by the other, e.g., an arrangement of elements wherein the components so described are configured so as to perform their usual function. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. Control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence.

"Expression" refers to the transcription and/or translation of an endogenous gene or a transgene in cells. Expression may also refer to the production of protein.

As used herein, the sialic acid permease proteins include variants or biologically active fragments of the proteins. A "variant" of the protein is a protein that is not completely identical to a native protein. A variant protein can be obtained by altering the amino acid sequence by insertion, deletion or substitution of one or more amino acid. The amino acid sequence of the protein is modified, for example by substitution, to create a polypeptide having substantially the same or improved qualities as compared to the native polypeptide. The substitution may be a conserved substitution. A "conserved substitution" is a substitution of an amino acid with another amino acid having a similar side chain. A conserved substitution would be a substitution with an amino acid that makes the smallest change possible in the charge of the amino acid or size of the side chain of the amino acid (alternatively, in the size, charge or kind of chemical group within the side chain) such that the overall polypeptide retains its spatial conformation but has altered biological activity. For example, common conserved changes might be Asp to Glu, Asn or Gln; His to Lys or Arg or Phe; Asn to Gln, Asp or Glu and Ser to Cys, Thr or Gly. Alanine is commonly used to substitute for other amino acids in mutagenesis studies. The 20 essential amino acids can be grouped as follows: alanine, valine, leucine, isoleucine, proline, phenylalanine, tryptophan and methionine having nonpolar side chains; glycine, serine, threonine, cysteine, tyrosine, asparagine and glutamine having uncharged polar side chains; aspartate and glutamate having acidic side chains; and lysine, arginine, and histidine having basic side chains (Stryer (1981); Lehninger (1975)).

It is known that variant polypeptides can be obtained based on substituting certain amino acids for other amino acids in the polypeptide structure in order to modify or improve biological activity. For example, through substitution of alternative amino acids, small conformational changes may be conferred upon a polypeptide that result in increased bioactivity.

One can use the hydropathic index of amino acids in conferring interactive biological function on a polypeptide, wherein it is found that certain amino acids may be substituted for other amino acids having similar hydropathic indices and still retain a similar biological activity.

The amino acid sequence of the variant sialic acid permease protein corresponds essentially to the native protein amino acid sequence. As used herein "corresponds essentially to" refers to a polypeptide sequence that will elicit a biological response substantially the same as the response generated by native protein. Such a response may be at least 60% of the level generated by native protein, and may even be at least 80%, 85%, 90% or 95% of the level generated by native protein. For example, variants of the native enzyme will elicit a biological response (i.e., transport of sialic acid) substantially the same as the response generated by the native enzyme.

A variant of the invention may include amino acid residues not present in the corresponding native protein, or may include deletions relative to the corresponding native protein. A variant may also be a truncated fragment as compared to the corresponding native protein, i.e., only a portion of a full-length protein. Protein variants also include peptides having at least one D-amino acid.

The sialic acid permease of the present invention may be expressed from isolated nucleic acid (DNA or RNA) sequences encoding the proteins. Amino acid changes from the native to the variant protein may be achieved by changing the codons of the corresponding nucleic acid sequence. Recombinant is defined as a peptide or nucleic acid produced by the processes of genetic engineering. It should be noted that it is well-known in the art that, due to the redundancy in the genetic code, individual nucleotides can be readily exchanged in a codon, and still result in an identical amino acid sequence.

The starting material (such as a coding sequence for sialic acid permease) used to make the complexes of the present invention may be substantially identical to wild-type genes, or may be variants of the wild-type gene. Further, the polypeptide encoded by the starting material may be substantially identical to that encoded by the wild-type gene, or may be a variant of the wild-type gene. The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full length cDNA or gene sequence, or the complete cDNA or gene sequence.

(b) As used herein, "comparison window" makes reference to a contiguous and specified segment of a polynucleotide sequence, wherein the polynucleotide sequence in the comparison window may include additions or deletions (i.e., gaps) compared to the reference sequence (which does not include additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Preferred, non-limiting examples of such mathematical algorithms are the algorithm of Myers and Miller (1988); the local homology algorithm of Smith et al. (1981); the homology alignment algorithm of Needleman and Wunsch (1970); the search-for-similarity-method of Pearson and Lipman (1988); the algorithm of Karlin and Altschul (1990), modified as in Karlin and Altschul (1993).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT™, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988); Higgins et al. (1989); Corpet et al. (1988); Huang et al. (1992); and Pearson et al. (1994). The ALIGN program is based on the algorithm of Myers and Miller, supra. The BLAST programs of Altschul et al. (1990); Altschul et al. (1997), are based on the algorithm of Karlin and Altschul supra.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, less than about 0.01, or even less than about 0.001.

To obtain gapped alignments for comparison purposes, Gapped BLAST (in BLAST 2.0) can be utilized as described in Altschul et al. (1997). Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g. BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. Alignment may also be performed manually by inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may include additions or deletions (i.e., gaps) as compared to the reference sequence (which does not include additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide includes a sequence that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, or 94%, 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, at least 80%, 90%, or even at least 95%.

Another indication that nucleotide sequences are substantially identical is if two molecules hybridize to each other under stringent conditions (see below). Generally, stringent conditions are selected to be about 5EC lower than the thermal melting point ($T_m$) for the specific sequence at a defined ionic strength and pH. However, stringent conditions encompass temperatures in the range of about 1EC to about 20EC, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide includes a sequence with at least 70%, 71%, 72%, 73%, 74%, 75%, 76%, 77%, 78%, or 79%, 80%, 81%, 82%, 83%, 84%, 85%, 86%, 87%, 88%, 89%, 90%, 91%, 92%, 93%, or 94%, or even 95%, 96%, 97%, 98% or 99%, sequence identity to the reference sequence over a specified comparison window. Optimal alignment may be conducted using the homology alignment algorithm of Needleman and Wunsch (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. Bind(s) substantially refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The $T_m$ is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl (1984); $T_m$ 81.5° C.+16.6 (log M)+0.41 (% GC)−0.61 (% form)−500/L; where M is the molarity of monovalent cations, %GC is the percentage of guanosine and cytosine nucleotides in the DNA, % form is the percentage of formamide in the hybridization solution, and L is the length of the hybrid in base pairs. $T_m$ is reduced by about 1EC for each 1% of mismatching; thus, $T_m$, hybridization, and/or wash conditions can be adjusted to hybridize to sequences of the desired identity. For example, if sequences with >90% identity are sought, the $T_m$ can be decreased 10EC. Generally, stringent conditions are selected to be about 5EC lower than the thermal melting point ($T_m$) for the specific sequence and its complement at a defined ionic strength and pH. However, severely stringent conditions can utilize a hybridization and/or wash at 1, 2, 3, or 4EC lower than the thermal melting point ($T_m$); moderately stringent conditions can utilize a hybridization and/or wash at 6, 7, 8, 9, or 10EC lower than the thermal melting point ($T_m$); low stringency conditions can utilize a hybridization and/or wash at 11, 12, 13, 14, 15, or 20EC lower than the thermal melting point ($T_m$). Using the equation, hybridization and wash compositions, and desired T, those of ordinary skill will understand that variations in the stringency of hybridization and/or wash solutions are inherently described. If the desired degree of mismatching results in a T of less than 45EC (aqueous solution) or 32EC (formamide solution), the SSC concentration can be increased so that a higher temperature can be used. An extensive guide to the hybridization of nucleic acids is found in Tijssen (1993). Generally, highly stringent hybridization and wash conditions are selected to be about 5° C. lower than the thermal melting point ($T_m$) for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see Sambrook et al. (2001) for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids that have more than 100 complementary residues on a filter in a Southern or Northern blot is 50% formamide, e.g., hybridization in 50% formamide, 1 M NaCl, 1% SDS at 37EC, and a wash in 0.1×SSC at 60 to 65EC. Exemplary low stringency conditions include hybridization with a buffer solution of 30 to 35% formamide, 1M NaCl, 1% SDS (sodium dodecyl sulphate) at 37EC, and a wash in 1× to 2×SSC (20×SSC=3.0 M NaCl/0.3 M trisodium citrate) at 50 to 55EC. Exemplary moderate stringency conditions include hybridization in 40 to 45% formamide, 1.0 M NaCl, 1% SDS at 37EC, and a wash in 0.5× to 1×SSC at 55 to 60EC.

Permease Inhibitors

Exemplary sialic acid derivatives that inhibit this novel sialic acid permease (also called a "transporter") include the known class of viral neuraminidase (or sialidases) inhibitors (e.g., 3-fluoro-N-acetylneuraminic acid (3FNA or "3-fluoro-sialic acid"), N-acetyl-2,3-didehydro-2-deoxyneuraminic acid (DDNA), the 4-guanidino-derivative of DDNA (Relenza®) or Tamiflu®), the N-alkanoyl-derivatives of sialic acid, and analogs of such compounds.

Viruses use neuraminidases to cleave sialic acid from host surface glycoproteins as part of their entry mechanism (Murti et al., (1986) Virology 149, 36-43). Compounds such as 3-fluoro-N-acetylneuraminic acid (3FNA) (Hagiwara et al., (1994) Carbohydr Res 263, 167-72), N-acetyl-2,3-didehydro-2-deoxyneuraminic acid (DDNA), the 4-guanidino-derivative of DDNA (Relenza®) (von Itzstein et al., (1993) Nature 363, 418-23) or Tamiflu®, have all been shown to be potent and specific inhibitors of influenza A neuraminidase. Although there is no known sialidase component to the sialic acid pathway in *H. influenzae*, the inventors found that 3FNA is highly effective in inhibiting the sialylation of LOS. Similarly, the inventors have shown that the 5-N-octanoyl derivative of sialic acid (SiaOct) is also an inhibitor of LOS sialylation (Goon et al., (2002) PNAS 100, 3089-3094. At this point, the site or mechanism of action of 3FNA or SiaOct is not precisely know, although preliminary data in the related pathogen *H. ducreyi* suggest that they act at both CMP-NeuAc synthetase and the sialic acid transporter.

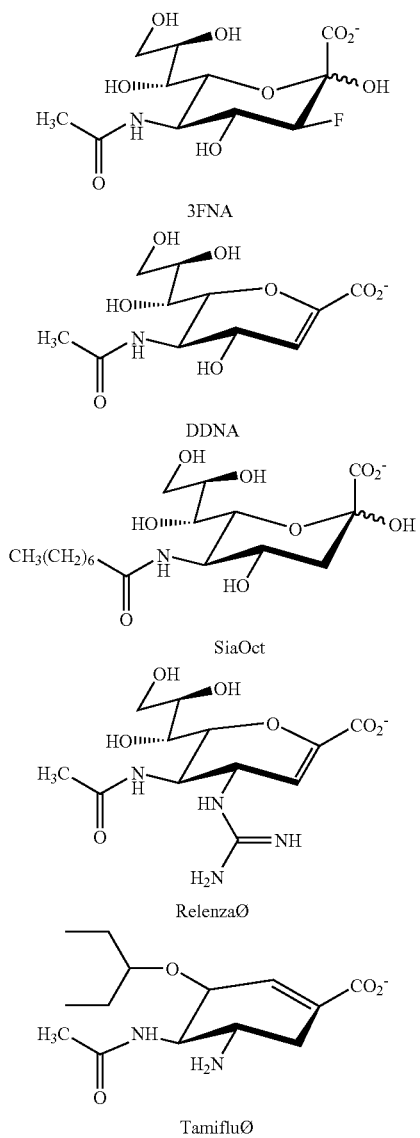

In order to generate libraries of sialic acid analogs or derivatives to screen for binding to components of the TRAP transporter (in the case of *H. influenzae*, HI0146 and HI0147), one could employ one of several methods in the literature for their synthesis. For example, Bertozzi and colleagues (Goon et al., (2003) Proc Natl Acad Sci USA 100(6): 3089-94) described an approach to make N-alkanoyl derivatives of sialic acid that were used as biosynthetic precursors in bacteria as shown in the reaction below. A series of symmetric anhydrides first react with mannosamine, and are then converted into their final N-alkanoyl sialic acid derivatives by enzymatic conversion with N-acetylneuraminic acid aldolase (NANA aldolase).

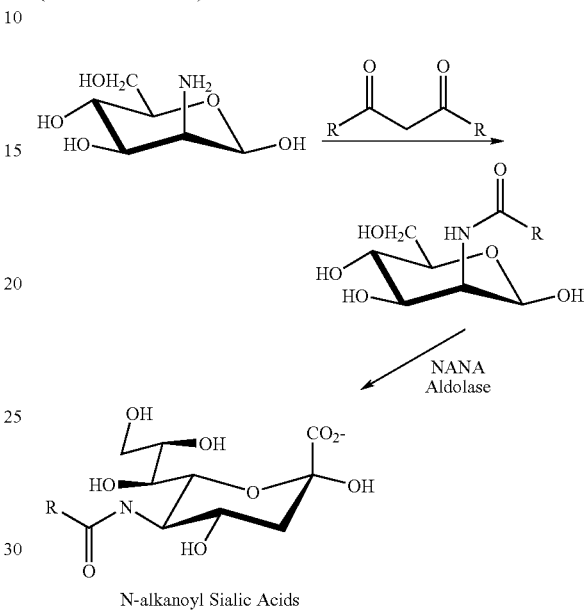

Alternatively, Lins and colleagues (Lins et al., (2002) Angew Chem Int Ed Engl 41(18): 3405-7) describe a dynamic combinatorial approach to generate a library of sialic acid analogs that start with N-acetylmannosamine or other sugar acceptors and conjugate with excess sodium pyruvate in the presence of NANA aldolase. Here, they can generate a combinatorial library where R1 and R2 are varied in a mixture of sugar acceptors and dynamically amplify for products that selectively bind a protein (also in the mixture) that has an affinity for sialic acid. This amplification is possible because this reaction is in equilibrium and the sialic acid binding protein would selectively remove the sialic acid analogs that bind to it, thus amplifying these products. In the present application, one would use components of the TRAP transporter (HI0146 or HI0147) as the protein that would bind the sialic acid analogs.

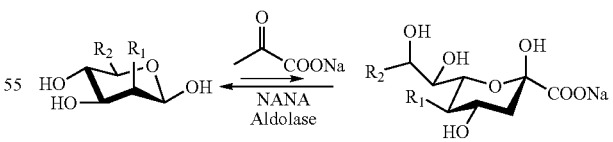

Formulations and Administration

Methods of using the inhibitory agents of sialic acid permeases in vitro or in vivo are provided. Methods using these inhibitory agents are useful, e.g., as antibiotics. Inhibitory agents of sialic acid permeases, including salts of the inhibitory agents, can be administered to a patient. Administration in accordance with the present invention may be in a single dose, in multiple doses, and/or in a continuous or intermittent manner, depending, for example, upon the recipient's physiological condition, whether the purpose of the administration is therapeutic or prophylactic, and other factors known to skilled practitioners. The administration may be essentially continuous over a preselected period of time or may be in a series of spaced doses. The amount administered will vary depending on various factors including, but not limited to, the condition to be treated and the weight, physical condition, health, and age of the patient. A clinician employing animal models or other test systems that are available in the art can determine such factors. The inhibitory agents may be administered either singly, or in combination.

One or more suitable unit dosage forms including the inhibitory agent can be administered by a variety of routes including topical, oral, parenteral (including subcutaneous, intravenous, intramuscular and intraperitoneal), rectal, dermal, transdermal, intrathoracic, intrapulmonary and intranasal (respiratory) routes.

The formulations may, where appropriate, be conveniently presented in discrete unit dosage forms and may be prepared by any of the methods known to the pharmaceutical arts. Such methods include the step of mixing the inhibitory agent with liquid carriers, solid matrices, semi-solid carriers, finely divided solid carriers or combinations thereof, and then, if necessary, introducing or shaping the product into the desired delivery system. By "pharmaceutically acceptable" it is meant a carrier, diluent, excipient, and/or salt that is compatible with the other ingredients of the formulation, and not deleterious or unsuitably harmful to the recipient thereof. The therapeutic compounds may also be formulated for sustained release, for example, using microencapsulation (see WO 94/07529, and U.S. Pat. No. 4,962,091).

The inhibitory agent may be formulated for parenteral administration (e.g., by injection, for example, bolus injection or continuous infusion) and may be presented in unit dose form in ampoules, pre-filled syringes, and small volume infusion containers, or in multi-dose containers. Preservatives can be added to help maintain the shelve life of the dosage form. The inhibitory agent and other ingredients may form suspensions, solutions, or emulsions in oily or aqueous vehicles, and may contain formulatory agents such as suspending, stabilizing and/or dispersing agents. Alternatively, the inhibitory agent and other ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable carriers and vehicles that are available in the art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol®," polyglycols and polyethylene glycols, $C_1$-$C_4$ alkyl esters of short-chain acids, ethyl or isopropyl lactate, fatty acid triglycerides such as the products marketed under the name "Miglyol®," isopropyl myristate, animal, mineral and vegetable oils and polysiloxanes.

It is possible to add other ingredients such as antioxidants, surfactants, preservatives, film-forming, keratolytic or comedolytic agents, perfumes, flavorings and colorings. Antioxidants such as t-butylhydroquinone, butylated hydroxyanisole, butylated hydroxytoluene and α-tocopherol and its derivatives can be added.

The pharmaceutical formulations of the present invention may include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the carriers and/or diluents that are useful in the pharmaceutical formulations of the present invention include water and physiologically acceptable buffered saline solutions such as phosphate buffered saline solutions at a pH of about 7.0-8.0.

The inhibitory agent can also be administered via the respiratory tract. Thus, the present invention also provides aerosol pharmaceutical formulations and dosage forms for use in the methods of the invention. In general, such dosage forms include an amount of inhibitory agent effective to treat or prevent the clinical symptoms of a specific condition. Any attenuation, for example a statistically significant attenuation, of one or more symptoms of a condition that has been treated pursuant to the methods of the present invention is considered to be a treatment of such condition and is within the scope of the invention.

For administration by inhalation, the composition may take the form of a dry powder, for example, a powder mix of the inhibitory agent and a suitable powder base such as lactose or starch. The powder composition may be presented in unit dosage form in, for example, capsules or cartridges, or, e.g., gelatin or blister packs from which the powder may be administered with the aid of an inhalator, insufflator, or a metered-dose inhaler (see, for example, the pressurized metered dose inhaler (MDI) and the dry powder inhaler disclosed in Newman (1984).

The inhibitory agent may also be administered in an aqueous solution, for example, when administered in an aerosol or inhaled form. Thus, other aerosol pharmaceutical formulations may include, for example, a physiologically acceptable buffered saline solution. Dry aerosol in the form of finely divided solid compound that is not dissolved or suspended in a liquid is also useful in the practice of the present invention.

For administration to the respiratory tract, for example, the upper (nasal) or lower respiratory tract, by inhalation, the inhibitory agent can be conveniently delivered from a nebulizer or a pressurized pack or other convenient means of delivering an aerosol spray. Pressurized packs may include a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Nebulizers include, but are not limited to, those described in U.S. Pat. Nos. 4,624,251; 3,703,173; 3,561,444; and 4,635,627. Aerosol delivery systems of the type disclosed herein are available from numerous commercial sources including Fisons Corporation (Bedford, Mass.), Schering Corp. (Kenilworth, N.J.) and American Pharmoseal Co., (Valencia, Calif.). For intra-nasal administration, the therapeutic agent may also be administered via nose drops, a liquid spray, such as via a plastic bottle atomizer or metered-dose inhaler. Typical of atomizers are the Mistometer™ (Wintrop) and the Medihaler® (Riker). The inhibitory agent may also be delivered via an ultrasonic delivery system. In some embodiments of the invention, the inhibitory agent may be delivered via an endotracheal tube. In some embodiments of the invention, the inhibitory agent may be delivered via a face mask.

Furthermore, the inhibitory agent may also be used in combination with other therapeutic agents, for example, pain relievers, anti-inflammatory agents, antihistamines, and the like, whether for the conditions described or some other condition.

The present invention further pertains to a packaged pharmaceutical composition such as a kit or other container. The kit or container holds a therapeutically effective amount of a pharmaceutical composition of the inhibitory agent and instructions for using the pharmaceutical composition for treating a condition.

Method of Screening for Additional Inhibitory Agents

The sialic acid permeases of the invention can be used to identify additional inhibitors of the sialic acid permease activity. In accordance with one embodiment of this invention, sialic acid permease of the present invention is produced from a production cell by transforming the cell with a recombinant DNA molecule comprising an expression cassette that encodes the enzyme. The permease is purified from a cell culture, and is then contacted with a compound to determine if the compound inhibits or blocks the enzymatic activity of the permease, i.e., interferes or blocks sialic acid transport (SiaT) or sialic acid binding (siaP).

In one embodiment, one can use the Biacore® screening method for molecules that bind to SiaT. Briefly, one uses a Biacore® instrument to measure bimolecular binding, establish a high throughput system to search for molecules which bind to SiaT or SiaP. SiaT expressing a His tag is bound to a sensor NTA chip in the Biacore® instrument. The Biacore® instrument measures binding events on the sensor chip surface, so that the interactant attached to the surface determines the specificity of the analysis. Testing the specificity of an interaction involves simply asking whether different molecules can bind to the immobilized interactant. Binding gives an immediate change in the SPR signal, so that it is directly apparent whether an interaction takes place or not. As sample is passed over the sensor surface, the progress of binding directly reflects the rate at which the interaction occurs. Injection of sample is followed by buffer flow during which the response reflects the rate of dissociation of the complex on the surface. Kinetic rate constants for the binding and dissociation can be obtained by fitting the results to mathematical descriptions of interaction models. Binding affinities can be obtained either from rate constant measurements (the dissociation constant KD is the ratio of the rate constants kd/ka for a 1:1 interaction) or by measuring the steady state level of binding as a function of sample concentration. The rate of binding of an interactant to a given surface is a function of the interactant concentration, so that measurements with the Biacore® instrument can be used to determine concentration of a specific substance in pure solution or in complex mixtures. The selectivity, dynamic range and other assay performance characteristics are determined largely by the choice of binding molecule attached to the surface. Thus, one can rapidly screen large number of candidate molecules for binding to the SiaT and develop information about rate of binding and dissociation constants. Molecules that have a high binding affinity and dissociate poorly are examined as candidates for study of inhibition of $^3$H-sialic acid uptake by nontypeable *H. influenzae*.

In another embodiment, one can use a method for $^3$H-sialic acid uptake inhibition. Briefly, the bacteria (in this example, nontypeable *Haemophilus influenzae* (NTHi) strain 2019 is used) is grown in media, such as in RPMI supplemented with NAD and protophoryin IX, to midlog phase, $A_{600}$=0.4 to 0.6. The bacteria is pelleted, such as by centrifuging at 5000 RPM, 10 minutes, at room temperature. The bacterial pellets are resuspended to $A_{600}$=2.0 in 1.0 ml fresh RPMI supplemented as described above in 12×75 mm tubes. Air is bubbled through the suspension. The reaction mixture is made by adding the putative inhibitor at 1, 10 and 100 µM unlabeled sialic acid to 9 µM final concentration then adding the 3H-sialic acid (ART153, ARC St. Louis, Mo.), supplied at $5\times10^{-5}$ moles/L, to 1.0 µM final concentration in the bacterial suspension. Within one minute, 20.0 µl of the reaction mixture is removed to a Nuclepore membrane and aspirated through the membrane. The membrane is washed with 2 ml of PBS. Aliquots of the reaction mixture are removed at the selected time points (e.g., 1, 2, 3 minutes) and aspirated through the membrane as described above. At the end of the time points, the membranes are removed from the vacuum manifold and incorporated NTHi $^3$H-sialic acid is counted in a scintillation fluid. The results obtained with putative inhibitors are compared with a control in which the inhibitor is substituted with phosphate buffered saline.

A number of embodiments of the invention have been described. Nevertheless, it will be understood that various modifications may be made without departing from the spirit and scope of the invention. Accordingly, other embodiments are within the scope of the following claims.

EXAMPLE 1

Novel Sialic Acid Transporter of *Haemophilus influenzae*

A major component of the outer membrane of *H. influenzae*, the lipooligosaccharides, play an important role in microbial virulence and pathogenicity. N-Acetylneuraminic acid can be incorporated into the lipooligosaccharides as a terminal non-reducing sugar. Although much of the pathway of sialic acid incorporation into lipooligosaccharides is understood, the transporter responsible for N-acetylneuraminic acid uptake in *H. influenzae* has yet to be characterized. In this Example, the inventors demonstrate that this transporter is a novel sugar transporter of the tripartite ATP-independent periplasmic transporter family. In the absence of this transporter, *H. influenzae* cannot incorporate N-acetylneuraminic acid into its lipooligosaccharides making the organism unable to survive when exposed to human serum.

Materials and Methods

Bacterial growth—*Escherichia coli* was grown at 37° C. in Luria-Bertani medium with or without agar (1.5%) and supplemented with antibiotics as needed. Wild-type *H. influenzae* was grown on supplemented brain heart infusion (BHI) agar (Difco Laboratories, Detroit, Mich.) supplemented with 10 µg/ml hemin and 10 µg/ml NAD at 37° C. Erythromycin-resistant *H. influenzae* was selected on supplemented BHI agar with 5 µg of erythromycin/ml. Selection was carried out without $CO_2$. Table 1 lists the bacterial strains and plasmids used in this Example.

TABLE 1

Bacterial strains and plasmids used in this study

| Strain or plasmid | Genotype, relevant phenotype or selection marker | Source or reference |
|---|---|---|
| Strains | | |
| E. coli DH5α | F⁻ φdlacZΔM15 Δ(lacZYA-argF)U169 DeoR recA1 endA1 hsdR17($r_K^-m_K^+$) phoA supE44 λ⁻ thi-1 gyrA96 relA1 | Invitrogen |
| NTHi 2019 | clinical respiratory isolate | Campagnari* |
| NTHi 3198 | clinical respiratory isolate | Campagnari* |
| NTHi 7502 | clinical respiratory isolate | Campagnari* |
| NTHi2019::ΔHI1104 | HI1104 mutant, erythromycin | This study |
| NTHi 2019 siaT | Neu5Ac transporter mutant, erythromycin | This study |
| Plasmids | | |
| pCR2.1TOPO | TA cloning vector | Invitrogen |
| pACYC177 | plasmid cloning vector | New England Biolabs |
| p20191104 | 2146 bp amplicon in pCR2.1TOPO | This study |
| p20191104erm | Erythromycin resistance gene in 1104 ORF of P20191104 with 759 bp deletion | |
| p2019::HI0147 | 1762 amplicon in pACYC177 | This study |
| p7502::HI0147 | 1762 amplicon in pACYC177 | This study |
| p7502::HI0147erm | Erythromycin resistance gene inserted into the BsmI restriction site in HI0147 ORF | |

*Campagnari et al., Infect. Immun., 54: 843-847, 1987

Cloning and Mutagenesis of HI1104—PCR was used to amplify a 2146 bp fragment from NTHi 2019 genomic DNA containing ORF HI1104 using oligonucleotide primers (5'-TCCCCCCGGGTCATGGAAAGATACGGATGCAAAG-3' (SEQ ID NO:3) and 5'-TCCCCCCGGGTCAAAAGGCGACAAAGAGGGTGG-3' (SEQ ID NO:4)) with restriction sites for SmaI (underlined). This fragment was digested with SmaI and cloned into the SmaI site in pACYC177 (New England Biolabs, Beverly, Mass.). The sequence of the fragment was confirmed by sequencing and comparison with the H. influenzae Rd Kw-20 genome. This construct was named p20191104. The SmaI fragment of pBSLerm containing the erythromycin resistance gene (mlsR) was inserted into StyI/BsaBI digested and blunt end filled p20191104 by eliminating 759 of 1220 bp of the HI1104 2019 ORF. This plasmid was designated p20191104erm. NTHi 2019 transformed with the 2882 bp SmaI fragment of p20191104erm that was isolated away from the plasmid backbone by electrophoresis in an agarose gel. The NTHi mutant was confirmed by PCR and southern blot analysis. Cloning and Mutation of NTHi 2019siaT—A 1762 base pair DNA fragment was amplified from NTHi strains 2019, 3198 and 7502 genomic DNA using the polymerase chain reaction, and primers 147-up, 5'-TTTCCTACACGAG-CAACAAC-3' (SEQ ID NO:5) and 147-down 5'-CTACAT-TCCCTTATTCTTCATCAAAC-3' (SEQ ID NO:6). This fragment was cloned by ligation into the vector pCR2.1TOPO, and transformation of DH5alpha host bacteria using the manufacturer's protocols (Invitrogen, Carlsbad, Calif.). The sequences of the TA inserts were determined. These fragments corresponded to bases 16 to 1778 of the 1902 base pair open reading frame HI0147 from H. influenzae Rd KW-20 completed genome (see the World Wide Web at tigr-dot-org). These plasmids were named p2019HI0147, p3198HI0147 and p7502HI0147.

Only p7502HI0147 had a convenient restriction enzyme site near the center of the insert sequence. The SmaI excised erythromycin resistance cassette from pBSLerm was ligated into BsmI digested and T4 DNA polymerase filled p7502HI0147. The sequence of p7502HI0147ermF was determined to verify the correct position and orientation of the erythromycin gene. p7502HI0147ermF was digested with BstXI and the 2989 base pair fragment that contained only cloned Haemophilus DNA sequence and a small portion (17 base pairs) of the vector was isolated from an agarose gel and used to transform NTHi 2019. A 818 base pair fragment of the erythromycin resistance gene was amplified from the genomic DNA of the putative mutants using the primers pBSLerm-up, 5'-GGAGGAAAAAATAAAGAGGGT-TATAATGAACGAG-3' (SEQ ID NO:7) and pBSLerm-down, 5'-CACAAAAAATAGGTACACGAAAAA-CAAGTTAAGGG-3' (SEQ ID NO:8), while no product was amplified from the NTHi 2019 wild type genomic DNA. PCR amplification of the putative mutant genomic DNA with the 147-up and 147-down primers (described above), amplified a 2944 base pair fragment, while a 1762 base pair product was amplified from the wt genomic DNA. The difference in the sizes (1182 base pairs) is consistent with the size of the SmaI excised erythromycin resistance gene. The mutants were verified by Southern blotting using an erythromycin and HI0147 digoxigen-labeled probe for detection (Roche Diagnostics Inc., Indianapolis, Ind.). This mutant strain was designated NTHi2019siaT.

Colony Blots —NTHi 2019siaT mutants were grown on supplemented Difco Brain Heart Infusion agar containing 5.0 μg/ml of erythromycin and 100 μM sialic acid. The wild-type NTHi 2019 was grown on S-BHI containing 100 μM sialic acid. Colony lifts were performed using nitrocellulose filters (Protran, 82 mm, 0.45 μm, Schleicher & Shuell, Keene, N.H.) cut into quarters and placed on the bacterial plates in a region where individual colonies could be seen. After one minute the membranes were removed and dried overnight at room temperature. The next day the filters were blocked using two 60 minute incubations in 20 mM tris, 500 mM NaCl pH7.45, 0.5% Tween 20 (TBST) with 1.0% bovine serum albumin (TBST-BSA). The filters pieces were rinsed 5 minutes in neuraminidase buffer (50 mM sodium acetate, 154 mM sodium chloride, 9.0 mM calcium chloride, 25 mg/ml human serum albumin pH 5.6). The quarter filters were cut in half and one piece from each was incubated with light agitation overnight either in neuraminidase buffer or in neuraminidase buffer containing 0.05 u/ml neuramiidase (sialidase, Roche, Indianapolis, Ind.). The next day the filter pieces were washed three times for 10 minutes in TBS. The filter pieces were washed one time for 10 minutes in TBST-BSA, then incubated for three hours at room temperature in monoclonal antibody 3F11 diluted 1:100 in TBST-BSA. At the end of the three hours the filters were washed three times for 15 minutes in TBST. The filters were then incubated with peroxidase labeled goat anti-mouse IgM (Kirkegaard and Perry, Gaithersburg, Md.) diluted 1:10,000 in 0.5×TBST-BSA one hour at room temperature. At the end of one hour, the filter pieces were washed four times for 15 minutes in TBST. The filter pieces were incubated for five minutes in Super Signal™ West Pico (Pierce Chemical Co., Rockford, Ill.) and then exposed to film.

LOS Preparation and Neuraminidase Treatment—Organisms were grown on S-BHI solid media in the presence or absence of supplemental Neu5Ac (100 □g/ml). The organisms from ten heavily streaked plates were suspended in 25 ml of phosphate-buffered saline (PBS) and pelleted by centrifugation. They were washed once with PBS, and once with deionized water then extracted with 25 ml of phenol after both were equilibrated to 65° C. This mixture was cooled on ice for one hour and separated by low speed centrifugation. The top aqueous layer was removed and saved. The phenol layer was back extracted once with water at 65° C., cooled, centrifuged, and the second aqueous layer added to the first. The residual phenol was removed from the aqueous layer and the LOS by precipitating the LOS twice using 0.3 M sodium acetate (final concentration) and two volumes of 100% ethanol. This was put in a −80° C. freezer overnight and then centrifuged at 15,000×g for 30 minutes. To remove any contaminating lipoproteins, the LOS pellets were resuspended in 8 ml of buffer A (0.06 M Tris Base, 10 mM EDTA, 2.0% SDS, pH 6.8), and incubated in a boiling water bath for 5-10 min. The samples were allowed to cool, and proteinase K (Sigma Chemical Co., St Louis, Mo.) was added to a final concentration of 12.5 μg/ml. The samples were incubated at 37° C. for 16-24 hours. The LOS was precipitated as described above. The LOS was washed three times by precipitation, as above, with ethanol to remove any residual SDS. After the last precipitation the LOS was resuspended in water and centrifuged at 100,000×g for 75 minutes twice. The pellets were resuspended in water, frozen, and then lyophilized. The dry LOS was stored at room temperature. For SDS-PAGE analysis, LOS was resuspended at 1.0 mg/ml in water and 10 μg digested with 5 milliunits of neuraminidase in neuraminidase buffer and incubated at 37° C. for 2 hours.

SDS-PAGE, Silver Staining and Western Blotting —SD-SPAGE gels were prepared as described by Lesse et al. (Lesse et al., (1990) J Immunol Methods 126, 109-117). The gel was loaded with 3.0-5.0 μl from each LOS preparation (~100 nanogram of LOS). Silver staining was performed by the method of Tsai and Frasch (Tsai et al., (1982) Anal Biochem 119, 115-119). The Western Blot was performed by the method of Towbin (Towbin et al., (1979) Proc Natl Acad Sci USA 76, 4350-4354). The monoclonal antibody 3F11 recognizes a terminal N-acetyllactosamine structure and has been characterized previously (Yamasaki et al., (1991) Mol Immunol 28, 1233-1242). Detection of the antibody was performed using a peroxidase-labelled goat anti-mouse IgM secondary antibody (Kirkegaard and Perry Laboratories) and Super Signal™ West Pico Chemiluminescent Substrate (Pierce). LOS from *N. gonorrhoeae* strain PID2 was used as a molecular weight standard (Schneider et al, (1991) J Exp Med 174, 1601-1605).

[$^3$H]-Neu5Ac Uptake Assay—NTHi 2019 and 2019HI0147, 2019HI0147 and 2019HI1047::nanA were grown in supplemented RPMI (Greiner et al., (2004) Infect Immun 72, 4249-4260) to mid-log phase, $A_{600}$=0.4 to 0.6. The bacteria were pelleted by centrifugation at 9300×g for 1 minute, at room temperature. The bacterial pellets were resuspended to $A_{600}$=2.0 in 1.5 ml fresh supplemented RPMI in 1.5 ml microcentrifuge tubes. A ligand mixture was made by adding 9.0 μCi (4.5×10$^{-10}$ moles) of [$^3$H]-Neu5Ac (ART153, ARC St. Louis, Mo.) to 9.0 μl of 2.5 mM unlabeled Neu5Ac. The reaction mixture was made by adding 4.0 μl of ligand mixture to 1.5 ml of bacterial suspension (final concentration 3.3 μM unlabeled Neu5Ac and 0.07 μM [$^3$H]-Neu5Ac. As quickly as possible, 100 μl samples were removed to Nuclepore membranes and aspirated through the membrane. The membrane was washed with 2 ml of PBS, pH 7.4. Aliquots of the reaction mixture were removed at the selected time points (10-15 seconds, 0.5, 1, 2, 3, 4, 5, 7.5, 10, 15, 20, and 25 minutes) and aspirated through the membrane and washed as above. At the end of the time points the membranes were removed from the vacuum manifold and counted in scintillation fluid.

Preparation of O-Deacylated LOS (O-LOS) and Neuraminidase Treatment—To make the LOS more amenable for mass spectrometric analysis, O-linked fatty acids were removed from the lipid A moiety as previously described (Gibson et al., (1997) J. Am. Soc. Mass Spectrom. 8, 645-658). The highly purified LOS (~0.1 mg) was incubated in anhydrous hydrazine (50 μl; Aldrich) at 37° C. for 35 min with mixing every 10 minutes. Samples were cooled on ice prior to and after the addition of ice-cold acetone (250 μl; Aldrich), then transferred to −20° C. for 2 hours. The quenched reaction mixture was centrifuged (12,000×g) for 45 minutes at 4° C. The supernatant was removed and the pelleted O-LOS was dissolved in MilliQ $H_2O$ (50 μl) and evaporated on a speed vacuum system (Savant). To remove salts and other low molecular weight contaminants the O-LOS (~20-30 μg) was suspended on a nitrocellulose membrane (type VS, 0.025 μm; Millipore Corp.) over water for approximately 1 hour. The desalted O-LOS was removed from the membrane concentrated with a speed vacuum system, and analyzed by matrix-assisted laser desorption ionization-mass spectrometry (MALDI-MS). For removal of Neu5Ac, the O-LOS (~20-30 μg) was digested in 10 mM ammonium acetate, pH 6.0, containing immobilized neuraminidase from *Clostridium perfringens* (type VI; Sigma) for 20 hours at 30° C. with shaking. The enzyme was pelleted by centrifugation and the supernatant (~15 μl) was transferred to a nitrocellulose membrane for drop dialysis. The desialylated O-LOS was concentrated and analyzed by MALDI-TOF-MS.

MALDI-TOF-MS of O-LOS—Dowex® 50 beads (100-200 mesh, $NH_4^+$ form; Biorad) were added to a mixture containing equal volumes of dialyzed O-LOS (~2 μg/μl) and a saturated solution of 2,5 dihydroxybenzoic acid in acetone (Aldrich). Samples were spotted onto a stainless steel MALDI target and analyzed on a Voyager DESTR plus time of flight instrument (Applied Biosystems) with a $N_2$ laser (337 nm) in negative ion mode with linear optics (Gibson et al., (1997) J. Am. Soc. Mass Spectrom. 8, 645-658). The delay time was 165 ns and the grid voltage was 94% of the full acceleration voltage (20 kV). Spectra were acquired, averaged and mass calibrated with an external calibrant consisting of an equimolar mixture of angiotensin I, ACTH 18-39 and ACTH 7-38 (Bachem, Torrance, Calif.).

Bactericidal Assay—Non-typeable *H. influenzae* strain 2019 and the HI0147 mutant were grown to early log phase, $A_{600}$=0.2, in supplemented BHI broth. A 0.5 ml aliquot of each was centrifuged for one minute at 10,000 RPM, in a microfuge at room temperature. The pellet was re-suspended in 1.0 ml of phosphate buffered salt solution (PBSS) consisting of 10 mM $K_2HPO_4$, 10 mM $KH_2PO_4$, 136 mM NaCl, 5 mM KCl, 1 mM $CaCl_2$, 0.3 mM $MgCl_2 6H_2O$, 1 mM $MgSO_4 7H_2O$ and 0.01% BSA, pH7.0.

The bactericidal assay, modified from that reported by Andreoni and Densen (Andreoni et al., (1993) J Infect Dis 168, 227-231), was carried out in a 96 well plate in 200 μl final volume. Pooled normal human serum (PNHS), a 20-donor pool of serum from human volunteers who had no previous history of neisserial infections) was diluted to 10% in PBSS. A control containing PNHS heat-inactivated for 30 minutes at 56° $C_6$ was included in each experiment. Ten microliters ($1 \times 10^6$ organisms) of the re-suspended bacteria were diluted into 190 μl of PBSS and serial 1/10 dilutions made in PBSS. Twenty microliters of each dilution were spread on S-BHI with or without appropriate antibiotic selection and grown overnight at 37° C. in 5% $CO_2$. The colonies in these reactions were counted and used as the initial CFU. Ten microliters of the bacterial stock was incubated in the diluted serum for 30 minutes with shaking at 200 RPM in a 37° C. incubator (Inova 4080, New Brunswick Scientific, Edison, N.J.). Serial 1/10 dilutions of the reaction mixes were diluted into PBSS and were spread on S-BHI with or without appropriate antibiotic selection. These were grown overnight at 37° C. in 5% $CO_2$ and emerging colonies counted the next day. The resulting CFU value was that recorded after 30 minutes. Killing was assessed by comparing the number of CFU from the 30 minute serum incubation with the number of the initial CFU. Results were expressed as the $log_{10}$ change in CFU at 30 minutes compared to the initial CFU. Statistical analysis of the data from bactericidal assays was carried out using the paired t-test and analysis of variance functions found in Graphpad Prism, version 4, San Diego, Calif.

Results

Figure 1:
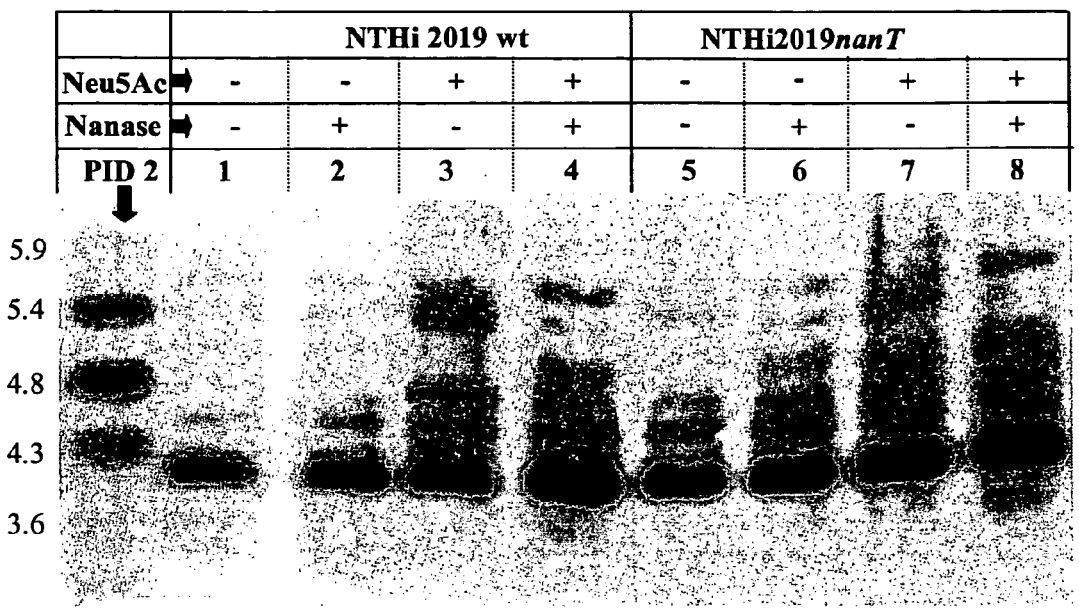
FIG. 1. SDS-PAGE of LOS isolated from NTHi 2019 wild-type and NTHi 2019HI1104. Lanes 1-4 LOS isolated from wild-type NTHi 2019, lanes 5-8 LOS isolated from the mutant NTHi 2019HI1104. Bacteria were grown on BHI in the absence (lanes 1, 2, 5 and 6) or presence (lanes 3, 4, 7 and 8) of Neu5Ac. LOS samples in lanes 2, 4, 6, and 8 were treated with neuraminidase prior to loading. LOS from *N. gonorrhoeae* strain PID2 was used as a molecular weight standard. The LOS was visualized using silver stain.

Effect of the HI1104 mutation on LOS Sialylation—Based on sequence comparison analysis of the *E. coli* database, it was assumed that HI1104 encoded a sialic acid transporter. The HI1104 ORF is predicted to encode a protein of 407 amino acids. HI1104 was deleted in the NTHi 2019 strain, the resultant strain was analyzed by SDS-PAGE and MALDI-TOF-MS. SDS-PAGE suggested there was very little difference in sialylation between mutant and wild-type LOS profiles even when the strains were grown on media supplemented with sialic acid (FIG. 1, compare lanes 1-4 with lanes 5-8). Treatment of the LOS with neuraminidase showed identical band-shifts in mutant and wild type confirming that there are sialylated glycoforms present in the HI1104 mutant (FIG. 1, compare lanes 2 and 4 with 6 and 8, respectively). The MALDI-MS profile of the O-LOS isolated from the HI1104 mutant confirmed that it did not differ from that of the wild-type NTHi 2019 (data not shown). Both were able to incorporate sialic acid into their LOS. This data suggested that either there are multiple sialic acid transporters present in NTHi or that this gene does not encode the functional sialic acid transporter of NTHi 2019.

Cloning and Mutagenesis of HI0147—The ORF HI0147 from the *H. influenzae* Rd genome database encodes a predicted protein of 633 amino acids. It was identified by homology with genes known to encode the transmembrane components of the TRAP-type C4-dicarboxylate transport system from *Vibrio vulnificus* and *Photobacterium profundum*. The homology of HI0147 in both cases is high (~50% identity and 70% homology). The HI0147 gene appears to be a fusion of the two membrane spanning components of the TRAP-type transport system. The proximity of this gene encoding a potential transporter to the nan operon, suggests that this gene may be involved in the uptake of environmental sialic acid. A Blast comparison of HI0147 with TRAP transporters from several gram-negative bacterial species can be seen in the supplemental data.

Transformants of 2019HI0147 were screened using a colony blot assay with the monoclonal antibody 3F11, which is specific for an N-acetyllactosamine epitope (Yamasaki et al., (1991) Mol Immunol 28, 1233-1242). This epitope is masked by the addition of sialic acid to the LOS. In the wild-type, the 3F11 epitope is only observed upon treatment of the blotted colonies with neuraminidase. In the two transformants, however, 3F11 binding was observed both before and after neuraminidase treatment, suggesting that these mutants lack sialic acid and thus display N-acetyllactosamine as a terminal disaccharide on their LOS.

Figure 2:
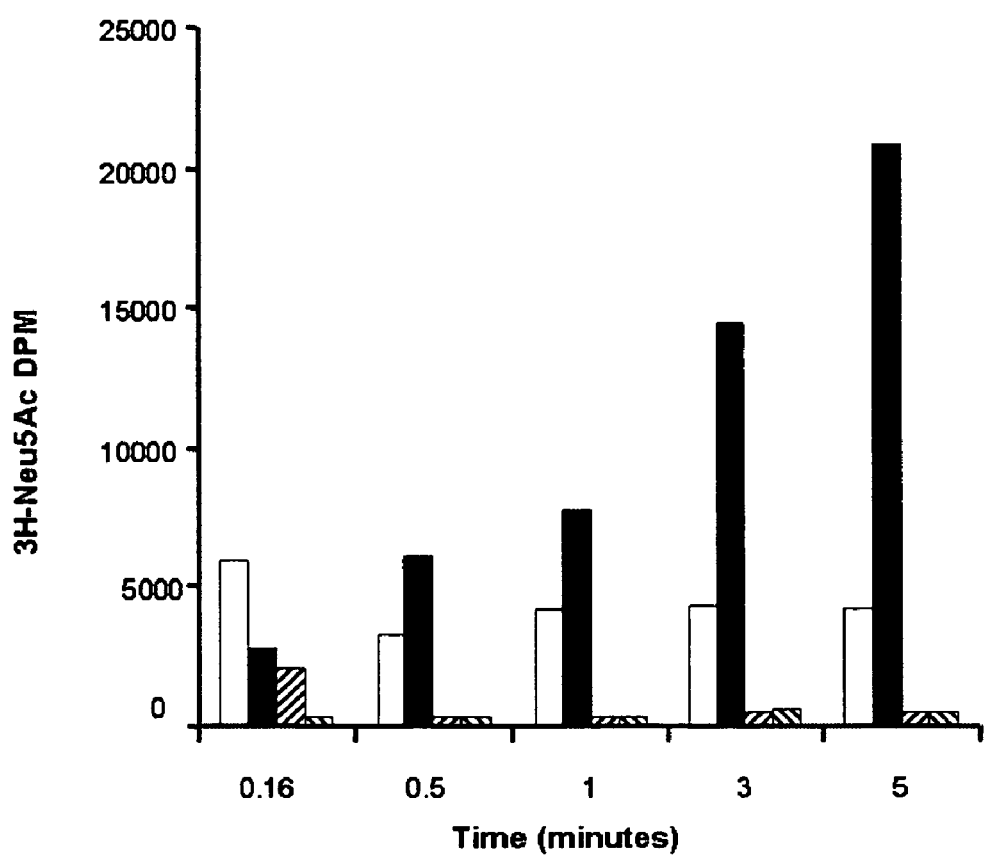
FIG. 2. Uptake/incorporation of [$^3$H]-sialic acid into the following.

Uptake of [$^3$H]-sialic acid by NTHi 2019, 2019nanA, 2019HI0147, and 2019HI0147::nanA—NTHi 2019, 2019nanA, 2019HI0147, and 2019HI0147::nanA were studied for their ability to transport [$^3$H]-sialic acid. The $^3$H-label of the sialic acid used in the uptake assay is located on C-9 and thus forms part of the pyruvate when the sialic acid is metabolized by the neuraminyl lyase (NanA), ultimately being lost as $^3H_2O$. Thus, the uptake assay is measuring the incorporation of sialic acid into the LOS and does not take into account for sialic acid that enters the degradation pathway. The neuraminyl lyase (nanA) mutants were included in this study to assure that all of the transported sialic acid was incorporated into the LOS rather than into degradative pathways (Vimr et al., (2000) Mol Microbiol 36, 1113-1123). FIG. 2 shows the results of these studies. As can be seen, 2019HI0147 and 2019HI0147::nanA were unable to transport sialic acid, and failed to accumulate an appreciable amount of the sialic acid over the 5 minute time course of the experiment. During this time, NTHi 2019 acquired between 8- to 9-fold more sialic acid than NTHi 2019HI0147, while NTHi 2019nanA accumulated 80-fold more sialic acid than 2019HI0147::nanA. When the time course is extended to 25 minutes, the wildtype maintains a steady state, whereas the 2019nanA mutant continues to accumulate sialic acid without reaching saturation. These studies indicate that the protein encoded by HI0147 is the sialic acid transporter in NTHi 2019 and should be designated as SiaT. Henceforth, 2019HI0147 will be referred herein to as 2019siaT.

Comparative analysis of LOS from NTHi 2019 and 2019siaT—LOS from NTHi 2019 wild-type and the siaT mutant was prepared from these strains grown on S-BHI agar with or without supplemental sialic acid. A portion of the LOS sample was treated with neuraminidase and then pre- and post-neuraminidase treatment samples were resolved by SDS-PAGE (FIG. 3A). The NTHi 2019 wild type gave a typical glycoform pattern for this strain, with a number of bands that became intensified upon growing the bacteria with supplemental sialic acid (FIG. 3A, compare lanes 1 and 3). These intensified glycoforms disappear upon treatment of the LOS with neuraminidase and the acceptor glycoforms become intensified (FIG. 3A, compare lanes 1 and 3 with 2 and 4, respectively). In contrast, the glycoforms observed for the 2019siaT mutant remained the same regardless of whether or not supplemental sialic acid was added to the growth media (FIG. 3A, compare lanes 5 and 7). Equally, there were no differences in the LOS profiles after neuraminidase treatment (FIG. 3A, compare lanes 5 and 7 with 6 and 8, respectively). Comparing the LOS of the mutant with the wild-type it seems that the profile is more similar to that of the neuraminidase treated LOS. Taken together this data suggests that in this mutant sialic acid is not incorporated into the LOS. A western blot analysis using 3F11 was carried out on the wild-type and the 2019siaT mutant LOS. The wild-type LOS grown on BHI without supplemental sialic acid was negative for 3F11 binding, suggesting that enough sialic acid could be incorporated into the LOS to mask the 3F11 epitope (FIG. 3B, lane 1). This was also the case when the wild-type bacteria were grown on BHI with supplemental sialic acid (FIG. 3B, lane 3). When treated with neuraminidase wild-type grown in both conditions showed a similar banding pattern corresponding to LOS glycoforms containing terminal N-acetyl-lactosamine (FIG. 3B, lanes 2 and 4). As for the 2019siaT mutant, bands are detected even when the bacteria are grown with supplemental sialic acid, suggesting an inability to mask this epitope (FIG. 3B, lanes 5 and 7). The number of bands detected after neuraminidase treatment remains the same showing that no further epitopes are unmasked after this treatment (FIG. 3B, lanes 6 and 8). Interestingly, there are striking differences between the epitopes present in the wild-type after neuraminidase treatment and the 2019siaT mutant suggesting that there may be regulation of which glycoforms are expressed when sialic acid is not available to the bacteria (FIG. 3B, compare lanes 2 and 4 with lanes 6 and 8, respectively).

MALDI-TOF-MS of O-Deacylated LOS—To further investigate the LOS phenotype, wild-type and HI0147 mutant LOS were O-deacylated by treatment with anhydrous hydrazine and analyzed by MALDI-TOF mass spectrometry. Previous studies have shown that NTHi 2019 produces a complex mixture of LOS glycoforms (Phillips et al., (1992) Biochemistry 31, 4515-4526; Greiner et al., (2004) Infect Immun 72, 4249-4260; Gaucher et al., (2000) Biochemistry 39, 12406-12414). The major component of this mixture has been extensively studied and is known to consist of a lactose moiety (Galβ1,4-Glcβ1-) linked in a β1,4-linkage to Hep$^I$ of the characteristic core structure of *H. influenzae* (Hep$^{III}$α1,2-Hep$^{II}$α1,3-Hep$^I$α1,5-Kdo(P)-lipid A) (Phillips et al., (1992) Biochemistry 31, 4515-4526; Schweda et al., (1993) Carbohydr Res 246, 319-330; Masoud et al., (1997) Biochemistry 36, 2091-2103). The NTHi 2019 wild-type O-LOS gave a similar repertoire of glycoforms as that seen by Greiner et al. (Greiner et al., (2004) Infect Immun 72, 4249-4260) (FIG. 4A and Table 2) with the major glycoform being the lactose-containing glycoform modified with 2 or 3 phosphoethanolamine moieties ($B_2$ and $B_3$, respectively).

TABLE 2

O-LOS glycoforms identified by MALDI-TOF

| Glycoform[a] | Proposed composition[b] Hex, HexNAc, Neu5Ac | Calc'd [M − H]$^-$ | wt | wt + Neu5Ac | siaT | siaP + Neu5Ac |
|---|---|---|---|---|---|---|
| $A_2$ | 1, 0, 0 | 2236.9 | 2236.5 | 2236.4 | 2237.3 | 2236.5 |
| $A_3$ | 1, 0, 0 | 2360.0 | 2359.0 | 2358.5 | 2359.4 | 2359.4 |
| $B_2$ | 2, 0, 0 | 2399.0 | 2398.9 | 2399.1 | 2399.0 | 239839 |
| $B_3$ | 2, 0, 0 | 2522.1 | 2522.3 | 2521.6 | 2522.1 | 2522.4 |
| $C_2$ | 3, 0, 0 | 2561.2 | 2561.5 | 2561.8 | 2562.3 | 2560.9 |
| $C_3$ | 3, 0, 0 | 2684.2 | 2686.0 | 2685.4 | 2685.9 | 2685.0 |
| $D_1$ | 4, 0, 0 | 2600.3 | 2601.4 | 2600.1 | 2601.4 | 2600.9 |
| $D_2$ | 4, 0, 0 | 2723.3 | 2723.3 | 2723.3 | 2723.3 | 2723.3 |
| $D_3$ | 4, 0, 0 | 2846.4 | 2845.9 | 2846.2 | 2847.0 | 2846.0 |
| $E_1$ | 5, 0, 0 | 2762.4 | 2762.2 | — | 2762.6 | 2762.3 |
| $E_2$ | 5, 0, 0 | 2885.5 | 2885.6 | — | 2885.8 | 2885.2 |
| $E_3$ | 5, 0, 0 | 3008.5 | 3008.9 | 3008.4 | 3009.5 | 3008.7 |
| $F_1$ | 3, 1, 0 | 2641.3 | 2641.7 | 2641.4 | 2641.7 | 2640.9 |
| $F_2$ | 3, 1, 0 | 2764.4 | 2765.0 | 2765.5 | 2765.5 | 2765.2 |
| $G_1$ | 4, 1, 0 | 2803.5 | 2804.6 | 2804.5 | 2804.2 | 2802.9 |
| $H_1$ | 5, 1, 0 | 2965.6 | 2965.0 | 2965.5 | 2965.9 | 2964.7 |
| $H_2$ | 5, 1, 0 | 3088.7 | 3089.2 | 3089.8 | 3089.1 | 3088.6 |
| $B_3$* | 2, 0, 1 | 2813.4 | 2813.4 | 2812.3 | — | — |
| $B_2$** | 2, 0, 2 | 2981.6 | 2981.2 | 2980.9 | — | — |
| $B_3$** | 2, 0, 2 | 3104.6 | 3104.7 | 3104.5 | — | — |
| $D_1$* | 4, 0, 1 | 2891.5 | 2891.1 | 2890.7 | — | — |
| $D_1$** | 4, 0, 2 | 3182.8 | 3181.1 | 3181.3 | — | — |
| $D_2$** | 4, 0, 1 | 3305.8 | 3305.8 | 3304.6 | — | — |
| $E_1$* | 5, 0, 1 | 3053.7 | 3054.0 | 3054.5 | — | — |
| $E_3$* | 5, 0, 1 | 3299.8 | 3300.5 | 3299.4 | — | — |
| $F_2$* | 3, 1, 0 | 3055.6 | 3055.5 | 3054.8 | — | — |
| $F_3$* | 3, 1, 1 | 3178.7 | 3178.8 | 3179.0 | — | — |
| $H_2$* | 5, 1, 1 | 3379.9 | 3379.5 | 3379.3 | — | — |
| $I_2$* | 6, 1, 1 | 3542.1 | 3541.9 | 3542.6 | — | — |
| $I_2$** | 6, 1, 2 | 3833.3 | 3833.9 | 3832.8 | — | — |

[a]Number of PEA moieties are denoted by subscripts, asterisks indicate the number of sialic acid residues.
[b]Proposed compositions contain a minimum core structure consisting of Hep3, Kdo(P) and O-deacylated lipid A.
[c]All molecular weights are average Various larger glycoforms are present which differ from the B-glycoforms by the addition of up to four hexoses and a single N-acetylhexosamine. Additionally, many of the glycoforms can be decorated with up to two sialic acid moieties, such glycoforms disappear upon neuraminidase treatment of the O-LOS. The proportion of sialylated glycoforms present increases when the wild-type bacteria are grown in the presence of sialic acid (FIG. 4B). The MALDI-TOF-MS spectra of the O-LOS from 2019siaT show a similar diversity in glycoforms, however the mutant lacks the sialic acid-containing LOS glycoforms that could be seen in the wild-type (FIG. 4C). These sialylated species are also completely absent from the O-LOS of 2019siaT grown on sialic acid supplemented media (FIG. 4D), indicating that in the absence of the siaT, the bacteria are not capable of incorporating sialic acid into their LOS.

Bactericidal assay—It has been shown previously that there is a correlation between the incorporation of terminal sialic acid in LOS and protection of *H. influenzae* from complement-mediated killing of the bacteria by normal human serum. Since 2019siaT cannot acquire sialic acid for incorporation into the LOS, it is likely that such a bacterium would have an increased susceptibility to killing by normal human serum. To investigate this we carried out a bactericidal assay on the wild-type, 2019siaT, 2019nanA and 2019siaT:: nanA. In the absence of supplemental sialic acid in the media both the wild-type, 2019siaT and 2019siaT::nanA were susceptible to killing by normal human serum (FIG. 5A). Interestingly, the 2019nanA mutant, was resistant to serum killing, suggesting that the bacteria can acquire sufficient sialic acid from the BHI media (which contains trace amounts of sialic acid) to afford protection from serum killing. Wild-type and 2019nanA grown in media supplemented with 20 µM sialic acid were protected from serum killing by incorporation of sialic acid into their LOS (FIG. 5B). Conversely, 2019siaT and 2019 siaT::nanA when grown in the presence of sialic acid were still susceptible to serum killing (FIG. 5B). As a control the experiment was repeated using heat-inactivated serum, as expected both wild-type and mutants were all capable of surviving this treatment (FIGS. 5C and D). This data clearly supports the MALDI-TOF-MS data and shows that in the absence of the siaT, *H. influenzae* are incapable of incorporating sialic acid into their LOS.

Discussion

The surface of NTHi is covered with LOS molecules. Incorporation of terminal sialic acid into the LOS enables NTHi to evade complement-dependent killing mechanisms, an important part of the host immune system (Hood et al., (1999) Mol Microbiol 33, 679-692; Hood et al., (2001) Mol Microbiol 39, 341-350). The pathways that are involved in the incorporation and the regulation of incorporation of sialic acid into the LOS are important targets for future drug development. Many of the genes involved in the metabolism of sialic acid in *H. influenzae* have been characterized including the CMP-sialic acid synthetase (Hood et al., (1999) Mol Microbiol 33, 679-692), sialyltransferases (Hood et al., (2001) Mol Microbiol 39, 341-350; Jones et al., (2002) J Biol Chem 277, 14598-14611) and the neuraminyl lyase (Vimr et al., (2000) Mol Microbiol 36, 1113-1123). As yet the sialic acid transporter of *H. influenzae* has not been characterized. Until recently it was thought that the sialic acid transporter of *H. influenzae* was encoded by the ORF HI1104, a gene that has homology to the nanT gene of *Escherichia coli* (Vimr et al., (1985) J Bacteriol 164, 845-853). The nanT gene product is a secondary transporter of the major facilitator superfamily that imports sialic acid in symport with a proton. Deletion of the HI1104 nanT homolog in *H. influenzae* had little or no effect on the ability of the bacteria to incorporate sialic acid into their LOS. *H. influenzae* lacks a sialic acid synthesis pathway suggesting that either the HI1104 is not a sialic acid transporter or that there is a second transporter that is capable of importing sialic acid into the cells.

More recently in the literature it has been suggested that *H. influenzae* has a sialic acid transporter which is unique from that of the *E. coli* nanT (Vimr et al., (1985) J Bacteriol 164, 845-853)). The genes HI0146 and HI0147 (siaT) have a close proximity in the *H. influenzae* genome to the nan-operon that encodes the genes responsible for the catabolism of sialic acid. By homology, these genes were predicted to encode an extracellular solute receptor (ESR) and the transporter domains, respectively, of a transporter of the tripartite ATP-independent periplasmic (TRAP) family (Kelly et al., (2004) Annu Rev Biochem 73, 241-268; Rabus et al., (1999) Microbiology 145 (Pt 12), 3431-3445). Such transporters have been reported previously in bacteria and are often involved in the transport of $C_4$-dicarboxylates such as succinate and fumarate using the electrochemical proton gradient as a driving force (Forward et al., (1997) J Bacteriol 179, 5482-5493).

The sialic acid uptake assay demonstrated that the HI0147 gene product is likely the SiaT. That both the 2019HI0147 and 2019HI0147::nanA mutants were incapable of sialic acid uptake indicated that the HI0147 gene product was required prior to activation of the sialic acid by the CMP-sialic acid synthetase, thus implicating HI0147 as the transporter (siaT). The assay also demonstrated some interesting aspects of the uptake and incorporation of sialic acid into the LOS of *H. influenzae*. In the wild-type the amount of sialic acid detected rapidly reaches a 'steady-state,' in contrast to the 2019nanA mutant that continued to accumulate sialic acid throughout the assay. Indeed, it has been shown previously that *H. influenzae* nanA mutants hypersialylate their LOS (Vimr et al., (2000) Mol Microbiol 36, 1113-1123). This suggests that the point of regulation of sialic acid levels within the bacteria occurred not through regulation of the transporter, but through regulation of the downstream gene products in the sialic acid pathway, such as the neuraminyl lyase and the CMP-N-sialic acid synthetase. The concept that the sialic acid transporter is expressed at a constitutive level would make some sense because sialic acid, as well as being an important molecule in the evasion of the host immune response, is a valuable carbon and nitrogen source.

Deletion of siaT, as suggested by the sialic acid uptake data, results in bacteria incapable of incorporating sialic acid into their LOS This suggests that this gene is indeed involved in the uptake of sialic acid in *H. influenzae*. This conclusion is supported by the SDS-PAGE and MALDI-TOF-MS data, all of which conclusively indicate the lack of sialic acid-containing LOS glycoforms on the 2019siaT mutant. As a consequence of this, the siaT mutant was severely compromised in its ability to evade the host immune response as evidenced by the fact that the mutant was susceptible to complement-killing when exposed to normal human sera. The Western blot analysis suggested that alongside the inability to incorporate sialic acid into its LOS, the 2019siaT mutant expressed fewer glycoforms containing terminal N-acetyllactosamine. This suggested that in the absence of sialic acid, the bacteria express different glycoforms.

A point of secondary interest was that the 2019nanA mutant when grown on BHI only media (which contains trace amounts of sialic acid) could acquire enough sialic acid from the media to produce LOS sufficiently sialylated as to protect the bacteria from complement mediated lysis. This indicated that the deletion of nanA led to an increase in 'flux' of sialic acid into the LOS-incorporation pathway.

This is the first TRAP transporter to be characterized in *H. influenzae* and also the first TRAP transporter known to transport sialic acid. The best described and characterized TRAP transporter is the DctPQM $C_4$ dicarboxylate transporter of *Rhodobacter capsulatus*, though various homologs have been identified in archaea and gram-negative bacteria. DctP is the periplasmic extracellular solute receptor, while DctQ and M represent the integral membrane proteins with 4 and 12 predicted membrane spanning regions, respectively (Forward et al., (1997) J Bacteriol 179, 5482-5493). In *H. influenzae* these two membrane proteins are encoded by a single gene containing a total of 16 predicted membrane-spanning regions (Rabus et al., (1999) Microbiology 145 (Pt 12), 3431-3445). The ESR protein is thought to increase the uptake affinity of the transporter by binding sialic acid and delivering it to the transporter. Such a high affinity sialic acid uptake system may be important for the bacteria in their normal physiological environment. The novelty of this transporter may make this transporter an important drug target given *H. influenzae's* dependence on sialic acid for immune evasion.

In conclusion, deleting the siaT gene of NTHi 2019 leads to bacteria that are not capable of the uptake of sialic acid, thus the bacteria cannot sialylate their LOS making them vulnerable to the complement-mediated killing. The siaT gene product therefore appears to be the sole sialic acid transporter of *H. influenzae*. The siaT gene product is a transporter of the TRAP transporter family, making this the first sialic acid transporter of this type to be characterized.

EXAMPLE 2

The Role of Sialic Acid and Complex Carbohydrate Biosynthesis in Biofilm Formation by Nontypeable Haemophilus Influenzae in the Chinchilla Middle Ear Others have shown that host-derived sialic acid is incorporated into *Haemophilus influenzae* lipopolysaccharide and is a major virulence factor in experimental otitis media. Bouchet et al., (2003) PNAS 100(15):8898-903. Previous studies have also indicated that SiaA, SiaB and WecA are involved in the in vitro production of a nontypeable *Haemophilus influenzae* (NTHi) biofilm. To investigate whether these genes were involved in biofilm production in vivo, NTHi 2019 mutants in carbohydrate biosynthesis were studied in the chinchilla middle ear infection model. Chinchillas were inoculated with the parental isolate (strain 2019) or with one of five mutants. The wild-type strain 2019 formed a biofilm within the chinchilla tympanum. The NTHi 2019 mutants in wecA, lsgB, siaA, pgm, and siaB were either unable to form biofilms or formed biofilms of reduced mass and organization. Lectin analysis indicated that sialic acid was an important component of the NTHi 2019 biofilm produced in the chinchilla middle ear. These data suggested that genes involved in carbohydrate biosynthesis and assembly play an important role in the ability of NTHi to form a biofilm in vivo.

The work presented in this Example shows that if sialic acid is not incorporated into the Lipooligosaccharide (LOS), the organism cannot survive killing by antibody-complement dependent mechanisms. The siaB mutant cannot add the nucleotide to activate sialic acid for incorporation by the sialyltransferase onto the LOS. This mutant is avirulent in the chinchilla middle ear model. It does not form a biofilm and does not survive in the middle ear.

Materials and Methods

Bacteria and culture conditions—Strains used are described in Table 3 (Greiner et al., (2004) Infect. Immun 72, 4249-60).

TABLE 3

Bacterial Strains

| Strain or Plasmid | Genotype | Source or Reference |
|---|---|---|
| NTHi 2019 | non-typeable *Haemophilus influenzae* | Jones et al., (2002) J Biol Chem 277, 14598-611 |
| NTHi 2019lsgB | sialyltransferase | Jones et al., (2002) J Biol Chem 277, 14598-611 |
| NTHi 2019pgm | phosphoglucomutase | Swords et al., (2000) Mol Microbiol 37, 13-27 |
| NTHi 2019wecA | undecaprenyl-phosphate α-N-acetylglucosaminyltransferase | Greiner et al., (2004) Infect. Immun 72, 4249-60 |
| NTHi 2019siaA | sialyltransferase | Jones et al., (2002) J Biol Chem 277, 14598-611 |
| NTHi 2019siaB | CMP-Neu5Ac synthetase | Hood et al., (1996) Mol Microbiol 22, 951-65 |

NTHi strain 2019 is a clinical isolate from a patient with chronic obstructive pulmonary disease (Campagnari et al., (1987) Infect Immun 55, 882-7). This strain was reconstituted from a frozen stock culture and propagated on brain heart infusion (BHI) agar (Difco, Detroit, Mich.) supplemented with 10 μg hemin/ml (Sigma Chemical Co., St. Louis, Mo.) and 10 μg nicotinamide adenine dinucleotide (NAD)/ml (Sigma) at 37° C., 5% $CO_2$.

Animal model—Adult chinchillas (*Chinchilla lanigera*) were used (mean weight 400-600 gms). Middle ears were inoculated with 300 μl sterile pyrogen-free saline containing 1500-2000 cfu NTHi, via transbullar inoculation as previously described (Sirakova et al., (1994) Infect Immun 62, 2002-20), then monitored daily for signs of OM via video-otoscopy and tympanometry. Five days later, chinchillas were sacrificed, effusions (if present) were retrieved and the bullae were removed. Bullae were then either snap frozen over liquid nitrogen and stored on dry ice, or were packed on ice for immediate analysis of whole mounts using a vital fluorescent stain and CSLM. Recovered effusions were serially diluted and plated for semi-quantitative determination of cfu NTHi/ml middle ear fluid.

Primary human bronchial airway epithelial cell cultures—To compare with in vivo data, biofilm formation was also assayed using primary human bronchial epithelial cells. Cells were cultured on glass coverslips in 24-well plates as described (Ketterer et al., (1999) Infect Immun 67, 4161-70). Infection was initiated by the addition of either $10^7$ NTHi strain 2019 or 2019wecA (MOI~1:100), followed by incubation for 48 hours with media changed after 24 hours. To examine for biofilm formation, the glass coverslip was removed, placed in a well containing 4% glutaraldehyde and the sample analyzed by scanning electron microscopy, as previously described (Edwards et al., (2000) Infect Immun 68, 5354-63).

Bactericidal Assay—NTHi strain 2019, 2019siaB and 2019pgm were grown to early log phase, $A_{600}$=0.2, in supplemented BHI broth. A 0.5 ml aliquot of each was centrifuged for one minute at 10,000 RPM, at room temperature. The pellet was re-suspended in 1.0 ml of phosphate buffered salt solution (PBSS) consisting of 10 mM $K_2HPO_4$, 10 mM $KH_2PO_4$, 136 mM NaCl, 5 mM KCl, 1 mM $CaCl_2$, 0.3 mM $MgCl_2 6H_2O$, 1 mM $MgSO_4 7H_2O$ and 0.01% BSA, pH 7.0. A 1:10 dilution of this bacterial suspension was used to deliver approximately $10^5$ bacteria to each well. The bactericidal assay, modified from Andreoni et al (Andreoni et al., (1993) J Infect Dis 168, 227-31), was carried out in a 96-well plate in 200 μl final volume. Chinchilla blood was obtained aseptically by cardiac puncture, allowed to clot on ice, the serum was collected by centrifugation at 4° C. and was immediately stored frozen at −80° C. for later use in the assay.

Live/Dead™ bacterial stain—Bullae that had previously been placed on ice, were further dissected to isolate the inferior bullae, incubated with 30 μl of LIVE/DEAD™ stain (BacLight Bacterial viability kit, Molecular Probes, Eugene, Oreg.) for 15 minutes, then rinsed in buffer. Biofilms were visualized using a Zeiss LSM410confocal scanning laser microscope (Carl Zeiss Microimaging Inc., Thornwood N.Y.).

OCT embedment—To preserve the architecture of any biofilms formed in vivo, bullar mucosa were embedded in OCT compound (Fisher Scientific, Pittsburgh, Pa.) for cryosectioning. Briefly, the inferior and superior portions of iced, dissected bullae were separated and any effusion present was retrieved by aspiration. The inferior bulla was then rinsed several times and drained via wicking onto absorbent paper. OCT was slowly added via 18G needle. Bullae were then snap frozen over liquid nitrogen and placed on a bed of dry ice. External bone was then carefully chipped away, leaving the middle ear mucosa and any attached biofilm intact. The resulting block was split in a plane perpendicular to the tympanic membrane. Serial sections (4 μm thickness) were cut on a Leica CM3050S cryotome (Leica Microsystems Inc., Bannockburn, Ill.), placed on Superfrost® slides (Fisher Scientific, Pittsburgh, Pa.), fixed in 4% paraformaldehyde (w/v in 0.1 M phosphate buffer, pH 7.4) and stored at −80° C.

Lectin analysis—Biofilms isolated from the chinchilla middle ear that had been infected with strain 2019 were subjected to lectin analysis using OCT embedded sections. Biofilm were cut into 1 μm thick sections and incubated with the following lectins; *Maachia amurensis*-fluorescein isothiocyanate (MAA-FITC) and *Sambucus nigra*—Texas red isothiocyanate (SNA-TRITC) (EY Laboratories, San Mateo, Calif.). *Maachia amurensis* lectin binds preferentially to a terminal Neu5Ac α2α3Gal, and *Sambucus nigra* lectin binds preferentially to terminal Neu5Ac α2α6Gal. Samples were examined by confocal microscopy, using a Bio-Rad CSLM located at the Central Microscopy Research Facility at the University of Iowa (Iowa City, Iowa).

Transmission Electron Microscopy (TEM)—OCT sections were also processed for TEM by embedding in LR White resin (Ted Pella, Inc., Redding, Calif.). Sections approximately 85 nm thick were cut and the biofilm was then stained with 5% uranyl acetate for viewing with an H-7000 Hitachi transmission electron microscope.

Results

Studies using in vitro assays showed that NTHi strain 2019, strain 2019pgm and strain 2019lsgB produced biofilms, while strains 2019siaA, strain 2019siaB and strain 2019wecA did not (Greiner et al., (2004) Infect. Immun 72, 4249-60). Here, these strains (Table 4) were examined in the chinchilla to determine the impact of these mutations on biofilm formation in vivo. It was observed that, whereas all ears showed signs of inflammation during the 5-day period, the inflammatory response elicited by each of these six strains was highly variable as was their ability to produce an effusion or form a biofilm.

TABLE 4

| Strain | inoculum (cfu/ear) | fluid (right ear) - cfu NTHi/ml middle ear | fluid (left ear) - cfu NTHi/ml middle ear |
|---|---|---|---|
| 2019 wt | 1500 | 208e6 | 1.04e6 |
| 2019wecA | 1500 | 3.3e7 | 6.1e7 |
| 2019lsgB | 1950 | no effusion | no effusion |
| 2019siaA | 2070 | 4.7e7 | 1.6e8 |
| 2019siaB | 2190 | Sterile | Sterile |
| 2019pgm | 1950 | no effusion | Sterile |

Semi-quantitative determination of cfu NTHi/ml of middle ear fluid 5 days post challenge. Actual inoculum delivered was confirmed by plate count. No effusion indicates that there was no effusion present in the middle ear space whereas sterile indicates that an effusion was present and fluid was retrieved but no culturable bacteria were present.

Gross and microscopic morphology of the biofilms in situ—For gross visualization of any biofilm present, dissected bullae were imaged by stereo microscope. For reference, in a naive chinchilla the inferior bulla is comprised of bone lined by a thin, shiny and colorless mucosal layer (FIG. 6A). The tympanic membrane is similarly thin and translucent in appearance with no signs of edema or erythema.

The bulla recovered from the chinchilla challenged with strain 2019 contained a large, creamy-colored and firm biofilm in the inferior aspect of the middle ear space (FIG. 6B). This biofilm extended along the bullar bone from approximately the tympanic orifice of the Eustachian tube to the bony niche immediately adjacent to the tympanic membrane. This biofilm was easily seen by the naked eye and was of a consistent color and density throughout. The bone in the inferior bulla was opaque with evidence of considerable thickening. Mild erythema of the mucosal layer, with some blood vessel dilation was seen throughout the mucosa lining the tympanum.

Gross examination of the bullae recovered from chinchillas challenged with either 2019lsgB or 2019siaA (FIGS. 6C and 6D, respectively), revealed very small biofilms that could be seen clearly only with aid of the dissecting microscope. Biofilms produced by these latter two mutants were located along the ventral surface of the inferior bullae. The bulla mucosa of these animals appeared less inflamed than that observed in the animal challenged with the parental strain. Slight erythema was noted in each ear, with some focal hemorrhagic sites (most likely due to the epitympanic taps performed to retrieve middle ear fluids). Overall, the mucosal lining was shiny and did not appear to be edematous or grossly thickened. The bone of the inferior bulla was slightly more opaque in the animal challenged with 2019siaA than is typical for a naive animal, however these changes were milder than those noted with the parent strain.

The remaining mutants (2019wecA, 2019siaB, and 2019pgm) (FIGS. 6E, 6F, and 6G, respectively) did not form a biofilm, as evidenced by gross examination. The bullae recovered from chinchillas challenged with either 2019siaB or 2019pgm appeared highly similar to that of a naive animal, with the exception of areas of slight erythema throughout for the animal receiving 2019siaB. However, the bulla from the chinchilla challenged with the wecA mutant (FIG. 6E) exhibited the greatest amount of erythema of all bullae examined here. Overall, the erythema was moderate in degree and uniform across the inferior bulla with several distinct hemorrhagic foci (again, likely due to epitympanic tapping). The bone was slightly thicker and more opaque than that of a naive animal however, the tympanic membrane was overall normal in appearance.

To better characterize the biofilm created by the parent strain, this mass was cryo-sectioned and analyzed using both light (FIG. 7A) and electron microscopy (FIG. 7B). Strain NTHi 2109 produced a biofilm characterized by long finger-like projections and numerous water channels (FIG. 7A). Electron microscopic analysis of an OCT- and Epon-embedded section showed organisms surrounded by a dense amorphous matrix (FIG. 7B).

Survival of NTHi in the chinchilla middle ear—Strain NTHi 2019 produced effusions in both ears and yielded cfu/ml counts that were several logs higher than the challenge inoculum, indicating that this strain could clearly survive and multiply within the chinchilla middle ear (Table 4). Conversely, strain 2019lsgB failed to induce an effusion in either middle ear. Strains 2019siaB and 2019pgm produced an effusion in at least one ear, however there were no culturable bacteria. The remaining mutants, 2019wecA, and 2019siaA induced culture-positive effusions bilaterally, as had the parental isolate, with cfu/ml counts several logs greater than the challenge inoculum, thus demonstrating active growth in vivo. However, despite the induction of culture-positive effusions, neither of these latter two mutants formed a biofilm that was similar architecturally to that of the parental strain and, in fact, the wecA mutant produced no biofilm in vivo.

The absence of an effusion suggests that NTHi had been cleared from the middle ear and thus a given mutant was more sensitive to the chinchilla immune response. Likewise, a sterile effusion could indicate that either any NTHi present within the middle ear space were occupying a biofilm and were not available in planktonic form for culture or perhaps that they had been eradicated by host immune responses. In vitro bactericidal assays using chinchilla serum supported the latter concept for two of the mutants characterized here. After one half-hour incubation in chinchilla serum, 99.5% of strain 2019 survived. Conversely, only 1% of strain 2019pgm and none of strain 2019siaB could be recovered over a similar time period.

Live/Dead Fluorescent stain—To extend observations made upon gross dissection, the contralateral bulla from each chinchilla was stained with a vital fluorescent stain and viewed by confocal microscopy (FIG. 8).

Strain 2019 produced a well-defined and highly organized biofilm containing long finger-like projections with numerous water channels and was comprised of viable NTHi throughout (FIG. 8A). Collectively, observations showed that strain 2019 could survive and multiply in the chinchilla host. It is important to note that the results also demonstrate that this strain could form a highly structured and viable biofilm.

Despite an inability to visualize a biofilm grossly in ears challenged with 2019pgm, this mutant also formed of an organized biofilm in vivo with fingerlike projections and water channels, however the biofilm was notably smaller in size compared to that of strain 2019 in the same time period (FIG. 8B). In vitro, strain 2019pgm produces biofilms similar in size and structure to that of the parental strain (Greiner et al., (2004) Infect. Immun 72, 4249-60). However, since these biofilms were much smaller in the chinchilla, and there were no culturable bacteria in middle ear fluids, the data suggests enhanced sensitivity to the host's immune response. As discussed above, this mutant was highly susceptible to the bactericidal activity of chinchilla serum in vitro.

The mutation in lsgB also had an effect on the architecture of the biofilm produced in vivo (FIG. 8C). This biofilm appeared to be very dense and compact with no apparent water channels. Moreover, there were large numbers of dead bacteria within the biofilm as demonstrated by the red staining of cells due to uptake of propidium iodide. The presence of a large population of dead bacteria in the biofilm matrix coupled with the lack of effusion in either ear would suggest that this mutation also had an effect on either the overall fitness of this strain in vivo or its sensitivity to the chinchilla immune response. Evidence of a mild inflammatory response with limited new bone formation as observed upon gross dissection was supported by the fluorescent microscopy images.

Strain 2019siaA formed a biofilm (FIG. 8D) that was very similar in structure to that produced by 2019lsgB. This biofilm was dense and compact, lacking water channels. In contrast to the 2019lsgB biofilm, however, the 2019siaA biofilm contained fewer dead cells. Also, this mutant induced the production of effusions containing large numbers of viable, planktonic bacteria. Collectively, these data show that the mutation in the siaA gene affected the ability of this organism to form an organized biofilm in vivo but did not either markedly decrease its fitness in vivo or greatly increase its sensitivity to the host's immune response.

The 2019wecA (FIG. 8E) mutant also produced effusions containing large numbers of bacteria. No biofilm, however, was detected in the whole mounts stained with the vital fluorescent stain, confirming observations made upon gross dissection. Despite the absence of a biofilm, due to the observation of focal areas of strong fluorescence on the mucosa lining the inferior bulla, viable bacteria were likely present on the epithelial cell surface. SEM studies (described below) were conducted to further investigate this observation.

Finally, enhanced sensitivity to the chinchilla's immune response in strain 2019siaB, as suggested by data obtained in bactericidal assays, was supported by the presence of both sterile effusions produced in the middle ears five days after TB challenge and by the lack of biofilm formation, as evidenced by fluorescent microscopy (FIG. 8F).

SEM analysis of strain 2019wecA infected human bronchial epithelial cells—Studies were performed on strains 2019 and 2019wecA infecting primary human bronchial epithelial cells over 48 hours to determine if the characteristics of these biofilms were similar to those seen in vivo. Microcolonies and the initial formation of a biofilm could be seen with strain 2019 (FIG. 9A). Strain 2019wecA (FIG. 9B) formed neither structure, but was present as individual bacteria on the airway cell surface. This is very similar to what was seen in the infected chinchilla middle ear with the parental isolate 2019 and the wecA mutant (FIGS. 8A and 8E, respectively).

Lectin analysis of the biofilm—The NTHi 2019 biofilm was further analyzed with two lectins (FIG. 10). The *Sambucus nigra* lectin preferentially binds Neu5Acα2→6galactose, and *Maachia amurensis* lectin preferentially binds Neu5Acα2→3galactose. SNA-TRITC bound to the Neu5Ac in the biofilm matrix, whereas MAA-FITC binds the Neu5Ac and lactosyl groups on the LOS of the bacteria (FIG. 10A). To confirm that the labeling observed was in fact due to the presence of sialic acid, a serial section was treated with neuraminidase prior to lectin labeling. Neuraminidase removed all of the labeling by SNA-TRITC and some of the binding of MAA-FITC to the biofilm (FIG. 10B). Additionally, it appeared that the SNA-TRITC bound diffusely to the biofilm matrix while the MAA-FITC bound exclusively to the organisms within the biofilm. This later lectin has specificity for lactose as well as sialic acid, while SNA is more specific for sialic acid in an α2-6 linkage (Brinkman-Van der Linden et al., (2002) Anal Biochem 303, 98-104). This suggested that the sialic acid in the biofilm matrix is in an α2-6 linkage, in contrast to the α2-3 linkage known to be present on NTHi 2019 LOS (Jones et al., (2002) J Biol Chem 277, 14598-611). These sections were also stained with the DNA stain To-Pro3 which revealed the nuclei of numerous monocytic-like host cells infiltrating the biofilm.

Discussion

A biofilm matrix is primarily comprised of bacterial exopolysaccharides, along with components scavenged from the environment. NTHi produces LOS and often decorates its LOS with sialic acid that has been acquired from its host. Sialic acid on the surface of bacteria is thought to confer resistance to both complement-mediated killing and the ability to bind to host cell receptors. NTHi has three distinct sialyltransferases, SiaA, Lic3A, and LsgB (Jones et al., (2002) J Biol Chem 277, 14598-611), all of which can be involved in placing sialic acid on the LOS. SiaA has homology to a sialyltransferase identified in $H.$ $ducreyi$ and utilizes a terminal lactosamine (Gal-GlcNAc) as an acceptor. Lic3A is an α-2,3-sialytransferase, with homology to the sialyltransferase in $Campylobacter$ $jejuni$ and uses a terminal Gal-Gal as an acceptor. LsgB places sialic acid on a terminal lactosamine of the LOS, but differs from the acceptor of SiaA by the presence of a unique substitution on lactosamine. It was shown that SiaA is the sialyltransferase involved in incorporating sialic acid into the biofilm (Swords et al., (2003) J Endotoxin Res 9, 131-44). For NTHi, sialic acid is obtained from environmental sources of 5-acetylneuraminic acid (Neu5Ac). Prior to transfer to LOS, the sialic acid must first be activated by the addition of a CMP group (cystidine-5-phosphate) (Sutherland, (2001) Trends Microbiol 9, 222-7; Swords et al., (2003) J Endotoxin Res 9, 131-44). The gene responsible for this activity encodes a CMP-NANA synthase (SiaB). After activation, sialic acid is then transferred, via a sialyltransferase, as a terminal structure onto the LOS (Vimr et al., (2002) Trends Microbiol 10, 254-7).

Genes responsible for carbohydrate biosynthesis have been identified that have a high probability of being involved in biofilm formation by NTHi (Greiner et al., (2004) Infect. Immun 72, 4249-60). A mutation in the gene that encodes UDP-GlcNAc:undecaprenylphosphate GlcNAc-1-phosphate transferase (wecA), results in markedly reduced biofilm formation in vitro. The gene product of wecA adds the first sugar to the carrier lipid undecaprenol in the biosynthesis of complex carbohydrates such as bacterial common antigen and O-antigens. WecA is not involved in NTHi LOS biosynthesis, but appears to be involved in the synthesis of the biofilm polymer. These studies suggest that a crucial component of the biofilm is assembled on a carrier lipid, and then transported to the external environment. AlgC of $Pseudomonas$ $aeruginosa$ has a central role in the production of alginate and LPS. The enzyme phosphoglucomutase is a homolog to AlgC, and is responsible for the conversion of glucose-6-phosphate to glucose-1-phosphate. In carbohydrate biosynthesis, glucose-1-phosphate is further converted to UDP-glucose and/or UDP-galactose. These nucleotide sugars are then used as substrates for incorporation of hexoses into the complex carbohydrates. Mutation in pgm abrogates this process due to nucleotide substitution of these hexoses (Swords et al., (2000) Mol Microbiol 37, 13-27).

NTHi strain 2019 and deletion mutants constructed in genes listed above, have been analyzed for their ability to form biofilms in vitro (Greiner et al., (2004) Infect. Immun 72, 4249-60) using both flow chambers as well as primary human bronchus cell cultures (Ketterer et al., (1999) Infect Immun 67, 4161-70). Here, a chinchilla transbullar challenge model (Sirakova et al., (1994) Infect Immun 62, 2002-20; Bakaletz et al., (1999) Infect Immun 67, 2746-62) was used to study the ability of strain 2019 and several mutants to form biofilms in a mammalian host. Moreover, the glycocalyx of the biofilm produced in vivo was analyzed using lectin labeling.

It was found that all five isolates with deletion mutations within genes involved in LOS biosynthesis were compromised in their ability to survive and/or form a mature biofilm in the chinchilla middle ear. Whereas the parental strain NTHi 2019 was able to multiply within the tympanum, induce culture-positive effusions, and form a large, predominantly viable and well-organized biofilm, isolates with mutations in the sialyltransferases lsgB or siaA showed a markedly different phenotype. When strain 2019lsgB was inoculated into chinchilla middle ears, a dense biofilm containing a large proportion of dead bacteria was present and there was no effusion in either ear of this animal. Conversely, strain 2019siaA survived and multiplied, however like the lsgB mutant, the biofilm produced was dense with no evident water channels and contained dead bacteria.

NTHi strain 2019wecA also survived and multiplied within the chinchilla middle ear. The investigators, however, were unable to detect the presence of a biofilm by any method used. This mutation likely interrupted the first step in biofilm biosynthesis. Thus, the phenotype exhibited a complete loss of biofilm production, as seen in the in vitro flow chamber assays (Greiner et al., (2004) Infect. Immun 72, 4249-60), and in the animal model presented here. Strain 2019pgm, with a deletion in a phosphoglucomutase gene, did not survive as well as the parental isolate within the middle ear. An effusion recovered from one middle ear was sterile and there was no effusion in the contralateral ear. This latter strain did, however, induce the formation of a biofilm that was smaller and less well organized than the parental isolate. The fifth mutant assayed, NTHi 2019siaB, was deficient in its ability to express a CMP-NANA synthetase. This isolate induced sterile middle ear effusions with no evidence of a biofilm five days after inoculation.

Data obtained with 2019siaB were consistent with those of Swords et al. (Swords et al., (2004) Infect Immun 72, 106-13), who assayed this mutant for survivability in a gerbil middle ear challenge model. Swords et al. also found that it was significantly compromised in ability to colonize and persist in vivo. Whereas the present investigators found sterile middle ear effusions in chinchillas five days after challenge, Swords et al. were able to recover NTHi, albeit at greatly reduced concentrations, from the gerbil middle ears up to three days post-inoculation. These differences are likely due to both the interval between direct challenge and sample collection, as well as the very large difference in inocula used (~2000 vs. $10^7$ cfu for chinchillas and gerbils, respectively). Whereas sensitivity to gerbil complement-mediated killing was not reported for the siaB mutant in that study (Swords et al., (2004) Infect Immun 72, 106-13), its sensitivity to chinchilla serum was shown here and likely played a key role in the present observations.

In summary, the wild type strain NTHi 2019 and five isogenic mutants were assayed for their ability to form a biofilm in vivo. The in vivo findings were compared to their ability to do form a biofilm in vitro. Overall, a good correlation between the in vitro and in vivo findings was established. In the chinchilla model, the host's immune system had an effect that may have compromised survivability and the ability to form a biofilm by 2019siaB and 2019pgm, which were both susceptible to complement mediated-bactericidal activity of chinchilla serum. The present studies also indicated that a wecA mutant behaves in identical fashions on human airway epithelial cells in culture and in the chinchilla middle ear. Infection in both models persists for the duration of the experiments, but there was complete failure to form microcolonies or a biofilm.

In an intact biological model system, such as experimental otitis media in the chinchilla middle ear, the interactions between bacterial virulence factors and host defenses can be analyzed. From these studies, it is clear that global effects on sialylation (siaA, siaB and lsgB mutants) of both LOS and the biofilm alter the ability of the organism to survive in a mammalian host. Modifications that effect biofilm formation alone, such as mutation of wecA, appear to have less of an effect on the organism's persistence in spite of the fact that no biofilm can be detected. Thus, biofilm formation occurs during infection in vivo. It should be noted that whereas biofilm formation is not essential for bacterial survival in the middle ear, LOS sialylation is indispensable.

EXAMPLE 3

Sialic Acid Binding Protein of H. influenzae

TRAP Transporters usually contain two proteins (dctQ and dctM) or a single fused protein but with two distinct domains and an extracytoplasmic solute protein (ESR). See FIG. 13. In H. influenzae siaT is a fused TRAP transporter, and siaP is the extracytoplasmic solute protein. SiaP is annotated as HI0146 in the TIGR genome. The nucleic acid sequence for siaP (SEQ ID NO: 11) is provided in FIG. 16, and the amino acid sequence (SEQ ID NO: 12) is provided in FIG. 17.

Using colony blots, the inventors showed that NTHi 2019siaP cannot acquire N-acetyl-5-neuraminic acid (Neu5Ac, also called "sialic acid") from the media. Monoclonal antibody 3F11 with specificity for the lactosamine acceptor for Neu5Ac on the lipooligosaccharide of NTHi 2019 was used to develop the blot. If sialic acid is bound to the lactosamine on the lipooligosaccharide, the lastosamine epitope is blocked and monoclonal antibody 3F11 cannot bind. The NTHi strain 2019 was grown on media containing Neu5Ac without neuraminidase treatment prior to monoclonal antibody 3F11. The 3F11 did not bind to the colonies. The NTHi strain 2019 was also grown on media containing Neu5Ac with neuraminidase treatment prior to monoclonal antibody 3F11. Monoclonal 3F11 binds to the colonies that have had the Neu5Ac cleaved from the lipoligosaccharide. NTHi strain 2019siaP was also grown on media containing Neu5Ac without neuraminidase treatment prior to monoclonal antibody 3F11. Monoclonal 3F11 binds, showing that the lactosamine that is not sialylated in this mutant. NTHi strain 2019siaP was also grown on media containing Neu5Ac without neuraminidase treatment prior to monoclonal antibody 3F11. The antibody bound to the colonies and was no different than the NTHi 2019siaP not treated with neuraminidase.

The inventors also determined whether $^3$H-Neu5Ac would bind to His-tagged siaP bound to a nickel affinity resin. FIG. 18 shows the results of three experiments demonstating the binding of $^3$H-Neu5Ac to His-tagged siaP bound to a nickel affinity resin. Two controls are included, the His-tagged luxS protein bound to a nickel affinity resin and nickel affinity with no protein bound to it. As can be seen, the $^3$H-Neu5Ac bound only to the resin to which siaT was bound.

The inventors performed Biacore® analysis of Neu5Ac binding to siaT (FIG. 19). Concentrations of Neu5Ac ranged from 10 to 50 mM. Binding peaked at 22 mM and calculations estimated the kD of siaT for Neu5Ac to be $1.7 \times 10^{-8}$. Studies with N-acetylmannosamine, mannose, galactose, glucose, fructose and xylose showed no binding to siaT at concentrations as high as 200 mM.

The protein siaP is a component of the sialic acid transport system and is a site that can be used to prevent uptake of sialic acid by an organism. As indicated above, siaP has an extremely high affinity for sialic acid, but failed to bind N-acetylmannosamine, mannose, galactose, glucose, fucose or xylose.

EXAMPLE 4

Inhibition of Sialic Acid Incorporation

The compound 3-fluorosialic acid inhibits Neu5Ac incorporation into H. influenzae. Thirteen possible inhibitors were tested and twelve did not have any effect, including Tamiflu™, Relenza™ and 2'-(4-Methylumbelliferyl)-α-D-N-acetylneuraminic acid sodium salt hydrate.

The compound 3-fluorosialic acid reduced uptake by 60%. FIG. 20 provides the results of the inhibition assay.

Assay: Sialic acid 10 uM was incorporated into Brain Heart Infusion plates containing NAD and Hemin. The inhibitor was also added at 0.01 μM, 0.1 μM, 1 μM and 10 μM concentrations. Control plates were simultaneously prepared which lacked inhibitor. Results obtained from these plates represented the 100% sialic acid incorporation The inhibition assay was performed by plating $10^7$ nontypeable *Haemophilus influenzae* onto each plate and allowed them to grow overnight in 5% $CO_2$ at 37° C. After 16 hours, organisms were collected from the plate and separately diluted in distilled water to a density of 0.1 absorbance at 600 nm.

Analysis: These organisms were analyzed for sialic acid incorporation onto the surface of the organism. To accomplish this, one hundred microliters was placed in a microtiter well and allowed to dry overnight in a 37° C. dry incubator. The next day the plates were washed in a microtiter washer and 100 microliters of antibody 3F11 in TBS Tween-20 was placed in each well. Monoclonal antibody 3F11 binds the lactosamine epitope to which the sialic acid is attached. If sialic acid is present, 3F11 will not bind. If sialic acid is absent, 3F11 binds. The plates were then allowed to set at 37° C. in a moist chamber for two hours. The plates were washed and 100 microliters of a mouse anti-IgM phosphatase conjugate was added to each well. The plates was allowed to set in a 37° C. incubator for one hour. The plate was washed, and 100 microliters p-nitrophenol-phosphate was added to each well. The plate was allowed to set for 1 hour and the color reaction was read in a microtiter plate reader at an absorbance of 405 nm. The results presented in FIG. 20 are the calculated as percent inhibition of sialic acid incorporation compared to strain 2019 grown in the absence of inhibitor. A total of ten potential inhibitors were studied initially, and only the 3-fluorosialic acid demonstrated inhibition.

EXAMPLE 5

Analysis of SiaP

Cloning and mutagenesis of siaP. The HI0146 (siaP) gene from H. influenzae Rd genome was cloned and shown to encode sialic acid binding protein of 329 amino acids, adjacent to the siaT sialic acid transporter (siaQM) identified previously in both NTHi 2019. The sialic acid transporter and sialic acid binding protein belong to the TRAP-type family of transporters. The functional siaP of NTHi 2019 was replaced with a copy of siaP disrupted with a kanamycin resistance gene (pCR146Kn). This was inserted into a pac1 site within siaP (FIG. 23). The resulting mutant was named NTHi 2019siaP. This mutation was constructed such a way to allow downstream transcription of siaT (FIG. 23). In addition, a version of the siaP mutant was constructed with an intact version of siaP inserted into a pseudogene in the strain 2019 genome. As will be seen, this "complemented" mutant was studied and shown to return the siaP mutant to a wildtype phenotype. Analysis of the SiaP protein indicated that it is a secreted protein and has a 23 amino acid leader sequence which is cleaved to form the mature protein upon secretion into the periplasmic space of the bacteria (FIG. 23B).

Comparative analysis of LOS from wild-type NTHi 2019 and NTHi 2019siaP. LOS was prepared from wild-type NTHi 2019 and NTHi 2019siaP grown on S-BHI agar medium supplemented with sialic acid (100 µM). A portion of the LOS was treated with neuraminidase and the resulting samples were resolved on an SDS-PAGE gel. The LOS isolated from the wild-type NTHi 2019 gave a glycoform pattern typical of this strain, some of the glycoforms are lost upon treatment of the LOS with neuraminidase indicating the presence of sialic acid in these glycoforms. The NTHi 2019siaP mutant has changed compared to the wild-type NTHi 2019, lacking a number of glycoforms, including the glycoform identified as containing sialic acid in the wild-type. Supporting this observation, treatment of the NTHi 2019siaP LOS with neuraminidase had no effect on the glycoform pattern seen by SDS-PAGE, suggesting that the LOS isolated from this mutant lacks sialic acid. When the siaP gene is reintroduced into the bacterial chromosome, LOS isolated from the resulting complemented mutant has the same glycoform pattern to that seen in the wild-type, in particular the predominant sialic acid-containing glycoform reappears as confirmed by neuraminidase treatment.

Western blot analysis was carried out using the mAb 3F11. LOS from the wild-type NTHi 2019 grown in the presence of sialic acid was negative for 3F11 binding. A number of glycoforms bind 3F11 upon treatment with neuraminidase, indicating that sialic acid was masking the terminal N-acetylactosamine epitope recognized by 3F11 . LOS from the NTHi 2019siaP mutant showed 3F11 binding prior to neuraminidase treatment and the binding pattern remains the same after neuraminidase treatment, indicating that sialic acid is not incorporated into the LOS. Interestingly, the glycoforms identified by 3F11 in NTHi 2019siaP are different than the glycoforms identified post-neuramiidase treatment in the wild-type LOS. These differences were also noted in the 2019siaT (sialic acid transporter) mutant, and are suggestive of changes in glycoform composition dependent on the availability of sialic acid. Upon complementation of the mutant the 3F11 reactivity returns to a pattern the similar to the wild-type with pre-neuraminidase LOS showing no reactivity and several glycoforms showing reactivity post-neuraminidase treatment. Interestingly, there appears to be a greater number of 3F11-reactive glycoforms after neuraminidase treatment in the wild-type and complemented mutant, suggesting possible effects of the reintroduction of siaP on the expression of specific glycoforms.

MALDI-TOF-MS of O-deacylated LOS. To investigate the LOS phenotype observed by SDS-PAGE, LOS from the wild-type and the siaP mutant were O-deacylated with anhydrous hydrazine and analyzed by MALDI-TOF-MS. Based on previous studies we expected to observe a complex mixture of glycoforms in the wild-type NTHi 2019, the major glycoform consisting of a lactose moiety (Galβ1,4-Glc-) linked in a β1,4 linkage to Hep$^I$ of the characteristic core structure of $H.$ $influenzae$ [Hep$^{III}$α1,2-Hep$^{II}$α1,3-Hep$^I$α1,5(P)Kdo-lipid A].

FIGS. 24A and B shows this to be the wild-type NTHi 2019, express a mixture of glycoforms with the lactose containing "B"-glycoforms with 2 or 3 phosphoethanolamine moieties ($B_2$ and $B_3$, respectively) dominating the spectrum. Other ions correlate to glycoforms which differ from the B-glycoform by the addition of as many as four hexoses and a single N-acetylhexosamine (for identities and m/z-, see Table 5). As well as these larger glycoforms there are number of smaller glycoforms which differ from the B-glycoform by the loss of a single hexose. A number of minor ions are observed in the absence of supplemental sialic acid representing glycoforms decorated with sialic acid moieties. Upon the addition of supplemental sialic acid to the media these sialylated glycoforms become intensified and further sialyalted glycoforms become apparent (FIG. 24B, Table 5). The glycoforms present in the O-LOS from the NTHi 2019siaP mutant, is very similar to that of the wild-type, with a very similar distribution of glycoforms (FIG. 24C, Table 5). However, the O-LOS from the mutant lacks sialic acid-containing glycoforms even though the bacteria were grown on media supplemented with sialic acid, suggesting a role for SiaP in the uptake or processing of sialic acid. When the siaP gene is added back to the mutant strain, sialic acid is once again incorporated into the LOS (FIG. 24D, Table 5). Reintroducing the siaP gene appears to have little effect on the expression of the various sialylated LOS glycoforms when compared to the wild-type (compare FIG. 24B and C), suggesting that the addition of the functional siaP has not disrupted any genes involved in the expression of specific glycoforms.

TABLE 5

| Glycoform | Composition Hex, HexNAc, NeuAc, PEA | $M_{Av}$ | $M_{Obs}$ FIG. XA | XB | XC | XD |
|---|---|---|---|---|---|---|
| $A_2$ | 1, 0, 0, 2 | 2237.9 | 2237.8 | 2237.8 | 2238.3 | 2238.0 |
| $A_3$ | 1, 0, 0, 3 | 2361.0 | 2360.9 | 2361.0 | 2361.0 | 2360.8 |
| $B_1$ | 2, 0, 0, 1 | 2277.0 | | | 2277.5 | 2276.8 |
| $B_2$ | 2, 0, 0, 2 | 2400.0 | 2400.0 | 2400.1 | 2400.0 | 2400.0 |
| $B_3$ | 2, 0, 0, 3 | 2523.1 | 2523.1 | 2523.1 | 2523.0 | 2523.1 |
| $C_1$ | 3, 0, 0, 1 | 2439.1 | 2438.9 | 2438.5 | 2438.9 | 2438.9 |
| $C_2$ | 3, 0, 0, 2 | 2562.2 | 2562.1 | 2562.7 | 2561.8 | 2562.5 |
| $C_3$ | 3, 0, 0, 3 | 2685.2 | 2686.9 | 2688.7 | | 2688.3 |
| $D_1$ | 4, 0, 0, 1 | 2601.3 | 2601.2 | 2602.1 | 2601.7 | 2601.9 |
| $D_2$ | 4, 0, 0, 2 | 2724.4 | 2724.4 | 2724.6 | 2724.3 | 2724.3 |
| $D_3$ | 4, 0, 0, 3 | 2847.4 | 2847.2 | 2847.7 | 2847.0 | 2847.4 |
| $E_1$ | 5, 0, 0, 1 | 2763.4 | 2762.6 | | 2762.5 | 2763.5 |
| $E_2$ | 5, 0, 0, 2 | 2886.5 | 2886.9 | 2885.1 | 2885.2 | 2886.3 |
| $E_3$ | 5, 0, 0, 3 | 3009.5 | 3010.7 | 3007.6 | 3009.5 | 3009.1 |
| $F_1$ | 3, 1, 0, 1 | 2642.3 | | 2643.1 | | |
| $G_1$ | 4, 1, 0, 1 | 2804.5 | | | 2803.9 | 2804.4 |
| $G_2$ | 4, 1, 0, 2 | 2927.5 | | 2927.6 | 2926.8 | 2926.9 |
| $H_1$ | 5, 1, 0, 1 | 2966.6 | | | 2966.1 | 2967.3 |
| $H_2$ | 5, 1, 0, 2 | 3089.7 | | 3087.9 | 3088.8 | 3087.4 |
| $B_3$* | 2, 0, 1, 3 | 2814.4 | 2813.7 | 2814.5 | | 2814.5 |
| $B_2$** | 2, 0, 2, 2 | 2982.6 | | 2982.8 | | 2982.6 |
| $B_3$** | 2, 0, 2, 3 | 3105.6 | 3103.9 | 3105.7 | | 3105.7 |
| $D_1$* | 4, 0, 1, 1 | 2892.5 | | 2892.9 | | 2892.4 |
| $D_2$* | 4, 0, 1, 2 | 3015.6 | | 3014.6 | | 3014.9 |
| $D_2$** | 4, 0, 2, 2 | 3306.8 | 3304.7 | 3305.5 | | 3304.3 |
| $E_1$* | 5, 0, 1, 1 | 3054.7 | 3055.5 | see F2* | | 3055.7 |
| $E_2$* | 5, 0, 1, 2 | 3177.7 | see F3* | see F3* | | see F3* |
| $E_3$* | 5, 0, 1, 3 | 3300.8 | | | | 3299.9 |
| $E_1$** | 5, 0, 2, 1 | 3345.9 | 3346.1 | 3347.8 | | 3344.4 |
| $E_2$** | 5, 0, 2, 2 | 3469.0 | 3469.1 | 3469.8 | | 3470.9 |
| $E_3$** | 5, 0, 2, 3 | 3592.0 | | 3590.7 | | 3592.1 |
| $F_2$* | 3, 1, 1, 2 | 3056.6 | see E1* | 3057.9 | | see E1* |

TABLE 5-continued

| Glycoform | Composition Hex, HexNAc, NeuAc, PEA | $M_{Av}$ | $M_{Obs}$ FIG. XA | XB | XC | XD |
|---|---|---|---|---|---|---|
| $F_3$* | 3, 1, 1, 3 | 3179.7 | 3179.1 | 3180.9 | | 3181.7 |
| $H_2$* | 5, 1, 1, 2 | 3380.9 | 3378.6 | 3380.9 | | 3380.9 |
| $I_2$* | 6, 1, 1, 2 | 3543.1 | 3542.4 | 3544.3 | | 3543.5 |
| $I_2$** | 6, 1, 2, 2 | 3834.3 | | 3835.1 | | 3834.7 |
| $I_3$** | 6, 1, 2, 3 | 3957.4 | | 3959.3 | | 3958.5 |
| $I_2$*** | 6, 1, 3, 2 | 4125.6 | | 4125.9 | | 4123.0 |

Bactericidal assays. It has been demonstrated previously that there is a correlation between the incorporation of terminal sialic acid into LOS and protection of H. influenzae from complement-mediated killing by normal human serum. Since it appears that the NTHi 2019siaP mutant is incapable of incorporating sialic acid into its LOS it would seem likely that this mutant would have increased susceptibility to killing by normal human serum. To address this hypothesis we carried out bactericidal assays on wild-type NTHi 2019 and the NTHi 2019siaP mutant. When grown in the absence of sialic acid both the wild-type and siaP mutant were susceptible to killing by normal human serum (FIG. 25A). Upon addition of supplemental sialic acid to the media the wild-type strain became resistant to serum killing, however, the siaP mutant remained susceptible (FIG. 25B). As a control the experiment was repeated using heat-inactivated human serum (Δ symbol above column), under these conditions neither the wild-type nor the siaP mutant were susceptible to serum killing (FIGS. 25A and B). Studies with the complemented siaP mutant indicated that it had the same phenotype as the wildtype strain 2019 in bactericidal assays.

Bioflim formation. Previous work with the 2019siaT mutant has shown that inactivation of sialic acid transport has a detrimental affect on the viability of cells within a biofilm (Allen et al., 2005). A continuous-flow cell assay was used to determine if the biofilm formation phenotype of 2019siaP and 2019siaPsiaT was similar to 2019siaT. Biofilm chambers were grown and examined at 24 and 48 hours after inoculation. Chambers examined after 24 hours revealed little difference between wild-type and mutant strains (data not shown). By 48 hours post-inoculation there is a significant difference between wild-type and the various sialic acid transporter mutants (FIG. 26). The Live/Dead stain (Molecular Probes, Eugene, Oreg.) is capable of distinguishing live from dead bacteria. Live bacteria fluoresce green and red bacteria fluoresce red. While 2019 produced a biofilm with a majority of viable cells present, the three mutant biofilms consisted of predominantly dead cells (FIG. 26). Clearly, sialic acid is not required for biofilm formation, however the loss of sialic acid transport is required for long-term viability of bacteria within the bioflim. These results are consistent with previous observations with 2019siaT and confirm the necessity for sialic in bioflim formation.

SiaP binds sialic acid. SiaP was overexpressed in a PET15 vector and purified to homogeneity from E. coli. It was then crosslinked to Sepharose® beads and the ability of the SiaP-Sepharose® conjugate to bind sialic acid was assessed using $^3$H-labelled sialic acid. FIG. 5 shows that SiaP is capable of binding sialic acid. Non-specific binding was not observed in this system as evidenced by the LuxS-Sepharose® and Sepharose®-only controls (FIG. 26).

Biacore® Analysis: Surface plasmon resonance analysis was performed to measure the affinity of binding of sialic acid to SiaP. These studies were performed on a Biacore® instrument using the CM5 sensor chip. SiaP was bound to the chip and increasing concentrations of sialic acid were introduced into the instrument. These studies showed increasing association of the sialic acid with the SiaP up to 20 mM concentration (FIG. 27). Increasing concentration of sialic acid up to 50 mM show minimal increase in binding. Based on the calculations from this analysis, an association constant of $1.7 \times 10^7$ M was calculated. Studies with glucose, galactose, glucosamine, N-acetylglucosamine, and N-acetyl mannosamine showed no evidence of binding at concentrations as high as 100 mM in the Biacore® system.

Calorimetry and Dynamic Light Scattering. Isothermal titration calorimetry (ITC) experiments were performed in order to determine the binding affinity of SiaP for sialic acid. The n value, calculated from the binding data, was always less than one. FIG. 28 shows changes in heat of binding (Y-axis) as sialic acid concentration (X-axis) increases relative to SiaP as the concentration of sialic acid increases. The reduced value of n is likely due to the presence of inactive protein due to binding to endogenous sialic acid bound or error in the calculated protein concentration. Data from three independent experiments were used to calculate the $K^a=1.34+/-(0.13) \times 10^{-7}$ M or $K_d=0.13$ uM. Dynamic light scattering (DLS) experiments were performed to determine the hydrodynamic radius of SiaP with and without sialic acid. Results from the DLS experiments indicate that the protein is monomeric and the molecular weight or stokes radius did not change after sialic acid was added. This was verified by two types of experiments. In the first experiment, excess sialic acid was incubated with SiaP for several hours before DLS experiments were performed. In the second, DLS was performed on protein taken from the calorimeter following an ITC experiment.

All publications, patents and patent applications are incorporated herein by reference. While in the foregoing specification this invention has been described in relation to certain embodiments thereof, and many details have been forth for purposes of illustration, it will be apparent to those skilled in the invention is susceptible to addtional embodiments and that certain of the details described herein may be varied considerably without departing from the basic principles of the invention.

What is claimed is:

1. A method of treating a mammal infected with a bacterium comprising a sialic acid permease, the method comprising administering a bacterial sialic acid permease inhibitory agent to the mammal, wherein the inhibitor is administered in an amount that reduces the transport of sialic acid by the bacterium, wherein the bacterium is *Haernophilus influenzae, Haemophilus ducrevi, Vibrio cholera* or *Fusobacterium nucleatum*, and wherein the inhibitor is 3-fluoro-N-acetylneuraminic acid (3FNA) or an N-alkano, d-derivative of sialic acid.

2. The method of claim 1, wherein the mammal is diagnosed with otitis media, otitis media with effusion, pneumonia, or chronic bronchitis.

3. The method of claim 1, wherein the bacterium is *Haemophilus influenzae*.

4. The method of claim 1, wherein the transport of sialic acid by the bacterium is reduced by at least about 10%.

5. The method of claim 1, wherein the agent is present in a physiologically-acceptable, non-toxic vehicle.

6. The method of claim 1, wherein the viral neuraminidase inhibitor is 3-fluoro-N-acetylneuraminic acid (3FNA).

7. The method of claim 1, wherein the inhibitory agent is an N-alkanoyl-derivative of sialic acid.

8. The method of claim 7, wherein the N-alkanoyl-derivative of sialic acid is a 5-N-octanoyl derivative of sialic acid (SiaOct).

9. The method of any of the preceding claims, wherein the sialic acid permease is siaP or siaT.

10. The method of claim 1, wherein the bacterium is *Haemophilus ducreyi*.

11. The method of claim 1, wherein the bacterium is *Vibrio cholerae* or *Fusobacterium nucleatum*.

12. A method of treating a *Haemophihis influenzae* or *Haemophilus ducreyi* infection, comprising administering to a patient a sialic acid permease inhibitory agent, wherein the inhibitory agent is 3-fluoro-N-acetylneuraminic acid (3FNA) or an N-alkanoyl-derivative of sialic acid.

13. The method of claim 12, wherein the inhibitory agent is 3-fluoro-N-acetylneuraminic acid (3FNA).

14. The method of claim 12, wherein the inhibitory agent is an N-alkanoyl-derivative of sialic acid.

15. The method of claim 14, wherein the N-alkanoyl-derivative of sialic acid is a 5-N-octanoyl derivative of sialic acid (SiaOct).

* * * * *

UNITED STATES PATENT AND TRADEMARK OFFICE
CERTIFICATE OF CORRECTION

PATENT NO. : 7,413,729 B2  
APPLICATION NO. : 11/331735  
DATED : August 19, 2008  
INVENTOR(S) : Michael A. Apicella et al.

Page 1 of 1

It is certified that error appears in the above-identified patent and that said Letters Patent is hereby corrected as shown below:

In the Specification

In Column 1, Line 14-16, in the Federally Sponsored Research or Development clause, please replace the existing text with the following clause:

This invention was made with government support under Grant No. A124646 and Grant No. A130040 awarded by the National Institutes of Health. The Government has certain rights in the invention.

Signed and Sealed this  
First Day of July, 2014

Michelle K. Lee  
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 7,413,729 B2 | Page 1 of 1 |
| APPLICATION NO. | : 11/331735 | |
| DATED | : August 19, 2008 | |
| INVENTOR(S) | : Apicella et al. | |

It is certified that error appears in the above-identified patent and that said Letters Patent is hereby corrected as shown below:

In the Specification

In Column 1 under Federally Sponsored Research or Development (See the Certificate of Correction issued July 1, 2014):

Replace:

This invention was made with government support under Grant No. A124646 and Grant No. A130040 awarded by the National Institutes of Health. The Government has certain rights in the invention.

With:

This invention was made with government support under AI24616 and AI30040 awarded by the National Institutes of Health. The government has certain rights in the invention.

In the Claims

In Claim 1, Column 63 Line 38:

Replace:

*Haernophilus*

With:

*Haemophilus*

Signed and Sealed this
Seventh Day of July, 2015

Michelle K. Lee
*Director of the United States Patent and Trademark Office*